US009333268B2

(12) United States Patent
Bomalaski et al.

(10) Patent No.: US 9,333,268 B2
(45) Date of Patent: *May 10, 2016

(54) METHODS OF TREATMENT WITH ARGININE DEIMINASE

(71) Applicant: Polaris Group, Grand Cayman (KY)

(72) Inventors: John S. Bomalaski, Wayne, PA (US); Bor-Wen Wu, San Diego, CA (US)

(73) Assignee: Polaris Group, Grand Cayman (KY)

( * ) Notice: Subject to any disclaimer, the term of this patent is extended or adjusted under 35 U.S.C. 154(b) by 0 days.

This patent is subject to a terminal disclaimer.

(21) Appl. No.: 14/701,825

(22) Filed: May 1, 2015

(65) Prior Publication Data

US 2015/0231272 A1  Aug. 20, 2015

Related U.S. Application Data

(63) Continuation of application No. 13/878,745, filed as application No. PCT/US2012/039979 on May 30, 2012.

(60) Provisional application No. 61/620,368, filed on Apr. 4, 2012.

(51) Int. Cl.
| *A61K 47/48* | (2006.01) |
| *A61K 38/50* | (2006.01) |
| *A61K 45/06* | (2006.01) |
| *A61K 33/24* | (2006.01) |
| *A61K 31/337* | (2006.01) |
| *A61K 31/436* | (2006.01) |

(52) U.S. Cl.
CPC ......... *A61K 47/48215* (2013.01); *A61K 31/337* (2013.01); *A61K 31/436* (2013.01); *A61K 33/24* (2013.01); *A61K 38/50* (2013.01); *A61K 45/06* (2013.01); *C12Y 305/03006* (2013.01)

(58) Field of Classification Search
None
See application file for complete search history.

(56) References Cited

U.S. PATENT DOCUMENTS

| 6,183,738 | B1 | 2/2001 | Clark |
| 6,635,462 | B1 | 10/2003 | Ensor et al. |
| 7,204,980 | B2 | 4/2007 | Clark |
| 7,323,167 | B2 | 1/2008 | Clark |
| 2003/0215429 | A1 | 11/2003 | De Simone |
| 2004/0258675 | A1 | 12/2004 | Ensor et al. |
| 2005/0129706 | A1 | 6/2005 | Clark |
| 2006/0002915 | A1 | 1/2006 | Min et al. |
| 2007/0198198 | A1 | 8/2007 | Burczynski et al. |
| 2009/0238813 | A1 | 9/2009 | Georgiou et al. |
| 2010/0197944 | A1 | 8/2010 | Palle et al. |
| 2011/0111403 | A1 | 5/2011 | Petrauskene et al. |
| 2011/0301189 | A1 | 12/2011 | Khattar et al. |
| 2012/0015049 | A1 | 1/2012 | Zhang |
| 2013/0052179 | A1 | 2/2013 | Huang et al. |
| 2014/0348814 | A1 | 11/2014 | Almassy et al. |
| 2015/0132278 | A1 | 5/2015 | Bomalaski et al. |

FOREIGN PATENT DOCUMENTS

| EP | 1987838 B1 | 1/2016 |
| JP | 2001-524836 | 12/2001 |
| JP | 2006-515281 | 5/2006 |
| JP | 2009-523433 | 6/2009 |
| KR | 10-2004-0004449 | 1/2004 |
| WO | WO 98/51784 | 11/1998 |
| WO | WO 02/44360 | 6/2002 |
| WO | WO 2004/046309 | 6/2004 |
| WO | WO 2013/151568 | 10/2013 |
| WO | WO 2014/151982 | 9/2014 |

OTHER PUBLICATIONS

Venugopal et al., "Histidine-dependent activation of Arginine Deiminase in Clostridium sporogenes: Kinetic Evidence on In Vivo Allosteric Interactions", FEBS Letters, 1975, 51(1):246-248.*
Supplementary European Search Report for European Application No. 12873622.0, mailed Oct. 12, 2015, 11 pages.
International Search Report and Written Opinion for International Application No. PCT/US2014/026766, mailed Oct. 24, 2014, 14 pages.
Avramis, V. I. et al., "Pharmacokinetic/Pharmacodynamic Relationships of Asparaginase Formulations," Clin Pharmacokinet, 44(4):367-393 (2005).
Delage, B. et al., "Abstract 4445: Pegylated arginine deiminase induces mitochondrial apoptosis and synergizes with cisplatin in ASS1-negative malignant pleural mesothelioma," In: Proceedings of the 101st Annual Meeting of the American Association for Cancer Research, Apr. 17-21, 2010, Washington, DC, Philadelphia, PA: AACR; Cancer Research, 70(8 Suppl): Abstract nr 4445 (2010), 2 pages.
Feun, L. et al., "Pegylated arginine deiminase: a novel anticancer enzyme agent," Expert Opin. Investig. Drugs., 15(7):815-822 (2006).
Fu, C. H. et al., "PEG-asparaginase," Expert Opinion Pharmacotherapy, 8(12):1977-1984 (2007).
Izzo, F. et al., "Pegylated Arginine Deiminase Treatment of Patients With Unresectable Hepatocellular Carcinoma: Results From Phase I/II Studies," Journal of Clinical Oncology, 22(10):1815-1822 (2004).
Pinheiro, J. P. V. et al., "The best way to use asparaginase in childhood acute lymphatic leukaemia—still to be defined?", British Journal of Haematology, 125:117-127 (2004).
Rodriguez, C. O. et al., "Abstract 4848: Pegylated arginine deiminase induces autophagy in canine melanoma and canine osteosarcoma," In: Proceedings of the 101st Annual Meeting of the American Association for Cancer Research, Apr. 17-21, 2010, Washington, DC, Philadelphia, PA: AACR Cancer Research, 70(8 Suppl.):Abstract nr 4848 (2010), 2 pages.
Zeidan, A. et al., "Pegasparaginase: where do we stand?", Expert Opinion Biol. Ther, 9(1):111-119 (2009).
UniProtKB Submission F9UJU2_9MOLU, Arginine deiminase; Mycoplasma columbinum SF7 (Jan. 9, 2013). Retrieved from the Internet Jun. 22, 2014: <http://www.uniprot.org/uniprot/F9UJU2.txt?version=6>, 1 page.

(Continued)

*Primary Examiner* — Suzanne M Noakes
(74) *Attorney, Agent, or Firm* — Cooley LLP

(57) ABSTRACT

The present invention relates generally to methods of treating cancer with arginine deiminase, and in particular pegylated arginine deiminase.

15 Claims, 20 Drawing Sheets

(56) References Cited

OTHER PUBLICATIONS

UniProtKB/TrEMBL Submission A7LHN6_9MOLU (Jan. 9, 2013) Retrieved from the Internet Jun. 22, 2014: <http://www.uniprot.org/uniprot/A7LHN6.txt?version=28>, 1 page.

Ascierto, P., et al., "Pegylated Arginine Deiminase Treatment of Patients with Metastitic Melanoma: Results from Phase I and II Studies," Journal of Clinical Oncology, vol. 23, No. 30, Oct. 20, 2005, pp. 7660-7668 and 4047.

Bowles, T., et al., "Pancreatic Cancer Cell Lines Deficient in Argininosuccinate Synthetase are Sensitive to Arginine Deprivation by Arginine Deiminase," Int. J. Cancer: 123, 2008, pp. 1950-1955.

Chen, N., et al., "Autophagy and Tumorigenesis," FEBS Letters 584, 2010, pp. 1427-1435.

Daylami, R., et al., "Abstract 4847: Arginine Deprivation by PEG-ADI Induces Autophagic Cell Death and Enhances the Tumor Suppression Effect of Gemcitabine in Pancreatic Cancer," Cancer Research, Apr. 15, 2010 70; 4847.

Delage, B., et al., "Arginine Deprivation and Argininosuccinate Synthetase Expression in the Treatment of Cancer," International Journal of Cancer, 126, 2010, pp. 2762-2772.

Ensor, C., et al., "Pegylated Arginine Deiminase (ADI-SS PEG20,000 mw) Inhibits Human Melanomas and Hepatocellular Carcinomas in Vitro and in Vivo," Cancer Research, Vo. 62, Oct. 1, 2002, pp. 5443-5450.

Feun, L., et al., "Arginine Deprivation as a Targeted Therapy for Cancer," Current Pharmaceutical Design, 2008, 14, pp. 1049-1057.

Glazer, E., et al., "Phase II Study of Pegylated Arginine Deiminase for Nonresectable and Metastatic Hepatocellular Carcinoma," Journal of Clinical Oncology, vol. 28, No. 13, May 1, 2010, pp. 2220-2226.

Gong, H., et al., "Arginine Deiminase Inhibits Proliferation of Human Leukemia Cells More Potently than Asparaginase by Inducing Cell Cycle Arrest and Apoptosis," Leukemia, vol. 14, 2000, pp. 826-829.

Guven, K., et al., "Cisplatin and Carboplatin Combination as Second-Lind Chemotherapy in Dacarbazine-Resistant Melanoma Patients," Melanoma Research, 11, 2001, pp. 411-415.

He, W., et al., "Abstract 4703: Lack of Expression of Argininosuccinate Synthetase in Human Cancer Tissue: A Biomarker for Sensitivity to Arginine Depetion with Pegylated Arginine Deiminase," Cancer Research, 70, Proceedings: AACR $101^{st}$ Annual Meeting 2010—Apr. 17-21, 2010, 2 pages.

Hernandez, C., et al., "Pegylated Arginase I: A Potential Therapeutic Approach in T-ALL," Blood, vol. 115, No. 25, Jun. 24, 2010, pp. 5214-5221.

Holtsberg, F., et al., "Poly(ethylene glycol) (PEG) Conjugated Arginine Deiminase: Effects of PEG Formulations on its Pharmacological Properties," Journal of Controlled Release 80, 2002, pp. 259-271.

Kelly, M., et al., Abstract 4519: Small Cell Lung Cancers Lack Expression of Argininosuccinate Synthase (ASS) and are sensitive to Arginine Deprivation Using Arginine Deiminase-PEG20 (ADI-PEG20), Cancer Research, 70, AACR $101^{st}$ Annual Meeting, Apr. 17-21, 2010, 2 pages.

Kelly, MP, et al., "Arginine Deiminase PEG20 Inhibits Growth of Small Cell Lung Cancers Lacking Expression of Argininosuccinate Synthetase," British Journal of Cancer, vol. 106, No. 2, 2012, pp. 324-332.

Kim, R., et al., "ADI, Autophagy and Apoptosis: Metabolic Stress as a Therapeutic Option for Prostate Cancer," Autophagy, vol. 5, No. 4, May 16, 2009, pp. 567-568.

Kim, R., et al., "Arginine Deiminase as a Novel Therapy for Prostate Cancer Induces Autophagy and Caspase-Independent Apoptosis," Cancer Research, vol. 69, No. 2, Jan. 15, 2009, pp. 700-708.

Komada, Y., et al., "Apoptoptic Cell Death of Human T Lymphoblastoid Cells Induced by Arginine Deimanse," International Journal of Hematology, 65, 1997, pp. 129-141.

Kung, C., et al., "Autophagy in Tumor Suppression and Cancer Therapy," Critical Reviews in Eukaryotic Gene Expression, vol. 21, No. 1, 2011, pp. 71-100.

Ni, Y., et al., Arginine Deiminase, a Potential Anti-Tumor Drug, Cancer Letters 261, 2008, pp. 1-11.

Noh, E., et al., "Arginine Deiminase Enhances Dexamethasone-Induced Cytotoxicity in Human T-Lymphoblastic Leukemia CCRF-CEM Cells," Int. J. Cancer: 112, 204, pp. 502-508.

Ohno, T., et al., "Argininosuccinate Synthetase Gene Expression in Leukemias: Potential Diagnostic Marker for Blastic Crisis of Chronic Myelocytic Leukemia," Leukemia Research, vol. 16, No. 5, 1992, pp. 475-483.

Savaraj, N., et al., "Arginine Deprivation, Autophagy, Apoptosis (AAA) for the Treatment of Melanoma," Current Molecular Medicine 2010, vol. 10, pp. 405-412.

Shen, L., et al., "Drug Evaluation: ADI-PEG-20—a PEGylated Arginine Deiminase for Arginine-Auxotrophic Cancers," Current Opinon in Molecular Therapeutics, 2006, vol. 8, No. 3, pp. 240-248.

Sugimura, K., et al., "Tumor Growth Inhibitory Activity of a Lymphocyte Blastogenesis Inhibitory Factor," Cancer Research, 50, Jan. 15, 1990, pp. 345-349.

Sugimura, K., et al., "Elevated Argininosuccinate Synthetase Activity in Adult T Leukemia Cell Lines," Leukemia Research, vol. 14, No. 10, 1990, pp. 931-934.

Szlosarek, P., et al., "Abstract 4067: Pegylated Arginine Deiminase (ADI-PEG20) as a Potential Novel Therapy for Argininosuccinate Synthetase-Deficient Acute Myeloid Leukemia," Proceedings of the $102^{nd}$ Annual Meeting of the American Associate for Cancer Research, Apr. 2-6, 2011, vol. 71, No. 8 (Supp), 2 pages.

Szlosarek, P., et al., "In Vivo Loss of Expression of Argininosuccinate Synthetase in Malignant Pleural Mesothelioma is a Biomarker for Susceptibility to Arginine Depletion," Cancer Therapy: Preclinical, Clin Cancer Research, vol. 12, No. 23. Dec. 1, 2006, pp. 7123-7131.

Szlosarek, P., et al., "Effect of Inactivation of Argininosuccinate Synthetase on Sensitivity of Lymphomas to Caspase-Dependent Apoptosis Following Treatment with Arginine Deiminase," Journal of Clinical Oncology, vol. 28. No. 15 (May 20 Supp), 2010, 2 pages.

Yang, T., et al., "A Randomised Phase II Study of Pegylated Arginine Deiminase (ADI-PEG 20) in Asian Advanced Hepatocellular Carcinoma Patients," British Journal of Cancer, vol. 103, 2010, pp. 954-960.

You, M., et al., "Abstract 61: Enhancing Arginine Deprivation Therapy in Melanoma by Combining with Cisplatin," Proceedings of the $101^{st}$ Annual Meeting of the American Association for Cancer Research, Apr. 17-21, 2010, AACR Cancer Research 2010; vol. 70, No. 8 (Supp), 2 pgs.

You, M. et al., "Abstract #3418: Arginine Deprivation and Soluble TRAIL Strikingly Enhance Death in Argininosuccinate Synthetase Negative Melanoma Cells," Proc. Am. Assoc. Cancer Research; Apr. 18-22, 2009, 2 pages.

You, M., et al., "Abstract 4096: TRAIL Enhances Cytotoxicity of Arginine Depletion Therapy in Argininosuccinate Synthetase-Negative Melanoma Cells Through Interruption of Autophagy Via Activation of Caspases," Proceedings of the $102^{nd}$ Annual Meeting of the American Association for Cancer Research; Apr. 2-6, 2011, Cancer Research 2011, vol. 71, No. 8 (Supp), 2 pages.

You, M., et al., "The Combination of ADI-PEG20 and TRAIL Effectively Increases Cell Death in Melanoma Cell Lines," Biochemical and Biophysical Research Communications 394, 2010, pp. 760-766.

Zamora, R., et al. Inducible Nitric Oxide Synthase and Inflammatory Diseases, Molecular Medicine, vol. 6, No. 5, May, 2000, pp. 347-360.

English Translation Office Action mailed Dec. 24, 2014 from Japanese Patent Office in JP2014-520183, 6 pages.

Office Action mailed Nov. 13, 2014 from Canadian Patent Office in CA 2,834,083, 4 pages.

Office Action mailed Nov. 14, 2014 from Australian Patent Office in AU2012330497, 4 pages.

English Translation Office Action mailed Sep. 20, 2014 from Taiwanese Patent Office in TW101119399, 2 pages.

English Translation Search Report mailed Sep. 20, 2014 from Taiwanese Patent Office in TW101119399, 2 pages.

International Search Report and Written Opinion Issued in PCT/US12/39979 on Oct. 22, 2012.

Bi, D. et al., Isolation and identification of mycoplasmas from pigeons, Chinese Journal of Animal Poultry and Infectious Diseases, 19(6):1-5 (1997) [English translation].

(56) References Cited

OTHER PUBLICATIONS

International Pharmaceutical Excipients Council Japan (ed.), lyakutenkabutsu Jiten [Pharmaceutical Excipient Dictionary] 2007, Yakuji Nippo Limited, Jul. 25, 2007, p. 220-221.

Wang, M. et al., "Engineering an arginine catabolizing bioconjugate: Biochemical and pharmacological characterization of PEGylated derivatives of arginine deiminase from mycoplasma arthritidis," Bioconjugate Chem., 17:1447-1459 (2006).

* cited by examiner

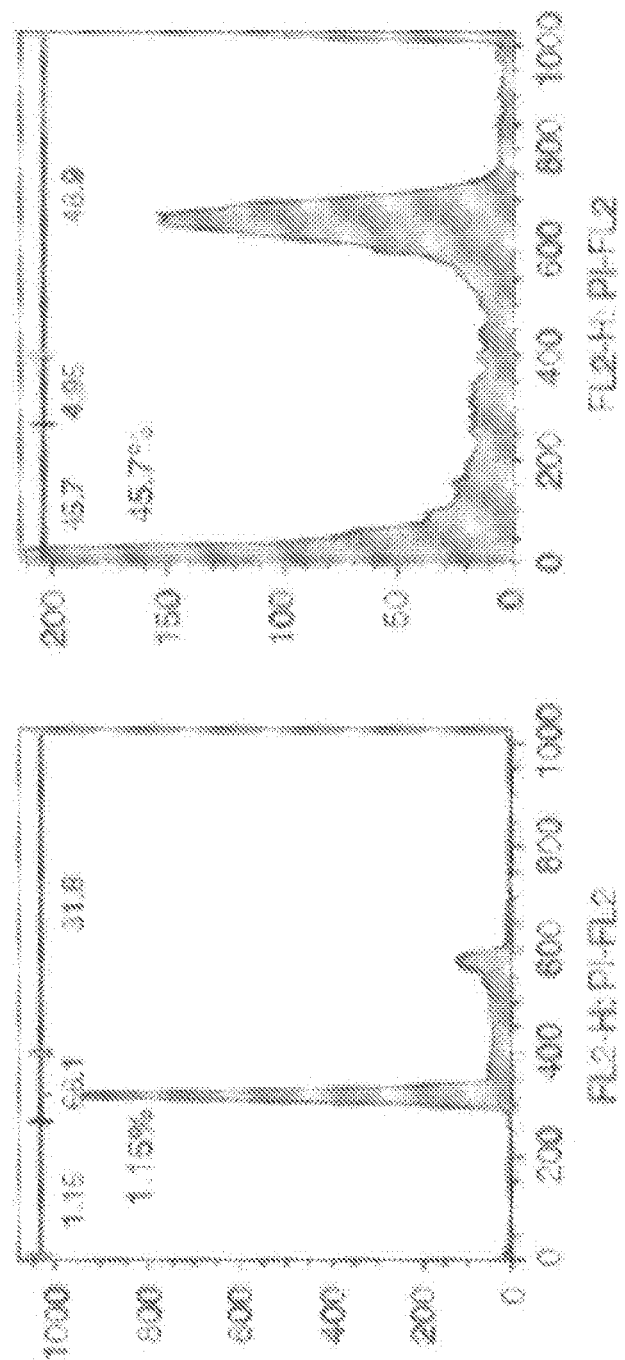

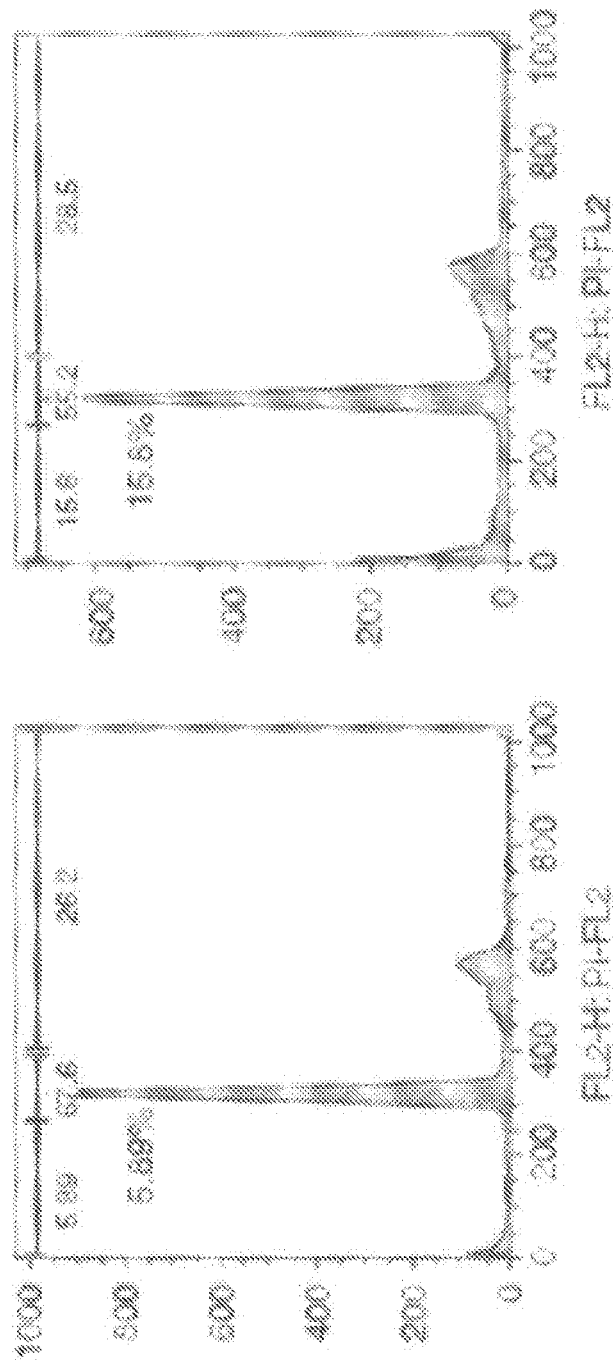

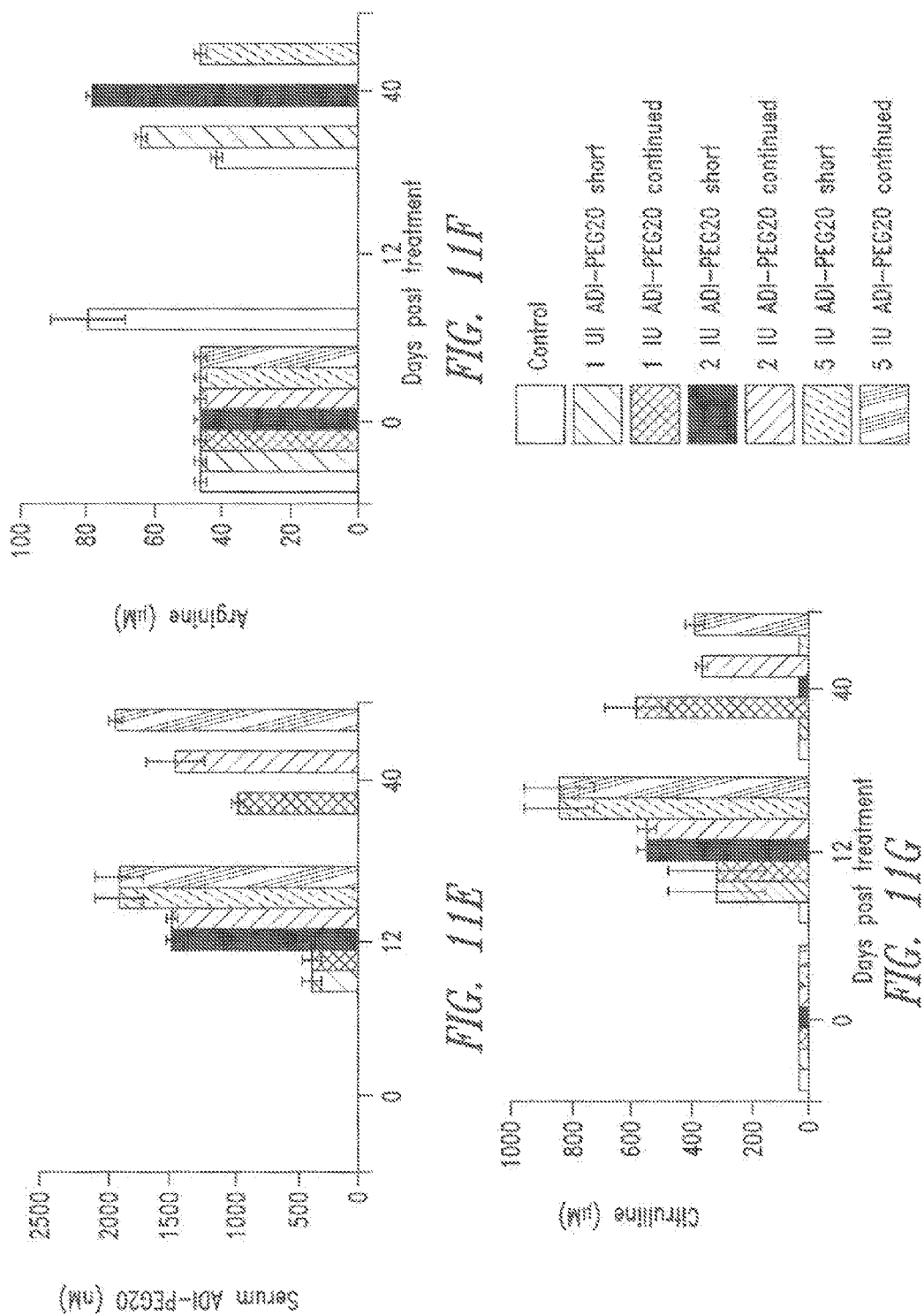

METHODS OF TREATMENT WITH ARGININE DEIMINASE

CROSS REFERENCE TO RELATED APPLICATIONS

This application is a Continuation of U.S. application Ser. No. 13/878,745, filed Jan. 16, 2015; which is a U.S. National Phase Application of International Patent Application No. PCT/US2012/039979, filed May 30, 2012, which claims the benefit under 35 U.S.C. §119(e) of U.S. Provisional Application No. 61/620,368, filed on Apr. 4, 2012, which application is incorporated by reference herein in its entirety.

STATEMENT REGARDING SEQUENCE LISTING

The Sequence Listing associated with this application is provided in text format in lieu of a paper copy, and is hereby incorporated by reference into the specification. The name of the text file containing the Sequence Listing is POLA_001_02US_ST25.txt. The text file is 8 KB, was created on Apr. 30, 2015, and is being submitted electronically via EFS-Web.

BACKGROUND

1. Technical Field

The present invention relates generally to methods of treating cancer with arginine deiminase (ADI), and in particular pegylated ADI (ADI-PEG).

2. Description of the Related Art

Amino acid deprivation therapy can be an effective treatment of some forms of cancer. To date, there is one known clinical example relevant to this approach which utilizes asparaginase to lower circulating levels of asparagine and inhibit protein synthesis. This treatment is particularly effective for acute lymphoblastic leukemia (Avramis 2005, Viera Pinheiro 2004). Acute lymphoblastic leukemia cells require the amino acid asparagine for growth and proliferation. In contrast, most normal human cells are capable of synthesizing asparagine and are unaffected by asparagine depletion. Therefore, decreasing serum asparagine with asparaginase can selectively kill the cancer cells without harming the normal cells, tissues, and host. An *E. coli* derived form of asparaginase has been approved for human use. However, asparaginase is found only in microbes; which makes it highly immunogenic in humans and also has a short serum half-life following injection (Avramis 2005). To make asparaginase a more effective drug, these drawbacks were minimized by formulating the *E. coli* derived asparaginase with polyethylene glycol (PEG) to reduce the antigenicity of this enzyme and the associated allergic reactions. In addition, PEG greatly prolongs the circulating half-life of asparaginase, which reduces both the frequency of treatment and the total cost of the therapy. PEG formulated asparaginase is approved for use and is marketed under the trade name Oncaspar® (Oncaspar® 2011, Avramis 2005, Viera Pinheiro 2004, Fu 2007, Zeidan 2008).

Arginine is another non-essential amino acid for humans and mice (for review see Rogers 1994). In humans, arginine can be synthesized from citrulline in two steps via the Krebs (urea) cycle enzymes argininosuccinate synthetase (ASS, L-citrulline:L-aspartate ligase [AMP-forming], EC 6.3.4.5) and argininosuccinate lyase (ASL, L-argininosuccinate arginine-lyase, EC 4.3.2.) (Haines 2011, Wu 2009, Morris 2006, Husson 2003, Tapiero 2002, Rogers 1994). ASS catalyzes the conversion of citrulline and aspartic acid to argininosuccinate, which is then converted to arginine and fumaric acid by ASL (FIG. 1). An arginine deficient diet in humans does not evoke hyperammonemia, orotic aciduria, nor alter the rate of whole body nitric oxide (NO) synthesis in adult humans (Tapiero 2002, Castillo 1995, Rogers 1994, Carey 1987, Barbul 1986, Snyderman 1959, Rose 1949). Although preterm infants appear to require arginine (Wu 2004), arginine levels do not correlate with age among infants, children and young adults (Lücke 2007). In 1992, Takaku and Sugimura separately reported that human melanomas and hepatocellular carcinoma (HCC) cell lines appear to require arginine for growth. Other studies showed that pegylated ADI was effective for the treatment of melanomas and hepatomas with few adverse effects.

Cancer is primarily treated with one or a combination of three types of therapies: surgery, radiation, and chemotherapy. For cancers that cannot be treated with local therapies such as surgery, radiation and embolization, systemic chemotherapies are the only treatment option. However, traditional chemotherapies cannot distinguish between normal and cancer cells, which lead to significant toxicity and limited efficacy. The new generation of systemic therapy is targeted therapies designed to kill cancer cells selectively by exploiting differences between normal and cancer cells. The present invention provides this and other advantages for the treatment of cancers.

References: Avramis V I, Panosyan E H. 2005. Clin Pharmacokinet 44:367-393; Barbul A. 1986. J Parenteral Enteral Nutr 10:227-238; Carey G P, et al. 1987. J Nutr 117:1734-1739; Castillo L, et al. 1995. Am J Physiol 268 (Endocrinol Metab 31): E360-367; Fu C H, Sakamoto K M. 2007. Expert Opin Pharmacother 8:1977-1984; Haines R J, et al. 2011. Int J Biochem Mol Biol 2:8-23; Husson A, et al. 2003. Eur J Biochem 270:1887-1899; Lücke T, et al. 2007. Clin Chem Lab Med 45:1525-1530; Morris S M Jr. 2006. Am J Clin Nutr 83 (Suppl):5985-5125; Rogers Q R. 1994. In Proceedings from a Symposium Honoring Willard J. Visek—from Ammonia to Cancer and Gene Expression. Special Publication 86—April, 1994, Agriculture Experiment Station, University of Illinois, 211 Mumford Hall, Urbana, Ill. 61801, pp. 9-21; Tapiero H, et al. 2002. Biomed Pharmacother 56:439-445, 2002; Viera Pinheiro J P, Boos J. 2004. Br J Haematol 125: 117-127; Wu G, et al. 2009. Amino Acids 37:153-168; Wu G, et al. 2004. J Nutr Biochem 15:442-451; Zeidan A, et al. 2008. Expert Opin Biol Ther 9:111-119.)

BRIEF SUMMARY

One aspect of the present invention provides a method of treating leukemia in a patient comprising administering to the patient a compound comprising ADI covalently bonded via a linking group to polyethylene glycol. In one embodiment, the leukemia is acute myeloid leukemia or relapsed acute myeloid leukemia. In a further embodiment, the leukemia is not lymphocytic leukemia or chronic myelogenous leukemia. However in further embodiments the leukemia may include lymphocytic leukemia or chronic myelogenous leukemia. In another embodiment, the arginine deiminase is covalently bonded to 5±1.5 straight chain PEG molecules and the compound is formulated in a composition comprising less than about 0.5% native ADI, less than about 5% free PEG, or both; wherein the arginine deiminase is administered weekly at a dose of about 160 IU/m$^2$ to about 640 IU/m$^2$; and wherein the leukemia exhibits reduced expression of ASS.

Another aspect of the present invention provides a method of treating a cancer in a patient comprising administering to the patient an autophagy inhibitor and a compound comprising ADI covalently bonded via a linking group to polyethylene glycol, wherein the cancer is pancreatic cancer or small cell lung cancer. In this regard an autophagy inhibitor is selected from the group consisting of chloroquine, 3-methyladenine, hydroxychloroquine, bafilomycin A1, 5-amino-4-imidazole carboxamide riboside (AICAR), okadaic acid, N6-mercaptopurine riboside, wortmannin, and vinblastine. Other autophagy inhibitors known in the art are contemplated for use in the methods herein. In certain embodiments, the ADI and the autophagy inhibitor act additively or synergistically. In another embodiment, the arginine deiminase is covalently bonded to 5±1.5 straight chain PEG molecules and the compound is formulated in a composition comprising less than about 0.5% native ADI, less than about 5% free PEG, or both; wherein the arginine deiminase is administered weekly at a dose of about 160 IU/m2 to about 640 IU/m2; and wherein the cancer exhibits reduced expression of ASS.

One aspect of the present invention provides a method of treating a cancer in a patient comprising administering to the patient a compound comprising ADI covalently bonded via a linking group to polyethylene glycol, wherein the cancer is selected from the group consisting of breast cancer, ovarian cancer, colorectal cancer, gastric cancer, glioma, glioblastoma multiforme, non-small cell lung cancer (NSCLC), kidney cancer, bladder cancer, uterine cancer, esophageal cancer, brain cancer, head and neck cancers, cervical cancer, testicular cancer, and stomach cancer. In one embodiment, the arginine deiminase is covalently bonded to 5±1.5 straight chain PEG molecules and the compound is formulated in a composition comprising less than about 0.5% native ADI, less than about 5% free PEG, or both; wherein the arginine deiminase is administered weekly at a dose of about 160 IU/m2 to about 640 IU/m2; and wherein the cancer exhibits reduced expression of ASS.

One aspect of the present invention provides a method of treating melanoma in a patient comprising administering to the patient a compound comprising ADI covalently bonded via a linking group to polyethylene glycol, in combination with cisplatin. In one embodiment, the arginine deiminase is covalently bonded to 5±1.5 straight chain PEG molecules and the compound is formulated in a composition comprising less than about 0.5% native ADI, less than about 5% free PEG, or both; wherein the arginine deiminase is administered weekly at a dose of about 160 IU/m2 to about 640 IU/m2; and wherein the melanoma exhibits reduced expression of ASS.

Another aspect of the present invention provides a method of treating a cancer in a patient comprising administering to the patient a compound comprising ADI covalently bonded via a linking group to polyethylene glycol, wherein the cancer is not melanoma, pancreatic cancer, prostate cancer, small cell lung cancer, mesothelioma, lymphocytic leukemia, chronic myelogenous leukemia, lymphoma, hepatoma, and sarcoma. In one embodiment, the arginine deiminase is covalently bonded to 5±1.5 straight chain PEG molecules and the compound is formulated in a composition comprising less than about 0.5% native ADI, less than about 5% free PEG, or both; wherein the arginine deiminase is administered weekly at a dose of about 160 IU/m2 to about 640 IU/m2; and wherein the cancer exhibits reduced expression of ASS.

Another aspect of the present disclosure provides a method of treating non-small cell lung cancer, head and neck cancer or prostate cancer in a patient comprising administering a therapeutically effective amount of a compound comprising arginine deiminase covalently bonded via a linking group to polyethylene glycol, in combination with docetaxel. In one embodiment, the arginine deiminase is covalently bonded to 5±1.5 straight chain PEG molecules and the compound is formulated in a composition comprising less than about 0.5% native ADI, less than about 5% free PEG, or both; wherein the arginine deiminase is administered weekly at a dose of about 160 IU/m2 to about 640 IU/m2; and wherein the non-small cell lung cancer, head and neck cancer or prostate cancer exhibits reduced expression of ASS.

Another aspect of the present disclosure provides a method of treating renal cell carcinoma in a patient comprising administering a therapeutically effective amount of a compound comprising arginine deiminase covalently bonded via a linking group to polyethylene glycol, in combination with rapamycin. In one embodiment, the arginine deiminase is covalently bonded to 5±1.5 straight chain PEG molecules and the compound is formulated in a composition comprising less than about 0.5% native ADI, less than about 5% free PEG, or both; wherein the arginine deiminase is administered weekly at a dose of about 160 IU/m2 to about 640 IU/m2; and wherein the cancer exhibits reduced expression of ASS.

In certain embodiments of the present invention the ADI is covalently bonded to more than one polyethylene glycol molecule, or to about 9 to about 12 polyethylene glycol molecules. In another embodiment of the present invention the polyethylene glycol has a total weight average molecular weight of from about 1,000 to about 40,000, has a total weight average molecular weight of from about 10,000 to about 30,000, and in certain embodiments, the polyethylene glycol has a molecular weight of 20,000.

In certain embodiments of the present disclosure the linking group is a succinimide group. In certain embodiments, the succinimide group may be succinimidyl succinate, succinimidyl propionate, succinimidyl carboxymethylate, succinimidyl succinamide, N-hydroxy succinimide or combinations thereof. In one embodiment, the succinimide group is succinimidyl succinate, succinimidyl propionate or combinations thereof.

In certain embodiments of the present disclosure the ADI is not isolated from *Mycoplasma arginini*. In other embodiments, the ADI is isolated from *Mycoplasma hominis*. In one particular embodiment, the ADI has been modified to be free of at least one lysine at position 112, 374, 405 or 408 of SEQ ID NO:1, and in another embodiment, the ADI comprises the amino acid sequence set forth in SEQ ID NO: 2. In one embodiment, the arginine deiminase is covalently bonded to 5±1.5 PEG molecules, and in certain embodiments the PEG is straight chain PEG.

In some embodiments of the present methods, the ADI is administered from about twice a week to about once every 2 weeks, and in a particular embodiment the ADI is administered weekly.

In one embodiment, the ADI is administered at a dose of between about 80 IU/m$^2$ and about 640 IU/m$^2$, and in one particular embodiment is administered at a dose of about 160 IU/m$^2$. In another embodiment, the ADI is administered weekly at a dose of about 160 IU/m$^2$.

In one embodiment, the compound used in the methods described herein comprising arginine deiminase covalently bonded via a linking group to polyethylene glycol, is formulated in a composition comprising less than about 0.5% native ADI, less than about 5% free PEG, or both.

Another aspect of the present invention provides a method of treating GVHD in a patient comprising administering to the patient a compound comprising ADI covalently bonded via a linking group to polyethylene glycol.

A further aspect of the present invention provides a method of treating a cancer in a patient comprising administering to the patient a compound comprising ADI covalently bonded via a linking group to polyethylene glycol, wherein the cancer exhibits of ASS. In one embodiment, the cancer is selected from the group consisting of leukemia, acute myeloid leukemia, relapsed acute myeloid leukemia, breast cancer, ovarian cancer, colorectal cancer, gastric cancer, glioma, glioblastoma multiforme, non-small cell lung cancer (NSCLC), kidney cancer, bladder cancer, uterine cancer, esophageal cancer, brain cancer, head and neck cancers, cervical cancer, testicular cancer, and stomach cancer. In a further embodiment, the reduced expression of ASS results from methylation of the argininosuccinate synthetase promoter. In another embodiment, the reduced expression of ASS results from a DNA mutation or deletion. In one particular embodiment, reduced expression of ASS results from deletion or transposition of the 9q34 locus as part of the "Philadelphia chromosome". In certain embodiments, the cancer exhibits reduced expression of ASS.

Yet a further aspect of the present invention provides a method of treating a cancer in a patient comprising administering to the patient a compound comprising ADI covalently bonded via a linking group to polyethylene glycol, wherein the cancer exhibits reduced expression of argininosuccinate lyase. In one embodiment, the cancer is selected from the group consisting of leukemia, acute myeloid leukemia, relapsed acute myeloid leukemia, breast cancer, ovarian cancer, colorectal cancer, gastric cancer, glioma, glioblastoma multiforme, non-small cell lung cancer (NSCLC), kidney cancer, bladder cancer, uterine cancer, esophageal cancer, brain cancer, head and neck cancers, cervical cancer, testicular cancer, and stomach cancer. In one embodiment, reduced expression of ASL results from methylation of the argininosuccinate lyase promoter. In certain embodiments, the reduced expression of ASL results from a DNA mutation or deletion. In one particular embodiment, the cancer is ASL negative.

In certain embodiments of the present invention, the treatment with ADI-PEG inhibits NO synthesis, inhibits angiogenesis, induces apoptosis in tumor cells, or a combination thereof, in vivo. In certain embodiments the treatment results in stable disease. In other embodiments, the treatment increases progression free survival time in the patient. In yet another embodiment, plasma arginine is depleted for at least one month, or for more than 2 months.

In certain embodiments, the methods described herein further comprise administration of a therapeutic agent, such as a chemotherapeutic agent including but not limited to cyclophosphamide, gemcitabine, cisplatin, sorafenib, sunitinib and everolimus. In certain embodiments, the ADI and the chemotherapeutic agent act additively or synergistically.

In some embodiments, the leukemia is acute myeloid leukemia. In some embodiments, the leukemia is relapsed acute myeloid leukemia. In some embodiments, the leukemia is not lymphocytic leukemia or chronic myelogenous leukemia. A compound comprising arginine deiminase covalently bonded via a linking group to polyethylene glycol, in combination with an autophagy inhibitor, for use in treating a cancer in a patient, wherein the cancer is pancreatic cancer, a sarcoma, or small cell lung cancer. In some embodiments, the autophagy inhibitor is selected from the group consisting of chloroquine, 3-methyladenine, hydroxychloroquine, bafilomycin A1, 5-amino-4-imidazole carboxamide riboside (AICAR), okadaic acid, N6-mercaptopurine riboside, wortmannin, and vinblastine.

A compound comprising arginine deiminase covalently bonded via a linking group to polyethylene glycol, for treating a cancer in a patient, wherein the cancer is selected from the group consisting of breast cancer, ovarian cancer, colorectal cancer, gastric cancer, glioma, glioblastoma multiforme, non-small cell lung cancer (NSCLC), kidney cancer, bladder cancer, uterine cancer, esophageal cancer, brain cancer, head and neck cancers, cervical cancer, testicular cancer, and stomach cancer.

A compound comprising arginine deiminase covalently bonded via a linking group to polyethylene glycol, for treating a cancer in a patient, wherein the cancer is not melanoma, pancreatic cancer, prostate cancer, small cell lung cancer, mesothelioma, lymphocytic leukemia, chronic myelogenous leukemia, lymphoma, hepatoma, or sarcoma.

A compound comprising arginine deiminase covalently bonded via a linking group to polyethylene glycol, in combination with cisplatin, for treating melanoma in a patient.

A compound comprising arginine deiminase covalently bonded via a linking group to polyethylene glycol, in combination with docetaxel, for treating non-small cell lung cancer, head and neck cancer or prostate cancer in a patient.

A compound comprising arginine deiminase covalently bonded via a linking group to polyethylene glycol, in combination with rapamycin, for treating renal cell carcinoma in a patient.

In some embodiments, the arginine deiminase is covalently bonded to more than one polyethylene glycol molecule. In some embodiments, the arginine deiminase is covalently bonded to about 9 to about 12 polyethylene glycol molecules. In some embodiments, the arginine deiminase is covalently bonded to 5±1.5 PEG molecules. In some embodiments, the PEG molecules are straight chain PEG molecules. In some embodiments, the polyethylene glycol has a total weight average molecular weight of from about 1,000 to about 40,000. In some embodiments, the polyethylene glycol has a total weight average molecular weight of from about 10,000 to about 30,000. In some embodiments, the polyethylene glycol has a molecular weight of 20,000. In some embodiments, the polyethylene glycol is straight chain polyethylene glycol. In some embodiments, the linking group is a succinimide group. In some embodiments, the succinimide group is succinimidyl succinate, succinimidyl propionate, succinimidyl carboxymethylate, succinimidyl succinamide, N-hydroxy succinimide or combinations thereof. In some embodiments, the succinimide group is succinimidyl succinate, succinimidyl propionate or combinations thereof. In some embodiments, the arginine deiminase is not isolated from *Mycoplasma arginini*. In some embodiments, the arginine deiminase is isolated from *Mycoplasma hominis*. In some embodiments, the arginine deiminase has been modified to be free of at least one lysine at position 112, 374, 405 or 408 of SEQ ID NO:1. In some embodiments, the compound is formulated in a composition comprising less than about 0.5% native ADI, less than about 5% free PEG, or both. In some embodiments, the arginine deiminase comprises the amino acid sequence set forth in SEQ ID NO: 2. In some embodiments, the arginine deiminase is administered from about twice a week to about once every 2 weeks. In some embodiments, the arginine deiminase is administered weekly. In some embodiments, the arginine deiminase is administered at a dose of between about 80 IU/m$^2$ and about 650 IU/m$^2$. In some embodiments, the arginine deiminase is administered at a dose of about 160 IU/m$^2$. In some embodiments, the arginine deiminase is administered weekly at a dose of about 160 IU/m$^2$.

A compound comprising arginine deiminase covalently bonded via a linking group to polyethylene glycol, for treating GVHD in a patient. A compound comprising arginine deiminase covalently bonded via a linking group to polyethylene glycol, for treating a cancer in a patient, wherein the cancer exhibits reduced expression of argininosuccinate synthetase.

In some embodiments, the cancer is selected from the group consisting of leukemia, acute myeloid leukemia, relapsed acute myeloid leukemia, breast cancer, ovarian cancer, colorectal cancer, gastric cancer, glioma, glioblastoma multiforme, non-small cell lung cancer (NSCLC), kidney cancer, bladder cancer, uterine cancer, esophageal cancer, brain cancer, head and neck cancers, cervical cancer, testicular cancer, and stomach cancer. In some embodiments, the reduced expression of argininosuccinate synthetase results from methylation of the argininosuccinate synthetase promoter. In some embodiments, the reduced expression of argininosuccinate synthetase results from a DNA mutation or deletion. In some embodiments, the cancer is argininosuccinate synthetase negative.

A compound comprising arginine deiminase covalently bonded via a linking group to polyethylene glycol, for treating a cancer in a patient, wherein the cancer exhibits reduced expression of argininosuccinate lyase. In some embodiments, the cancer is selected from the group consisting of leukemia, acute myeloid leukemia, relapsed acute myeloid leukemia, breast cancer, ovarian cancer, colorectal cancer, gastric cancer, glioma, glioblastoma multiforme, non-small cell lung cancer (NSCLC), kidney cancer, bladder cancer, uterine cancer, esophageal cancer, brain cancer, head and neck cancers, cervical cancer, testicular cancer, and stomach cancer. In some embodiments, the reduced expression of argininosuccinate lyase results from methylation of the argininosuccinate lyase promoter. In some embodiments, the reduced expression of argininosuccinate lyase results from a DNA mutation or deletion. In some embodiments, the cancer is argininosuccinate lyase negative.

In some embodiments, the treatment inhibits NO synthesis, inhibits angiogenesis, induces apoptosis in tumor cells, or a combination thereof, in vivo. In some embodiments, the treatment results in stable disease. In some embodiments, the treatment increases progression free survival time in the patient. In some embodiments, plasma arginine is depleted for at least one month. In some embodiments, plasma arginine is depleted for more than 2 months. In some embodiments, the arginine deiminase and the autophagy inhibitor act synergistically. Some embodiments further comprise administration of a chemotherapeutic agent. In some embodiments, the chemotherapeutic agent is selected from the group consisting of cyclophosphamide, gemcitabine, cisplatin, sorafenib, sunitinib and everolimus.

In some embodiments, wherein arginine deiminase is covalently bonded to 5±1.5 straight chain PEG molecules and the compound is formulated in a composition comprising less than about 0.5% native ADI, less than about 5% free PEG, or both; wherein the arginine deiminase is administered weekly at a dose of about 160 IU/m$^2$ to about 640 IU/m$^2$; and wherein the cancer exhibits reduced expression of ASS.

BRIEF DESCRIPTION OF THE SEQUENCES

SEQ ID NO:1 is the amino acid sequence of the wild type *M. hominis* ADI protein.

SEQ ID NO:2 is the amino acid sequence of a modified *M. hominis* ADI protein.

SEQ ID NO:3 and 4 are PCR primers used to amplify argininosuccinate synthetase cDNA.

BRIEF DESCRIPTION OF THE DRAWINGS

FIG. 2A is a bar graph showing the percentage of cells undergoing cell death following incubation with a pan-caspase inhibitor ZVAD-fmk ("Zvad") and/or ADI-PEG. FIG. 2B is a bar graph that shows the percentage of Annexin V positive cells following a 72 hour incubation with ADI-PEG in comparison to a PBS control.

FIGS. 7A-7E show the expression of ASS in small cell lung cancer human tumors and cell lines. Anti-ASS antibody 195-21-1 was used to detect ASS protein expression in normal skin (FIG. 7A), colon carcinoma (FIG. 7B), and small cell lung cancer (FIG. 7C). FIG. 7D shows expression of ASS protein in a panel of small cell lung cancer cell lines compared with positive control SW1222 colon cancer cells by western blot. FIG. 7E shows the correlation of ASS protein expression as measured by western blot with mRNA expression determined by qRT-PCR.

FIGS. 9A-9F show that ADI induces apoptosis and autophagy in ASS-negative SK-LC-13 small cell lung cancer cells. For fluorescence-activated cell sorting analysis of sub-$G_1$ DNA content demonstrating apoptosis, cells were incubated in control media (FIG. 9A), 25 nM topotecan (FIG. 9B), 1.0 mIU ml$^{-1}$ ADI-PEG 20 (FIG. 9C), and 10 mIU ml$^{-1}$ ADI-PEG 20 (FIG. 9D) for 72 hours before DNA staining with propidium iodide (P1). FIG. 9E shows LC3-I and LC3-II protein level following 24 hour incubation with ADI-PEG 20 or chloroquine ("CQ")-positive control. FIG. 9F shows active caspase 3 detected by western blot in SK-LC-13 cells (FIG. 9F).

FIG. 10A shows relative expression of ASS mRNA expression determined by RT-PCR in SW1222 cells treated with ASS siRNA. FIG. 10B shows relative expression of ASS protein assessed by western blot in SW1222 cells treated with ASS siRNA. FIG. 10C shows the proliferation of ADI-PEG 20 treated cells as measured by the MTS proliferation assay.

FIGS. 11A-11G show the inhibition of the growth of moderately sized SK-LC-13 small cell lung cancer xenografts in BALB/c-nude mice by ADI formulated with PEG of 20,000 m.w. (ADI-PEG 20). Growth curves of tumor volumes from mice receiving PBS vehicle (filled circle), a short 20 day course (dosing every 5 days) of ADI-PEG 20 (filled square), or continued dosing (every 5 days until group termination) of ADI-PEG 20 (open square) at doses of 1 IU per mouse (FIG. 11A), 2 IU per mouse (FIG. 11B), and 5 IU per mouse (FIG. 11C) are shown. Tumor volumes at termination of the control group on day 33 are shown in FIG. 11D. Serum levels of ADI-PEG 20 (FIG. 11E), arginine (FIG. 11F), and citrulline (FIG. 11G) are shown for days 0, 12, and 40 of the study. Values are the same in short and extended dosing cohorts at day 0 and 12, as extended dosing was only initiated at day 20.

DETAILED DESCRIPTION

The present invention relates generally to methods of treating cancer with ADI, and in particular ADI-PEG.

Figure 1:
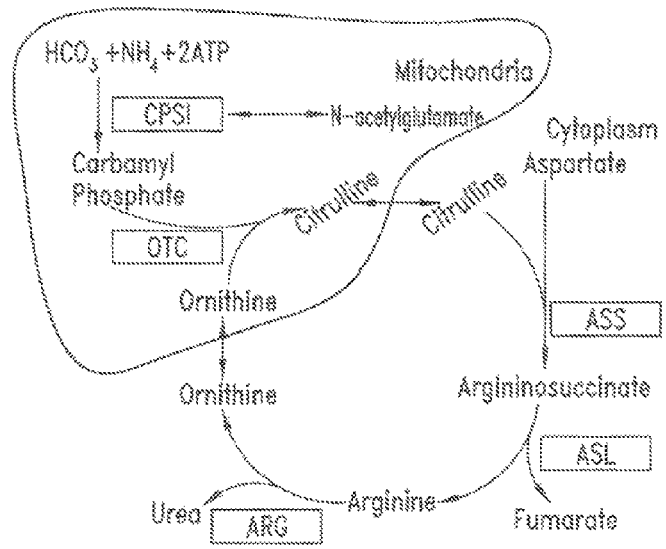
FIG. 1 is a diagram of arginine metabolism through the Krebs (urea) cycle.

Normal cells do not require arginine for growth, since they can synthesize arginine from citrulline in a two step process catalyzed by ASS and ASL (see FIG. 1). In contrast, certain cancers do not express ASS. Certain cancers do not express ASL, and other cancers may have diminished expression of, or may not express ASS and/or ASL. Therefore, these cancers are auxotrophic for arginine. This metabolic difference may be capitalized upon to develop a safe and effective therapy to treat these forms of cancer. ADI catalyzes the conversion of arginine to citrulline via the arginine dihydrolase pathway, and may thus be used to eliminate arginine.

The practice of the present invention will employ, unless indicated specifically to the contrary, conventional methods of virology, immunology, microbiology, molecular biology and recombinant DNA techniques within the skill of the art, many of which are described below for the purpose of illustration. Such techniques are explained fully in the literature. See, e.g., *Current Protocols in Protein Science, Current Protocols in Molecular Biology* or *Current Protocols in Immunology*, John Wiley & Sons, New York, N.Y. (2009); Ausubel et al., *Short Protocols in Molecular Biology*, 3$^{rd}$ ed., Wiley & Sons, 1995; Sambrook and Russell, *Molecular Cloning: A Laboratory Manual* (3rd Edition, 2001); Maniatis et al. *Molecular Cloning: A Laboratory Manual* (1982); *DNA Cloning: A Practical Approach*, vol. I & II (D. Glover, ed.); *Oligonucleotide Synthesis* (N. Gait, ed., 1984); *Nucleic Acid Hybridization* (B. Hames & S. Higgins, eds., 1985); *Transcription and Translation* (B. Hames & S. Higgins, eds., 1984); *Animal Cell Culture* (R. Freshney, ed., 1986); Perbal, *A Practical Guide to Molecular Cloning* (1984) and other like references.

As used in this specification and the appended claims, the singular forms "a," "an" and "the" include plural references unless the content clearly dictates otherwise.

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

Each embodiment in this specification is to be applied mutatis mutandis to every other embodiment unless expressly stated otherwise.

Standard techniques may be used for recombinant DNA, oligonucleotide synthesis, and tissue culture and transformation (e.g., electroporation, lipofection). Enzymatic reactions and purification techniques may be performed according to manufacturer's specifications or as commonly accomplished in the art or as described herein. These and related techniques and procedures may be generally performed according to conventional methods well known in the art and as described in various general and more specific references that are cited and discussed throughout the present specification. Unless specific definitions are provided, the nomenclature utilized in connection with, and the laboratory procedures and techniques of, molecular biology, analytical chemistry, synthetic organic chemistry, and medicinal and pharmaceutical chemistry described herein are those well known and commonly used in the art. Standard techniques may be used for recombinant technology, molecular biological, microbiological, chemical syntheses, chemical analyses, pharmaceutical preparation, formulation, and delivery, and treatment of patients.

"Patient" refers to an animal, in certain embodiments a mammal, and in a specific embodiment, a human.

"Biocompatible" refers to materials or compounds which are generally not injurious to biological functions and which will not result in any degree of unacceptable toxicity, including allergenic and disease states.

Throughout the present disclosure, the following abbreviations may be used: PEG, polyethylene glycol; ADI, arginine deiminase; SS, succinimidyl succinate; SSA, succinimidyl succinamide; SPA, succinimidyl propionate; NHS, N-hydroxy-succinimide; ASS1 or ASS, argininosuccinate synthetase; ASL, argininosuccinate lyase.

In the present invention, the ADI gene may be derived, cloned or produced from any source, including, for example, microorganisms, recombinant biotechnology or any combination thereof. For example, arginine deiminase may be cloned from microorganisms of the genera *Mycoplasma, Clostridium, Bacillus, Borrelia, Enterococcus, Streptococcus, Lactobacillus, Giardia*. In certain embodiments, arginine deiminase is cloned from *Mycoplasma pneumoniae, Mycoplasma hominis, Mycoplasma arginini, Steptococcus pyogenes, Steptococcus pneumoniae, Borrelia burgdorferi, Borrelia afzelii, Giardia intestinalis, Clostridium perfringens, Bacillus licheniformis, Enterococcus faecalis, Lactobacillus sake*, or any combination thereof. In particular, the ADI used in the present invention may comprise the amino acid sequence of SEQ ID NO: 1 or 2, or a variant thereof having ADI activity (e.g., able to metabolize arginine into citrulline and ammonia) or a fragment thereof having ADI activity.

In certain embodiments of the present invention, the ADI is cloned from microorganisms of the genus *Mycoplasma*. In further embodiments, the ADI is cloned from *Mycoplasma*

*hominis, Mycoplasma arthritides*, or any combination thereof and is not derived from *Mycoplasma arginini*. In particular, the ADI used in the present invention may have the amino acid sequence set forth in SEQ ID NO: 1 or 2, or a variant thereof having ADI activity (e.g., able to metabolize arginine into citrulline and ammonia) or a fragment thereof having ADI activity.

Native ADI may be found in microorganisms and is antigenic and rapidly cleared from circulation in a patient. These problems may be overcome by modifying ADI. Thus, the present disclosure provides ADI modified by a modifying agent, including, but not limited to macromolecule polymers, proteins, peptides, polysaccharides, or other compounds. Arginine deiminase and the modifying agent may be linked by either covalent bonds or non-covalent interaction to form a stable conjugate or a stable composition to achieve a desired effect. In certain embodiments, the modified ADI retains the biological activity of ADI and has a longer half life in vivo and lower antigenicity than the unmodified ADI. In certain embodiments, the modified ADI retains at least 70%, 75%, 80%, 85%, 90%, 95%, 96%, 97%, 98%, 99% or more of the biological activity of unmodified ADI.

In one embodiment, a modifying agent can be a polymer or a protein or a fragment thereof that is biocompatible and can increase the half life of ADI in blood. The modifying agent can be either chemically coupled to ADI or where applicable, linked to the ADI via fusion protein expression.

Macromolecule polymers may include a non-peptide macromolecule polymer, which in certain embodiments, may have its own bioactivity. Suitable polymers include, but are not limited to, polyenol compounds, polyether compounds, polyvinylpyrrolidone, poly amino acids, copolymer of divinyl ether and maleic anhydride, N-(2-hydroxypropyl)-methacrylamide, polysaccharide, polyoxyethylated polyol, heparin or its fragment, poly-alkyl-ethylene glycol and its derivatives, copolymers of poly-alkyl-ethylene glycol and its derivatives, poly(vinyl ethyl ether), a,P-Poly[(2-hydroxyethyl)-DL-aspartamide], polycarboxylates, poly oxyethylene-oxymethylenes, polyacryloyl morpholines, copolymer of amino compounds and oxyolefin, poly hyaluronic acid, polyoxiranes, copolymer of ethanedioic acid and malonic acid, poly (1,3-dioxolane), ethylene and maleic hydrazide copolymer, poly sialic acid, cyclodextrin, etc. In certain embodiments, the polymer is polyethylene glycol.

The polyenol compounds as used herein include, but are not limited to, polyethylene glycol (including monomethoxy polyethylene glycol, monohydroxyl polyethylene glycol), polyvinyl alcohol, polyallyl alcohol, polybutenol and the like, and their derivatives, such as lipids.

The polyether compounds include, but are not limited to poly alkylene glycol $(HO((CH2)_xO)_nH)$, polypropylene glycol, polyoxyrehylene $(HO((CH_2)_2O)_nH)$, polyvinyl alcohol $((CH_2CHOH)_n)$.

Poly amino acids include, but are not limited to, polymers of one type of amino acid or copolymers of two or more types of amino acids, for example, polyalanine or polylysine, or block co-polymers thereof.

Polysaccharides include but are not limited to, glucosan and its derivatives, for example dextran sulfate, cellulose and its derivatives (including methyl cellulose and carboxymethyl cellulose), starch and its derivatives, polysucrose, etc.

In one specific embodiment of the present invention, ADI is modified by coupling with proteins or peptides, wherein one or more proteins or peptides are directly or indirectly linked to ADI. The proteins can either be naturally existing proteins or their fragments, including but not limited to naturally existing human serum proteins or their fragments, such as thyroxine-binding protein, transthyretin, a1-acid glycoprotein, transferrin, fibrinogen, immunoglobulin, Ig Fc reguis, albumin, and fragments thereof. By "fragment" is meant any portion of a protein that is smaller than the whole protein but which retains the desired function of the protein. ADI may be directly or indirectly linked to a protein via a covalent bond. Direct linking means that one amino acid of ADI is directly linked to one amino acid of the modifying protein, via a peptide bond or a disulfide bridge. Indirect linking refers to the linkages between ADI and a modifying protein, via originally existing chemical groups therebetween or specific chemical groups added through biological or chemical means, or the combination of the above-mentioned linkages.

In one particular embodiment, ADI is modified by covalent attachment with PEG. ADI covalently modified with PEG (with or without a linking group) may be hereinafter referred to as "ADI-PEG." When compared to native ADI, ADI-PEG retains most of its enzymatic activity, is far less antigenic, has a greatly extended circulating half-life, and is much more efficacious in the treatment of tumors.

"Polyethylene glycol" or "PEG" refers to mixtures of condensation polymers of ethylene oxide and water, in a branched or straight chain, represented by the general formula $H(OCH_2CH_2)nOH$, wherein n is at least 4. "Polyethylene glycol" or "PEG" is used in combination with a numeric suffix to indicate the approximate weight average molecular weight thereof. For example, PEG5,000 refers to PEG having a total weight average molecular weight of about 5,000; PEG12,000 refers to PEG having a total weight average molecular weight of about 12,000; and PEG20,000 refers to PEG having a total weight average molecular weight of about 20,000.

In one embodiment of the present invention, the PEG has a total weight average molecular weight of about 1,000 to about 50,000; in one embodiment from about 3,000 to about 40,000, and in another embodiment from about 5,000 to about 30,000; in certain embodiments from about 8,000 to about 30,000; in other embodiments from about 11,000 to about 30,000; in additional embodiments, from about 12,000 to about 28,000; in still other embodiments, from about 16,000 to about 24,000; and in other embodiments, about 18,000 to about 22,000; in another embodiment, from 19,000 to about 21,000, and in one embodiment, the PEG has a total weight average molecular weight of about 20,000. Generally, PEG with a molecular weight of 30,000 or more is difficult to dissolve, and yields of the formulated product are greatly reduced. The PEG may be a branched or straight chain, or in certain embodiments, a straight chain. Generally, increasing the molecular weight of the PEG decreases the immunogenicity of the ADI. The PEG having a molecular weight described in this embodiment may be used in conjunction with ADI, and, optionally, a biocompatible linking group, to treat cancer, including, for example, acute myeloid leukemia, such as relapsed acute myeloid leukemia, breast cancer, ovarian cancer, colorectal cancer, gastric cancer, glioma, glioblastoma multiforme, non-small cell lung cancer (NSCLC), kidney cancer, bladder cancer, uterine cancer, esophageal cancer, brain cancer, head and neck cancers, cervical cancer, testicular cancer, stomach cancer and esophageal cancer.

In another embodiment of the present invention, the PEG has a total weight average molecular weight of about 1,000 to about 50,000; in certain embodiments about 3,000 to about 30,000; in other embodiments from about 3,000 to about 20,000; in one embodiment from about 4,000 to about 12,000; in still other embodiments from about 4,000 to about 10,000; in additional embodiments from about 4,000 to about 8,000; still further embodiments from about 4,000 to about 6,000; and about 5,000 in another embodiment. The PEG may be a branched or straight chain, and in certain embodiments is a straight chain. The PEG having a molecular weight described in this embodiment may be used in conjunction with ADI, and optionally, a biocompatible linking group, to treat graft versus host disease (GVHD) or cancer.

While ADI-PEG is the illustrative modified ADI described herein, as would be recognized by the skilled person ADI may be modified with other polymers or appropriate molecules for the desired effect, in particular reducing immunogenicity and increasing serum half-life.

ADI may be covalently bonded to a modifying agent, such as PEG, with or without a linking group, although a preferred embodiment utilizes a linking group.

The linking group used to covalently attach ADI to a modifying agent, e.g. PEG, may be any biocompatible linking group. As discussed above, "biocompatible" indicates that the compound or group is non-toxic and may be utilized in vitro or in vivo without causing injury, sickness, disease or death. A modifying agent, such as PEG, can be bonded to the linking group, for example, via an ether bond, an ester bond, a thiol bond or an amide bond. Suitable biocompatible linking groups include, for example, an ester group, an amide group, an imide group, a carbamate group, a carboxyl group, a hydroxyl group, a carbohydrate, a succinimide group (including, for example, succinimidyl succinate (SS), succinimidyl propionate (SPA), succinimidyl carboxymethylate (SCM), succinimidyl succinamide (SSA) or N-hydroxy succinimide (NHS)), an epoxide group, an oxycarbonylimidazole group (including, for example, carbonyldimidazole (CDI)), a nitro phenyl group (including, for example, nitrophenyl carbonate (NPC) or trichlorophenyl carbonate (TPC)), a trysylate group, an aldehyde group, an isocyanate group, a vinylsulfone group, a tyrosine group, a cysteine group, a histidine group or a primary amine. In one embodiment, the biocompatible linking group is an ester group and/or a succinimide group. In another embodiment, the linking group is SS, SPA, SCM, SSA or NHS; in certain embodiments, SS, SPA or NHS are more preferred, and in other embodiments, SS or SPA being most preferred.

Alternatively, ADI may be coupled directly to a modifying agent, such as PEG (i.e., without a linking group) through an amino group, a sulfhydral group, a hydroxyl group or a carboxyl group.

ADI may be covalently bonded to PEG, via a biocompatible linking group, using methods known in the art, as described, for example, by Park et al, Anticancer Res., 1:373-376 (1981); and Zaplipsky and Lee, Polyethylene Glycol Chemistry: Biotechnical and Biomedical Applications, J. M. Harris, ed., Plenum Press, NY, Chapter 21 (1992), the disclosures of which are hereby incorporated by reference herein in their entirety.

The attachment of PEG to ADI increases the circulating half-life of ADI. Generally, PEG is attached to a primary amine of ADI. Selection of the attachment site of PEG, or other modifying agent, on the ADI is determined by the role of each of the sites within the active domain of the protein, as would be known to the skilled artisan. PEG may be attached to the primary amines of ADI without substantial loss of enzymatic activity. For example, ADI cloned from *Mycoplasma arginini, Mycoplasma arthritides* and *Mycoplasma hominis* has about 17 lysines that may be modified by this procedure. In other words, the 17 lysines are all possible points at which ADI can be attached to PEG via a biocompatible linking group, such as SS, SPA, SCM, SSA and/or NHS. PEG may also be attached to other sites on ADI, as would be apparent to one skilled in the art in view of the present disclosure.

From 1 to about 30 PEG molecules may be covalently bonded to ADI. In certain embodiments, ADI is modified with one PEG molecule. In other embodiments, ADI is modified with more than one PEG molecule. In one embodiment, ADI is modified with about 7 to about 15 PEG molecules, in one embodiment from about 9 to about 12 PEG molecules. In another embodiment, the ADI is modified with 2, 3, 4, 5, 6, 7, 8, 9, 10, 11, or 12 PEG molecules. In one specific embodiment, ADI is modified with 4.5-5.5 PEG molecules per ADI. In another embodiment, ADI is modified with 5±1.5 PEG molecules.

In another embodiment, about 30% to about 70% of the primary amino groups in ADI are modified with PEG, in one embodiment about 40% to about 60%, or in certain embodiments about 45% to about 55%, and in other embodiments about 50% of the primary amino groups in arginine deiminase are modified with PEG. When PEG is covalently bonded to the end terminus of ADI, it may be desirable to have only 1 PEG molecule utilized. Increasing the number of PEG units on ADI increases the circulating half life of the enzyme. However, increasing the number of PEG units on ADI decreases the specific activity of the enzyme. Thus, a balance needs to be achieved between the two, as would be apparent to one skilled in the art in view of the present disclosure.

In the present invention, a common feature of biocompatible linking groups is that they attach to a primary amine of arginine deiminase via a maleimide group. Once coupled with ADI, SS-PEG has an ester linkage next to the PEG, which may render this site sensitive to serum esterase, which may release PEG from ADI in the body. SPA-PEG and PEG2-NHS do not have an ester linkage, so they are not sensitive to serum esterase.

In the present invention, the particular linking groups do not appear to influence the circulating half-life of ADI-PEG or its specific enzyme activity. However, in certain embodiments, a biocompatible linking group is used in the present invention. PEG which is attached to the protein may be either a straight chain, as with SS-PEG, SPA-PEG and SC-PEG, or a branched chain of PEG may be used, as with PEG2-NHS.

In certain embodiments, the ADI of the present disclosure may be modified as described in U.S. Pat. No. 6,635,462. In particular, modifications of one or more of the naturally occurring amino acid residues of ADI, in particular from *Mycoplasma hominis*, can provide for an enzyme that is more easily renatured and formulated thereby improving existing techniques for the manufacture of ADI and therapeutic compositions comprising the same. In one embodiment, the ADI of the present disclosure is modified to remove one or more lysine residues (e.g., the lysine can be substituted with another amino acid). In particular, in one embodiment, the ADI is modified to be free of the lysine at position 112, 374, 405 or 408 of SEQ ID NO:1.

In certain embodiments, pegylation sites associated with ADI located at or adjacent to the catalytic region of the enzyme are modified. For purposes of the present invention, the phrase "pegylation site" may be defined as any site or position of ADI that may be covalently modified with polyethylene glycol. A "pegylation site" can be considered located at or adjacent the catalytic region of the enzyme where pegylation of the site results in a significant reduction in catalytic activity of the enzyme. The pegylation of such sites has traditionally resulted in the inactivation of the enzyme. For example, ADI from *Mycoplasma hominis* has a lysine at the 112 position which can be considered to be at or adjacent the catalytic region of the enzyme. The attachment of PEG to this lysine at the 112 position can inactivate the enzyme. In addition, ADI from *Mycoplasma hominis* has a cysteine at the 397 position which can be considered to be at or adjacent the catalytic region of the enzyme. The amino acid substitutions for cysteine at the 397 position can inactivate the enzyme. In particular, substituting alanine, histidine, arginine, serine, lysine or tyrosine for cysteine at the 397 position can result in a loss of all detectable enzyme activity. ADI from *Mycoplasma hominis* also has three lysines located near this conserved cysteine, in particular Lys374, Lys405 and Lys408. The attachment of PEG to Lys374, Lys405, Lys408 or combinations thereof can inactivate the enzyme.

It is to be understood that ADI derived from other organisms may also have pegylation sites corresponding to 112 position of ADI from *Mycoplasma hominis*. For example, ADI from *Steptococcus pyrogenes* has lysine at the 104 position, ADI from *Mycoplasma pneumoniae* has lysine at the 106 position, and ADI from *Giardia intestinalis* has lysine at the 114 position. In addition, ADI from some organisms may have lysines corresponding to the same general location as the 112 position of ADI from *Mycoplasma hominis*. The location of lysine in ADI from such organisms are known to the skilled person and are described in U.S. Pat. No. 6,635,462.

Thus, in one embodiment, the present invention provides for certain amino acid substitutions in the polypeptide chain of ADI. These amino acid substitutions provide for modified ADI that loses less activity upon modified by a modifying agent, e.g., upon pegylation. By eliminating pegylation sites, or other known modification sites, at or adjacent to the catalytic region of enzyme, optimal modification, e.g., pegylation, can be achieved without the loss of activity.

It is to be understood that other embodiments of the invention are based on the understanding that certain structural characteristics of arginine deiminase may prevent or interfere with the proper and rapid renaturation of arginine deiminase when produced via recombinant technology. In particular, these structural characteristics hinder or prevent the enzyme from assuming an active conformation during recombinant production. For purposes of the present invention, the phrase "active conformation" may be defined as a three-dimensional structure that allows for enzymatic activity by unmodified or modified arginine deiminase. The active conformation may, in particular, be necessary for catalyzing the conversion of arginine into citrulline. The phrase "structural characteristic" may be defined as any trait, quality or property of the polypeptide chain resulting from a particular amino acid or combination of amino acids. For instance, arginine deiminase may contain an amino acid that results in a bend or kink in the normal peptide chain and thus hinders the enzyme from assuming an active conformation during renaturation of the enzyme. In particular, arginine deiminase from *Mycoplasma hominis* has a proline at the 210 position that may result in a bend or kink in the peptide chain, making it more difficult to renature the enzyme during recombinant production. It is to be understood that arginine deiminase derived from other organisms may also have sites corresponding to the 210 position of arginine deiminase from *Mycoplasma hominis*.

The present invention thus again provides for certain amino acid substitutions in the polypeptide chain of arginine deiminase. Such amino acid substitutions can eliminate the problematic structural characteristics in the peptide chain of arginine deiminase. Such amino acid substitutions provide for improved renaturation of the modified arginine deiminase. These amino acid substitutions make possible rapid renaturing of modified arginine deiminase using reduced amounts of buffer. These amino acid substitutions may also provide for increased yields of renatured modified arginine deiminase. In one embodiment of the invention, the modified arginine deiminase has a single amino acid substitution at P210. As mentioned above, arginine deiminase derived from *Mycoplasma hominis* has the amino acid proline located at the 210 position. While not limiting the present invention, it is presently believed that the presence of the amino acid proline at position 210 results in a bend or kink in the normal polypeptide chain that increases the difficulty of renaturing (i.e., refolding) arginine deiminase. Substitutions for proline at position 210 make possible the rapid renaturation of modified arginine deiminase using reduced amounts of buffer. Substitutions for proline at position 210 may also provide for increased yields of renatured modified arginine deiminase. In a preferred embodiment, the proline at position 210 is substituted with serine. It is to be understood that in accordance with this aspect of the invention, other substitutions at position 210 may be made. Examples of other substitutions include Pro210 to Thr210, Pro210 to Arg210, Pro210 to Asn210, Pro210 to Gln210 or Pro210 to Met210. By eliminating those structural characteristics associated with the amino acid of position 210 of the wild-type arginine deiminase, proper refolding of the enzyme can be achieved.

The methods of the present invention can involve either in vitro or in vivo applications. In the case of in vitro applications, including cell culture applications, the compounds described herein can be added to the cells in cultures and then incubated. The compounds of the present invention may also be used to facilitate the production of monoclonal and/or polyclonal antibodies, using antibody production techniques well known in the art. The monoclonal and/or polyclonal antibodies can then be used in a wide variety of diagnostic applications, as would be apparent to one skilled in the art.

The in vivo means of administration of the compounds of the present invention will vary depending upon the intended application. Administration of the ADI compositions described herein, in pure form or in an appropriate pharmaceutical composition, can be carried out via any of the accepted modes of administration of agents for serving similar utilities. The pharmaceutical compositions can be prepared by combining ADI, e.g. ADI-PEG, ADI-PEG 20, with an appropriate physiologically acceptable carrier, diluent or excipient, and may be formulated into preparations in solid, semi-solid, liquid or gaseous forms, such as tablets, capsules, powders, granules, ointments, solutions, suppositories, injections, inhalants, gels, microspheres, and aerosols. In addition, other pharmaceutically active ingredients (including other anti-cancer agents as described elsewhere herein) and/or suitable excipients such as salts, buffers and stabilizers may, but need not, be present within the composition. Administration may be achieved by a variety of different routes, including oral, parenteral, nasal, intravenous, intradermal, subcutaneous or topical. Modes of administration depend upon the nature of the condition to be treated or prevented. Thus, ADI-PEG, e.g., ADI-PEG 20, may be administered orally, intranasally, intraperitoneally, parenterally, intravenously, intralymphatically, intratumorly, intramuscularly, interstitially, intra-arterially, subcutaneously, intraocularly, intrasynovial, transepithelial, and transdermally. An amount that, following administration, reduces, inhibits, prevents or delays the progression and/or metastasis of a cancer is considered effective. In certain embodiment, the ADI compositions herein increase median survival time of patients by a statistically significant amount. In one embodiment, the ADI treatments described herein increase median survival time of a patient by 4 weeks, 5 weeks, 6 weeks, 7 weeks, 8 weeks, 9 weeks, 10 weeks, 15 weeks, 20 weeks, 25 weeks, 30 weeks, 40 weeks, or longer. In certain embodiments, ADI treatments increase median survival time of a patient by 1 year, 2 years, 3 years, or longer. In one embodiment, the ADI treatments described herein increase progression-free survival by 2 weeks, 3 weeks, 4 weeks, 5 weeks, 6 weeks, 7 weeks, 8 weeks, 9 weeks, 10 weeks or longer. In certain embodiments, the ADI treatments described herein increase progression-free survival by 1 year, 2 years, 3 years, or longer.

In certain embodiments, the amount administered is sufficient to result in tumor regression, as indicated by a statistically significant decrease in the amount of viable tumor, for example, at least a 50% decrease in tumor mass, or by altered (e.g., decreased with statistical significance) scan dimensions. In certain embodiments, the amount administered is sufficient to result in stable disease. In other embodiments, the amount administered is sufficient to result in clinically relevant reduction in symptoms of a particular disease indication known to the skilled clinician.

In certain embodiments the amount administered is sufficient to inhibit NO synthesis, inhibit angiogenesis, and or is sufficient to induce apoptosis in tumor cells or any combination thereof. NO synthesis, angiogenesis and apoptosis may be measured using methods known in the art, see, e.g., *Current Protocols in Immunology* or *Current Protocols in Molecular Biology*, John Wiley & Sons, New York, N.Y. (2009 and updates thereto); Ausubel et al., *Short Protocols in Molecular Biology*, 3$^{rd}$ ed., Wiley & Sons, 1995; and other like references. In one particular embodiment the amount administered inhibits NO synthesis and inhibits the growth of melanoma and synergizes with other chemotherapies as described herein, such as cisplatin. Accordingly, one embodiment of the present disclosure provides a method of treating melanoma by administering ADI-PEG 20 in combination with cisplatin, wherein the treatment depletes endogenous nitric oxide (NO).

The precise dosage and duration of treatment is a function of the disease being treated and may be determined empirically using known testing protocols or by testing the compositions in model systems known in the art and extrapolating therefrom. Controlled clinical trials may also be performed. Dosages may also vary with the severity of the condition to be alleviated. A pharmaceutical composition is generally formulated and administered to exert a therapeutically useful effect while minimizing undesirable side effects. The composition may be administered one time, or may be divided into a number of smaller doses to be administered at intervals of time. For any particular subject, specific dosage regimens may be adjusted over time according to the individual need.

The ADI compositions may be administered alone or in combination with other known cancer treatments, such as radiation therapy, chemotherapy, transplantation, immunotherapy, hormone therapy, photodynamic therapy, etc. The compositions may also be administered in combination with antibiotics.

Typical routes of administering these and related pharmaceutical compositions thus include, without limitation, oral, topical, transdermal, inhalation, parenteral, sublingual, buccal, rectal, vaginal, and intranasal. The term parenteral as used herein includes subcutaneous injections, intravenous, intramuscular, intrasternal injection or infusion techniques. Pharmaceutical compositions according to certain embodiments of the present invention are formulated so as to allow the active ingredients contained therein to be bioavailable upon administration of the composition to a patient. Compositions that will be administered to a subject or patient may take the form of one or more dosage units, where for example, a tablet may be a single dosage unit, and a container of a herein described ADI composition in aerosol form may hold a plurality of dosage units. Actual methods of preparing such dosage forms are known, or will be apparent, to those skilled in this art; for example, see *Remington: The Science and Practice of Pharmacy*, 20th Edition (Philadelphia College of Pharmacy and Science, 2000). The composition to be administered will, in any event, contain a therapeutically effective amount of an ADI-PEG of the present disclosure, such as ADI-PEG 20, for treatment of a disease or condition of interest in accordance with teachings herein.

A pharmaceutical composition may be in the form of a solid or liquid. In one embodiment, the carrier(s) are particulate, so that the compositions are, for example, in tablet or powder form. The carrier(s) may be liquid, with the compositions being, for example, anoral oil, injectable liquid or an aerosol, which is useful in, for example, inhalatory administration. When intended for oral administration, the pharmaceutical composition is generally either solid or liquid form, where semi-solid, semi-liquid, suspension and gel forms are included within the forms considered herein as either solid or liquid.

As a solid composition for oral administration, the pharmaceutical composition may be formulated into a powder, granule, compressed tablet, pill, capsule, chewing gum, wafer or the like. Such a solid composition will typically contain one or more inert diluents or edible carriers. In addition, one or more of the following may be present: binders such as carboxymethylcellulose, ethyl cellulose, microcrystalline cellulose, gum tragacanth or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin; a flavoring agent such as peppermint, methyl salicylate or orange flavoring; and a coloring agent. When the pharmaceutical composition is in the form of a capsule, for example, a gelatin capsule, it may contain, in addition to materials of the above type, a liquid carrier such as polyethylene glycol or oil.

The pharmaceutical composition may be in the form of a liquid, for example, an elixir, syrup, solution, emulsion or suspension. The liquid may be for oral administration or for delivery by injection, as two examples. When intended for oral administration, preferred composition contain, in addition to the present compounds, one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent may be included.

The liquid pharmaceutical compositions, whether they be solutions, suspensions or other like form, may include one or more of the following adjuvants: sterile diluents such as water for injection, saline solution, in certain embodiments, physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Physiological saline is a preferred adjuvant. An injectable pharmaceutical composition is preferably sterile.

A liquid pharmaceutical composition intended for either parenteral or oral administration should contain an amount of ADI as herein disclosed, such as ADI-PEG 20, such that a suitable dosage will be obtained. Typically, this amount is at least 0.01% of ADI in the composition. When intended for oral administration, this amount may be varied to be between 0.1 and about 70% of the weight of the composition. Certain oral pharmaceutical compositions contain between about 4% and about 75% of ADI-PEG. In certain embodiments, pharmaceutical compositions and preparations according to the present invention are prepared so that a parenteral dosage unit contains between 0.01 to 10% by weight of ADI-PEG prior to dilution.

The pharmaceutical composition may be intended for topical administration, in which case the carrier may suitably comprise a solution, emulsion, ointment or gel base. The base, for example, may comprise one or more of the following: petrolatum, lanolin, polyethylene glycols, bee wax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device. The pharmaceutical composition may be intended for rectal administration, in the form, for example, of a suppository, which will melt in the rectum and release the drug. The composition for rectal administration may contain an oleaginous base as a suitable nonirritating excipient. Such bases include, without limitation, lanolin, cocoa butter and polyethylene glycol.

The pharmaceutical composition may include various materials, which modify the physical form of a solid or liquid dosage unit. For example, the composition may include materials that form a coating shell around the active ingredients. The materials that form the coating shell are typically inert, and may be selected from, for example, sugar, shellac, and other enteric coating agents. Alternatively, the active ingredients may be encased in a gelatin capsule. The pharmaceutical composition in solid or liquid form may include an agent that binds to ADI-PEG and thereby assists in the delivery of the compound. Suitable agents that may act in this capacity include monoclonal or polyclonal antibodies, one or more proteins or a liposome. The pharmaceutical composition may consist essentially of dosage units that can be administered as an aerosol. The term aerosol is used to denote a variety of systems ranging from those of colloidal nature to systems consisting of pressurized packages. Delivery may be by a liquefied or compressed gas or by a suitable pump system that dispenses the active ingredients. Aerosols may be delivered in single phase, bi-phasic, or tri-phasic systems in order to deliver the active ingredient(s). Delivery of the aerosol includes the necessary container, activators, valves, subcontainers, and the like, which together may form a kit. One of ordinary skill in the art, without undue experimentation may determine preferred aerosols.

The pharmaceutical compositions may be prepared by methodology well known in the pharmaceutical art. For example, a pharmaceutical composition intended to be administered by injection can be prepared by combining a composition that comprises ADI-PEG as described herein and optionally, one or more of salts, buffers and/or stabilizers, with sterile, distilled water so as to form a solution. A surfactant may be added to facilitate the formation of a homogeneous solution or suspension. Surfactants are compounds that non-covalently interact with the ADI-PEG composition so as to facilitate dissolution or homogeneous suspension of the ADI-PEG in the aqueous delivery system.

The compositions may be administered in a therapeutically effective amount, which will vary depending upon a variety of factors including the activity of the specific compound (e.g., ADI-PEG) employed; the metabolic stability and length of action of the compound; the age, body weight, general health, sex, and diet of the patient; the mode and time of administration; the rate of excretion; the drug combination; the severity of the particular disorder or condition; and the subject undergoing therapy.

A therapeutically effective amount of one of the compounds of the present invention is an amount that is effective to inhibit tumor growth. Generally, treatment is initiated with small dosages which can be increased by small increments until the optimum effect under the circumstances is achieved. Generally, a therapeutic dosage of compounds of the present invention may be from about 1 to about 200 mg/kg twice a week to about once every two weeks. For example, the dosage may be about 1 mg/kg once a week as a 2 ml intravenous injection to about 20 mg/kg once every 3 days. In a further embodiment, the dose may be from about 50 $IU/m^2$ to about 700 $IU/m^2$, administered about once every 3 days, about once a week, about twice a week, or about once every 2 weeks. In certain embodiments, the dose may be about 50 $IU/m^2$, 60 $IU/m^2$, 70 $IU/m^2$, 80 $IU/m^2$, 90 $IU/m^2$, 100 $IU/m^2$, 110 $IU/m^2$, 120 $IU/m^2$, 130 $IU/m^2$, 140 $IU/m^2$, 150 $IU/m^2$, 160 $IU/m^2$, 170 $IU/m^2$, 180 $IU/m^2$, 190 $IU/m^2$, 200 $IU/m^2$, 210 $IU/m^2$, 220 $IU/m^2$, 230 $IU/m^2$, 240 $IU/m^2$, 250 $IU/m^2$, 260 $IU/m^2$, 270 $IU/m^2$, 280 $IU/m^2$, 290 $IU/m^2$, 300 $IU/m^2$, 310 $IU/m^2$, about 320 $IU/m^2$, about 330 $IU/m^2$, 340 $IU/m^2$ about 350 $IU/m^2$, 360 $IU/m^2$, 370 $IU/m^2$, 380 $IU/m^2$, 390 $IU/m^2$, 400 $IU/m^2$, 410 $IU/m^2$, 420 $IU/m^2$, 430 $IU/m^2$, 440 $IU/m^2$, 450 $IU/m^2$, 500 $IU/m^2$, 550 $IU/m^2$, 600 $IU/m^2$, 620 $IU/m^2$, 630 $IU/m^2$, 640 $IU/m^2$, 650 $IU/m^2$, 660 $IU/m^2$, 670 $IU/m^2$, 680 $IU/m^2$, 690 $IU/m^2$, or about 700 $IU/m^2$ administered about once every 3 days, about once a week, about twice a week, or about once every 2 weeks. In certain embodiments where a subject may mount an anti-ADI immune response, the dose may be modified as desired by the skilled clinician.

The optimum dosage with ADI-SS-PEG5,000 may be about twice a week, while the optimum dosage with ADI-SS-PEG20,000 may be from about once a week to about once every two weeks. In certain embodiments, the optimum dosage with ADI-SS-PEG20,000 may be about twice a week.

ADI-PEG may be mixed with a phosphate buffered saline solution, or any other appropriate solution known to those skilled in the art, prior to injection. In one embodiment, a liquid composition comprising ADI-PEG comprises about 10 to about 12 mg of ADI, about 20 to about 40 mg of polyethylene glycol, 1.27 mg+5% monobasic sodium phosphate, USP; about 3 mg+5% dibasic sodium phosphate, USP; 7.6 mg+5% sodium chloride, USP; at a pH of about 6.6 to about 7; in an appropriate amount of water for injection (e.g., about 1 ml or about 2 ml). In one embodiment, a liquid composition comprising ADI-PEG comprises histidine-HCl, and in certain embodiments, the composition buffer is from about 0.0035M Histidine-HCl to about 0.35M Histidine-HCl. In one particular embodiment, the composition is formulated in a buffer comprising 0.035 M Histidine-HCl at pH 6.8 with 0.13 M sodium chloride. In another embodiment, the composition is formulated in a buffer comprising 0.02M sodium phosphate buffer at pH 6.8 with 0.13 M sodium chloride.

In one embodiment, a composition comprising ADI or ADI-PEG has a pH of about 5 to about 9, about 6 to about 8, or about 6.5 to about 7.5. In some embodiments, the composition comprising ADI has a pH of about 6.8±1.0.

In one embodiment, free PEG in a composition comprising ADI-PEG is between 1-10%, and in a further embodiment, is less than 7%, less than 6%, less than 5%, less than 4%, less than 3%, less than 2% or less than 1% of the total PEG. In certain embodiments, the native ADI in a composition comprising ADI-PEG is less than about 1%, 0.9%, 0.8%, 0.7%, 0.6%, 0.5%, 0.4%, 0.3%, 0.2% or less than 0.1%. Generally, compositions comprising ADI-PEG have total impurities less than or equal to about 4%, 3%, 2%, 1.5%, 1% or 0.5%.

In one embodiment, the free sulfhydryl in a composition comprising ADI or ADI-PEG is greater than about 90%. In some embodiments, the free sulfhydryl in a composition comprising ADI or ADI-PEG is about 91%, about 92%, about 93%, about 94% or about 95%, about 96% about 97%, about 98% about 99% or more.

In one embodiment, the ADI or ADI-PEG in a composition has a Km of from about 0.5 µM to about 15 µM, and in a further embodiment, is from about 1 µM to about 12 µM, about 1 µM to about 10 µM, about 1.5 µM to about 9 µM, about 1.5 µM to about 8 µM or about 1.5 µM to about 7 µM. In certain embodiments, the ADI or ADI-PEG in a composition has a Km of about 1.5 µM to about 6.5 µM. In some embodiments, the ADI or ADI-PEG in a composition has a Km of about 1.5 µM, about 2 µM, about 2.5 µM, about 3 µM, about 3.5 µM, about 4 µM, about 4.5 µM, about 5 µM, about 5.5 µM, about 6 µM, about 6.5 µM, or about 7 µM.

In one embodiment, the ADI or ADI-PEG in a composition has a Kcat of from about 0.5 $sec^{-1}$ to about 15 $sec^{-1}$, and in a further embodiment, is from about 1 $sec^{-1}$ to about 12 $sec^{-1}$, about 1 $sec^{-1}$ to about 10 $sec^{-1}$, about 1.5 $sec^{-1}$ to about 9 $sec^{-1}$, about 2 $sec^{-1}$ to about 8 $sec^{-1}$ or about 2.5 $sec^{-1}$ to about 7 $sec^{-1}$. In certain embodiments, the ADI or ADI-PEG in a composition has a Kcat of about 2.5 $sec^{-1}$ to about 7.5 $sec^{-1}$. In some embodiments, the ADI or ADI-PEG in a composition has a Kcat of about 2.5 $sec^{-1}$, about 3 $sec^{-1}$, about 3.5 $sec^{-1}$, about 4 $sec^{-1}$, about 4.5 $sec^{-1}$, about 5 $sec^{-1}$, about 5.5 $sec^{-1}$, about 6 $sec^{-1}$, about 6.5 $sec^{-1}$, about 7 $sec^{-1}$, about 7.5 $sec^{-1}$ or about 8 $sec^{-1}$.

In one embodiment, the ADI or ADI-PEG in a composition has a conductivity (also referred to in the art as specific conductance) of about 5 mS/cm to about 20 mS/cm, and in further embodiments, from about 5 mS/cm to about 15 mS/cm, about 7 mS/cm to about 15 mS/cm, about 9 mS/cm to about 15 mS/cm or about 10 mS/cm to about 15 mS/cm. In some embodiments, the ADI or ADI-PEG in a composition has a conductivity of about 9 mS/cm, about 10 mS/cm, about 11 mS/cm, about 12 mS/cm or about 13 mS/cm, about 14 mS/cm or about 15 mS/cm. In certain embodiments, the ADI or ADI-PEG in a composition has a conductivity of about 13 mS/cm±1.0 mS/cm.

In one embodiment, the ADI or ADI-PEG in a composition has an osmolality of about 50 mOsm/kg to about 500 mOsm/kg, about 100 mOsm/kg to about 400 mOsm/kg, about 150 mOsm/kg to about 350 mOsm/kg, about 200 mOsm/kg to about 350 mOsm/kg or about 250 mOsm/kg to about 350 mOsm/kg. In certain embodiments, the ADI or ADI-PEG in a composition has an osmolality of about 300±30 mOsm/kg.

Compositions comprising ADI-PEG of the present disclosure may also be administered simultaneously with, prior to, or after administration of one or more other therapeutic agents. Such combination therapy may include administration of a single pharmaceutical dosage formulation which contains a compound of the invention and one or more additional active agents, as well as administration of compositions comprising ADI-PEG (e.g., ADI-PEG 20) of the invention and each active agent in its own separate pharmaceutical dosage formulation. For example, ADI-PEG as described herein and the other active agent can be administered to the patient together in a single oral dosage composition such as a tablet or capsule, or each agent administered in separate oral dosage formulations. Similarly, ADI-PEG as described herein and the other active agent can be administered to the patient together in a single parenteral dosage composition such as in a saline solution or other physiologically acceptable solution, or each agent administered in separate parenteral dosage formulations. Where separate dosage formulations are used, the compositions comprising ADI-PEG and one or more additional active agents can be administered at essentially the same time, i.e., concurrently, or at separately staggered times, i.e., sequentially and in any order; combination therapy is understood to include all these regimens.

Thus, in certain embodiments, also contemplated is the administration of the ADI compositions of this disclosure in combination with one or more other therapeutic agents. Such therapeutic agents may be accepted in the art as a standard treatment for a particular disease state as described herein, such as a particular cancer or GVHD. Exemplary therapeutic agents contemplated include cytokines, growth factors, steroids, NSAIDs, DMARDs, anti-inflammatories, chemotherapeutics, radiotherapeutics, autophagy inhibitors, or other active and ancillary agents.

In certain embodiments, the ADI compositions disclosed herein may be administered in conjunction with any number of chemotherapeutic agents. Examples of chemotherapeutic agents include alkylating agents such as thiotepa and cyclophosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxoids, e.g. paclitaxel (TAXOL®, Bristol-Myers Squibb Oncology, Princeton, N.J.) and docetaxel (TAXOTERE®, Rhne-Poulenc Rorer, Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylomithine (DMFO); retinoic acid derivatives such as Targretin™ (bexarotene), Panretin™ (alitretinoin); ONTAK™ (denileukin diftitox); esperamicins; capecitabine; and pharmaceutically acceptable salts, acids or derivatives of any of the above. Also included in this definition are anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston); and anti-androgens such as flutamide, nilutamide, bicalutamide, leuprolide, and goserelin; Further chemotherapeutic agents include sorafenib and other protein kinase inhibitors such as afatinib, axitinib, bevacizumab, cetuximab, crizotinib, dasatinib, erlotinib, fostamatinib, gefitinib, imatinib, lapatinib, lenvatinib, mubritinib, nilotinib, panitumumab, pazopanib, pegaptanib, ranibizumab, ruxolitinib, trastuzumab, vandetanib, vemurafenib, and sunitinib; sirolimus (rapamycin), everolimus and other mTOR inhibitors. Pharmaceutically acceptable salts, acids or derivatives of any of the above are also contemplated for use herein.

In certain embodiments, the ADI compositions disclosed herein may be administered in conjunction with any number of autophagy inhibitors. In some preferred embodiments, the autophagy inhibitor is selected from the group consisting of: chloroquine, 3-methyladenine, hydroxychloroquine (Plaquenil™), bafilomycin A1, 5-amino-4-imidazole carboxamide riboside (AICAR), okadaic acid, autophagy-suppressive algal toxins which inhibit protein phosphatases of type 2A or type 1, analogues of cAMP, and drugs which elevate cAMP levels, adenosine, N6-mercaptopurine riboside, wortmannin, and vinblastine. In addition, antisense or siRNA that inhibits expression of proteins essential for autophagy, such as for example ATG5, may also be used.

In one embodiment, the combination of ADI-PEG with one or more therapeutic agents acts additively or synergistically. In this regard, synergizing agents are described herein, which include a therapeutic agent (e.g., chemotherapeutic agent, autophagy inhibitor, mTOR inhibitor, or any other therapeutic agent used for the treatment of cancer, GVHD, or inflammatory bowel disease as described herein) that is capable of acting synergistically with ADI-PEG as provided herein, where such synergy manifests as a detectable effect that is greater (i.e., in a statistically significant manner relative to an appropriate control condition) in magnitude than the effect that can be detected when the chemotherapeutic agent is present but the ADI-PEG composition is absent, and/or when the ADI-PEG is present but the chemotherapeutic agent is absent. Methods for measuring synergy are known in the art (see e.g., Cancer Res Jan. 15, 2010 70; 440).

The compositions comprising ADI, and optionally other therapeutic agents, as described herein may be used in therapeutic methods for treating of cancer and methods for preventing metastasis of a cancer. Thus, the present invention provides for methods for treating, ameliorating the symptoms of, or inhibiting the progression of or prevention of a variety of different cancers. In another embodiment, the present disclosure provides methods for treating, ameliorating the symptoms of, or inhibiting the progression of GVHD. In particular the present disclosure provides methods for treating, ameliorating the symptoms of, or inhibiting the progression of a cancer or GVHD in a patient comprising administering to the patient a therapeutically effective amount of an ADI composition as described herein, thereby treating, ameliorating the symptoms of, or inhibiting the progression of the cancer or GVHD. Thus, the ADI compositions described herein may be administered to an individual afflicted with inflammatory bowel disease (e.g., Crohn's disease; ulcerative colitis), GVHD or a cancer, including, but not limited to leukemia (e.g. acute myeloid leukemia and relapsed acute myeloid leukemia), melanoma, sarcomas (including, but not limited to, metastatic sarcomas, uterine leiomyosarcoma), pancreatic cancer, prostate cancer (such as, but not limited to, hormone refractory prostate cancer), mesothelioma, lymphatic leukemia, chronic myelogenous leukemia, lymphoma, small cell lung cancer, breast cancer, ovarian cancer, colorectal cancer, gastric cancer (including, but not limited to, gastric adenocarcinoma), glioma, glioblastoma multi-form, retinoblastoma, neuroblastoma, non-small cell lung cancer (NSCLC), kidney cancer (including but not limited to renal cell carcinoma), bladder cancer, uterine cancer, esophageal cancer, brain cancer, head and neck cancers (including, but not limited to, squamous cell carcinoma of the head and neck; cancer of the tongue), cervical cancer, testicular cancer, gallbladder, cholangiocarcinoma, and stomach cancer.

In one embodiment, the present disclosure provides a method of treating, ameliorating the symptoms of, or inhibiting the progression of myeloid leukemia, such as, but not limited to, acute myeloid leukemia (AML), by administering a therapeutically effective amount of an ADI-PEG 20. In certain embodiments, the myeloid leukemia, such as AML, is deficient in ASS, ASL, or both. In another embodiment, the myeloid leukemia, (e.g., AML) does not comprise the translocation t(15; 17). In a further embodiment, the present disclosure provides a method of treating AML comprising administering ADI-PEG 20 about once every 3 days, about once a week, about twice a week, or about once every 2 weeks. In certain embodiments, the dose of ADI-PEG 20 administered for the treatment of AML is between about 160 IU/m2 and about 360 IU/m2, and in other embodiments is about 160 IU/m2, about 170 IU/m$^2$, 180 IU/m$^2$, 190 IU/m$^2$, 200 IU/m$^2$, 210 IU/m$^2$, 220 IU/m$^2$, 230 IU/m$^2$, 240 IU/m$^2$, 250 IU/m$^2$, 260 IU/m$^2$, 270 IU/m$^2$, 280 IU/m$^2$, 290 IU/m$^2$, 300 IU/m$^2$, 310 IU/m$^2$, about 320 IU/m$^2$, about 330 IU/m$^2$, 340 IU/m$^2$ about 350 IU/m$^2$, about 360 IU/m$^2$, about 370 IU/m$^2$, 380 IU/m$^2$, 390 IU/m$^2$, 400 IU/m$^2$, 410 IU/m$^2$, 420 IU/m$^2$, 430 IU/m$^2$, 440 IU/m$^2$, 450 IU/m$^2$, 500 IU/m$^2$, 550 IU/m$^2$, 600 IU/m$^2$, 640 IU/m$^2$, or about 700 IU/m$^2$. In certain embodiments, wherein the treatment of AML with ADI-PEG induces an immune response against ADI, the present disclosure provides a method of treating AML, wherein the dose of ADI is doubled and may be increased to 640 IU/m2 per week or more. In one particular embodiment the ADI for the treatment of AML is modified with 3.5-6.5, or in one embodiment, 4.5-5.5 PEG molecules per ADI. In another embodiment, the present disclosure provides a method of treating AML by administering a composition comprising ADI-PEG 20 wherein the composition comprises an ADI modified with 5±1.5 PEG molecules, and in one embodiment, 5±1.5 straight chain PEG molecules, and, in certain embodiments, the composition comprises less than about 0.5% native ADI (i.e., unmodified with PEG) and/or less than about 5% free PEG. In a further embodiment, the composition comprises a histidine-HCL buffer.

In one embodiment, the present disclosure provides a method of treating, ameliorating the symptoms of, or inhibiting the progression of sarcomas, including but not limited to metastatic sarcomas, by administering a therapeutically effective amount of a ADI-PEG 20. In certain embodiments, the sarcoma is deficient in ASS, ASL, or both. In a further embodiment, the present disclosure provides a method of treating a sarcoma comprising administering ADI-PEG 20 about once every 3 days, about once a week, about twice a week, or about once every 2 weeks. In certain embodiments, the dose of ADI-PEG 20 administered for the treatment of AML is between about 160 IU/m2 and about 360 IU/m2, and in other embodiments is about 160 IU/m2, about 170 IU/m$^2$, 180 IU/m$^2$, 190 IU/m$^2$, 200 IU/m$^2$, 210 IU/m$^2$, 220 IU/m$^2$, 230 IU/m$^2$, 240 IU/m$^2$, 250 IU/m$^2$, 260 IU/m$^2$, 270 IU/m$^2$, 280 IU/m$^2$, 290 IU/m$^2$, 300 IU/m$^2$, 310 IU/m$^2$, about 320 IU/m$^2$, about 330 IU/m$^2$, 340 IU/m$^2$ about 350 IU/m$^2$, about 360 IU/m$^2$, about 370 IU/m$^2$, 380 IU/m$^2$, 390 IU/m$^2$, 400 IU/m$^2$, 410 IU/m$^2$, 420 IU/m$^2$, 430 IU/m$^2$, 440 IU/m$^2$, 450 IU/m$^2$, 500 IU/m$^2$, 550 IU/m$^2$, 600 IU/m$^2$, 640 IU/m$^2$, or about 700 IU/m$^2$. In certain embodiments, wherein the treatment of a sarcoma with ADI-PEG induces an immune response against ADI, the present disclosure provides a method of treating sarcoma, wherein the dose of ADI is doubled and may be increased to 640 IU/m2 per week or more. In one particular embodiment the ADI for the treatment of AML is modified with 3.5-6.5, or in one embodiment, 4.5-5.5 PEG molecules per ADI. In another embodiment, the present disclosure provides a method of treating a sarcoma, including a metastatic sarcoma, by administering a composition comprising ADI-PEG 20 wherein the composition comprises an ADI modified with 5±1.5 PEG molecules, and in one embodiment, 5±1.5 straight chain PEG molecules, and, in certain embodiments, the composition comprises less than about 0.5% native ADI (i.e., unmodified with PEG) and/or less than about 5% free PEG. In a further embodiment, the composition comprises a histidine-HCL buffer.

In one embodiment, the present disclosure provides a method of treating, ameliorating the symptoms of, or inhibiting the progression of pancreatic cancer by administering a therapeutically effective amount of ADI-PEG 20 in combination with an autophagy inhibitor, such as but not limited to chloroquine, 3-methyladenine, hydroxychloroquine, bafilomycin A1, 5-amino-4-imidazole carboxamide riboside (AICAR), okadaic acid, N6-mercaptopurine riboside, wortmannin, and vinblastine. In certain embodiments, the pancreatic cancer is deficient in ASS, ASL, or both. In a further embodiment, the present disclosure provides a method of treating pancreatic cancer comprising administering ADI-PEG 20 about once every 3 days, about once a week, about twice a week, or about once every 2 weeks; in combination with a therapeutically effective amount of an autophagy inhibitor, such as chloroquine. In this regard, a therapeutically effective dose of chloroquine may be an initial dose of about 600 mg base followed by an additional 300 mg base and a single dose of 300 mg base on each of two consecutive days. This represents a total dose of 2.5 g chloroquine phosphate or 1.5 g base in three days. In further embodiments, the dose may be about 300 mg base. The dose of chloroquine, or other autophagy inhibitor, may be modified as needed by a skilled clinician using dosages known in the art. As would be understood by the skilled person, the autophagy inhibitor may be administered before, at the same time as or after a composition comprising ADI-PEG 20. In certain embodiments, the dose of ADI-PEG 20 administered for the treatment of pancreatic cancer is between about 160 IU/m2 and about 360 IU/m2, and in other embodiments is about 160 IU/m2, about 170 IU/m$^2$, 180 IU/m$^2$, 190 IU/m$^2$, 200 IU/m$^2$, 210 IU/m$^2$, 220 IU/m$^2$, 230 IU/m$^2$, 240 IU/m$^2$, 250 IU/m$^2$, 260 IU/m$^2$, 270 IU/m$^2$, 280 IU/m$^2$, 290 IU/m$^2$, 300 IU/m$^2$, 310 IU/m$^2$, about 320 IU/m$^2$, about 330 IU/m$^2$, 340 IU/m$^2$ about 350 IU/m$^2$, about 360 IU/m$^2$, about 370 IU/m$^2$, 380 IU/m$^2$, 390 IU/m$^2$, 400 IU/m$^2$, 410 IU/m$^2$, 420 IU/m$^2$, 430 IU/m$^2$, 440 IU/m$^2$, 450 IU/m$^2$, 500 IU/m$^2$, 550 IU/m$^2$, 600 IU/m$^2$, 640 IU/m$^2$, or about 700 IU/m$^2$. In certain embodiments, wherein the treatment of pancreatic cancer with ADI-PEG in combination with chloroquine induces an immune response against ADI, the present disclosure provides a method of treating pancreatic cancer, wherein the dose of ADI is doubled and may be increased to 640 IU/m2 per week or more. In one particular embodiment the ADI for the treatment of pancreatic cancer is modified with 3.5-6.5, or in one embodiment, 4.5-5.5 PEG molecules per ADI. In another embodiment, the present disclosure provides a method of treating pancreatic cancer by administering chloroquine, or other appropriate autophagy inhibitor, in combination with a composition comprising ADI-PEG 20 wherein the composition comprises an ADI modified with 5±1.5 PEG molecules, and in one embodiment, 5±1.5 straight chain PEG molecules, and, in certain embodiments, the composition comprises less than about 0.5% native ADI (i.e., not modified with PEG) and/or less than about 5% free PEG. In a further embodiment, the composition comprises a histidine-HCL buffer.

In one embodiment, the present disclosure provides a method of treating, ameliorating the symptoms of, or inhibiting the progression of small cell lung cancer by administering a therapeutically effective amount of ADI-PEG 20 in combination with an autophagy inhibitor. In certain embodiments, the small cell lung cancer is deficient in ASS, ASL, or both. In a further embodiment, the present disclosure provides a method of treating small cell lung cancer comprising administering ADI-PEG 20 about once every 3 days, about once a week, about twice a week, or about once every 2 weeks; in combination with a therapeutically effective amount of an autophagy inhibitor, such as chloroquine. In this regard, a therapeutically effective dose of chloroquine may be an initial dose of about 600 mg base followed by an additional 300 mg base and a single dose of 300 mg base on each of two consecutive days. This represents a total dose of 2.5 g chloroquine phosphate or 1.5 g base in three days. In further embodiments, the dose may be about 300 mg base. The dose of chloroquine may be modified as needed by a skilled clinician using dosages known in the art. As would be understood by the skilled person, the autophagy inhibitor may be administered before, at the same time as or after a composition comprising ADI-PEG 20. In certain embodiments, the dose of ADI-PEG 20 administered for the treatment of small cell lung cancer is between about 160 IU/m2 and about 360 IU/m2, and in other embodiments is about 160 IU/m2, about 170 IU/m$^2$, 180 IU/m$^2$, 190 IU/m$^2$, 200 IU/m$^2$, 210 IU/m$^2$, 220 IU/m$^2$, 230 IU/m$^2$, 240 IU/m$^2$, 250 IU/m$^2$, 260 IU/m$^2$, 270 IU/m$^2$, 280 IU/m$^2$, 290 IU/m$^2$, 300 IU/m$^2$, 310 IU/m$^2$, about 320 IU/m$^2$, about 330 IU/m$^2$, 340 IU/m$^2$ about 350 IU/m$^2$, about 360 IU/m$^2$, about 370 IU/m$^2$, 380 IU/m$^2$, 390 IU/m$^2$, 400 IU/m$^2$, 410 IU/m$^2$, 420 IU/m$^2$, 430 IU/m$^2$, 440 IU/m$^2$, 450 IU/m$^2$, 500 IU/m$^2$, 550 IU/m$^2$, 600 IU/m$^2$, 640 IU/m$^2$, or about 700 IU/m$^2$. In certain embodiments, wherein the treatment of small cell lung cancer with ADI-PEG in combination with chloroquine induces an immune response against ADI, the present disclosure provides a method of treating small cell lung cancer, wherein the dose of ADI is doubled and may be increased to 640 IU/m2 per week or more. In one particular embodiment the ADI for the treatment of small cell lung cancer is modified with 3.5-6.5, or in one embodiment, 4.5-

5.5 PEG molecules per ADI. In another embodiment, the present disclosure provides a method of treating small cell lung cancer by administering chloroquine in combination with a composition comprising ADI-PEG 20 wherein the composition comprises an ADI modified with 5±1.5 PEG molecules, and in one embodiment, 5±1.5 straight chain PEG molecules, and, in certain embodiments, the composition comprises less than about 0.5% native ADI (i.e., not modified with PEG) and/or less than about 5% free PEG. In a further embodiment, the composition comprises a histidine-HCL buffer.

In one embodiment, the present disclosure provides a method of treating, ameliorating the symptoms of, or inhibiting the progression of sarcomas (including but not limited to, metastatic sarcomas) by administering a therapeutically effective amount of ADI-PEG 20 in combination with an autophagy inhibitor. In certain embodiments, the sarcoma is deficient in ASS, ASL, or both. In a further embodiment, the present disclosure provides a method of treating sarcoma comprising administering ADI-PEG 20 about once every 3 days, about once a week, about twice a week, or about once every 2 weeks; in combination with a therapeutically effective amount of an autophagy inhibitor, such as chloroquine. In this regard, a therapeutically effective dose of chloroquine may be an initial dose of about 600 mg base followed by an additional 300 mg base and a single dose of 300 mg base on each of two consecutive days. This represents a total dose of 2.5 g chloroquine phosphate or 1.5 g base in three days. In further embodiments, the dose may be about 300 mg base. The dose of chloroquine may be modified as needed by a skilled clinician using dosages known in the art. As would be understood by the skilled person, the autophagy inhibitor may be administered before, at the same time as or after a composition comprising ADI-PEG 20. In certain embodiments, the dose of ADI-PEG 20 administered for the treatment of sarcoma is between about 160 IU/$m^2$ and about 360 IU/$m^2$, and in other embodiments is about 160 IU/m2, about 170 IU/$m^2$, 180 IU/$m^2$, 190 IU/$m^2$, 200 IU/$m^2$, 210 IU/$m^2$, 220 IU/$m^2$, 230 IU/$m^2$, 240 IU/$m^2$, 250 IU/$m^2$, 260 IU/$m^2$, 270 IU/$m^2$, 280 IU/$m^2$, 290 IU/$m^2$, 300 IU/$m^2$, 310 IU/$m^2$, about 320 IU/$m^2$, about 330 IU/$m^2$, 340 IU/$m^2$ about 350 IU/$m^2$, about 360 IU/$m^2$, about 370 IU/$m^2$, 380 IU/$m^2$, 390 IU/$m^2$, 400 IU/$m^2$, 410 IU/$m^2$, 420 IU/$m^2$, 430 IU/$m^2$, 440 IU/$m^2$, 450 IU/$m^2$, 500 IU/$m^2$, 550 IU/$m^2$, 600 IU/$m^2$, 640 IU/$m^2$, or about 700 IU/$m^2$. In certain embodiments, wherein the treatment of sarcoma with ADI-PEG in combination with chloroquine induces an immune response against ADI, the present disclosure provides a method of treating sarcoma, wherein the dose of ADI is doubled and may be increased to 640 IU/$m^2$ per week or more. In one particular embodiment the ADI for the treatment of sarcoma is modified with 3.5-6.5, or in one embodiment, 4.5-5.5 PEG molecules per ADI. In another embodiment, the present disclosure provides a method of treating sarcoma by administering chloroquine in combination with a composition comprising ADI-PEG 20 wherein the composition comprises an ADI modified with 5±1.5 PEG molecules, and in one embodiment, 5±1.5 straight chain PEG molecules, and, in certain embodiments, the composition comprises less than about 0.5% native ADI (i.e., not modified with PEG) and/or less than about 5% free PEG. In a further embodiment, the composition comprises a histidine-HCL buffer.

In one embodiment, the present disclosure provides a method of treating, ameliorating the symptoms of, or inhibiting the progression of melanoma by administering a therapeutically effective amount of ADI-PEG 20 in combination with docetaxel. In certain embodiments, the melanoma is deficient in ASS, ASL, or both. In a further embodiment, the present disclosure provides a method of treating melanoma comprising administering ADI-PEG 20 about once every 3 days, about once a week, about twice a week, or about once every 2 weeks; in combination with a therapeutically effective amount of docetaxel. In this regard, a therapeutically effective dose of docetaxel may comprise 75 mg/$m^2$ or 100 mg/$m^2$ administered intravenously over between 30 minutes and 1 hour about every 3 weeks. As would be understood by the skilled clinician, the dose of docetaxel may be modified depending on disease indication and/or prior treatments, and docetaxel may be administered before, at the same time as or after a composition comprising ADI-PEG 20. In certain embodiments, the dose of ADI-PEG 20 administered for the treatment of melanoma is between about 160 IU/$m^2$ and about 360 IU/m2, and in other embodiments is about 160 IU/$m^2$, about 170 IU/$m^2$, 180 IU/$m^2$, 190 IU/$m^2$, 200 IU/$m^2$, 210 IU/$m^2$, 220 IU/$m^2$, 230 IU/$m^2$, 240 IU/$m^2$, 250 IU/$m^2$, 260 IU/$m^2$, 270 IU/$m^2$, 280 IU/$m^2$, 290 IU/$m^2$, 300 IU/$m^2$, 310 IU/$m^2$, about 320 IU/$m^2$, about 330 IU/$m^2$, 340 IU/$m^2$ about 350 IU/$m^2$, about 360 IU/$m^2$, about 370 IU/$m^2$, 380 IU/$m^2$, 390 IU/$m^2$, 400 IU/$m^2$, 410 IU/$m^2$, 420 IU/$m^2$, 430 IU/$m^2$, 440 IU/$m^2$, 450 IU/$m^2$, 500 IU/$m^2$, 550 IU/$m^2$, 600 IU/$m^2$, 640 IU/$m^2$, or about 700 IU/$m^2$. In certain embodiments, wherein the treatment of melanoma with ADI-PEG in combination with docetaxel induces an immune response against ADI, the present disclosure provides a method of treating melanoma, wherein the dose of ADI is doubled and may be increased to 640 IU/m2 per week or more. In one particular embodiment the ADI for the treatment of melanoma is modified with 3.5-6.5, or in one embodiment, 4.5-5.5, PEG molecules per ADI. In another embodiment, the present disclosure provides a method of treating melanoma by administering docetaxel in combination with a composition comprising ADI-PEG 20 wherein the composition comprises an ADI modified with 5±1.5 PEG molecules, and in one embodiment, 5±1.5 straight chain PEG molecules, and, in certain embodiments, the composition comprises less than about 0.5% native ADI (i.e., not modified with PEG) and/or less than about 5% free PEG. In a further embodiment, the composition comprises a histidine-HCL buffer.

In one embodiment, the present disclosure provides a method of treating, ameliorating the symptoms of, or inhibiting the progression of melanoma by administering a therapeutically effective amount of ADI-PEG 20 in combination with cisplatin. In certain embodiments, the melanoma is deficient in ASS, ASL, or both. In a further embodiment, the present disclosure provides a method of treating melanoma comprising administering ADI-PEG 20 about once every 3 days, about once a week, about twice a week, or about once every 2 weeks; in combination with a therapeutically effective amount of cisplatin. In this regard, a therapeutically effective dose of cisplatin may comprise administration either once per cycle (every 3-4 weeks) at 50-100 mg/$m^2$, or daily for 5 days for a total of 100 mg/$m^2$ per cycle. As would be understood by the skilled clinician, the dose of cisplatin may be modified depending on disease indication, individual patient, and/or prior treatments, and cisplatin may be administered before, at the same time as or after a composition comprising ADI-PEG 20. In certain embodiments, the dose of ADI-PEG 20 administered for the treatment of melanoma is between about 160 IU/$m^2$ and about 360 IU/$m^2$, and in other embodiments is about 160 IU/$m^2$, about 170 IU/$m^2$, 180 IU/$m^2$, 190 IU/$m^2$, 200 IU/$m^2$, 210 IU/$m^2$, 220 IU/$m^2$, 230 IU/$m^2$, 240 IU/$m^2$, 250 IU/$m^2$, 260 IU/$m^2$, 270 IU/$m^2$, 280 IU/$m^2$, 290 IU/$m^2$, 300 IU/$m^2$, 310 IU/$m^2$, about 320 IU/$m^2$, about 330 IU/$m^2$, 340 IU/$m^2$ about 350 IU/$m^2$, about 360

IU/m², about 370 IU/m², 380 IU/m², 390 IU/m², 400 IU/m², 410 IU/m², 420 IU/m², 430 IU/m², 440 IU/m², 450 IU/m², 500 IU/m², 550 IU/m², 600 IU/m², 640 IU/m², or about 700 IU/m². In certain embodiments, wherein the treatment of melanoma with ADI-PEG in combination with cisplatin induces an immune response against ADI, the present disclosure provides a method of treating melanoma, wherein the dose of ADI is doubled and may be increased to 640 IU/m2 per week or more. In one particular embodiment the ADI for the treatment of melanoma is modified with 3.5-6.5, or in one embodiment, 4.5-5.5, PEG molecules per ADI. In another embodiment, the present disclosure provides a method of treating melanoma by administering cisplatin in combination with a composition comprising ADI-PEG 20 wherein the composition comprises an ADI modified with 5±1.5 PEG molecules, and in one embodiment, 5±1.5 straight chain PEG molecules, and, in certain embodiments, the composition comprises less than about 0.5% native ADI (i.e., not modified with PEG) and/or less than about 5% free PEG. In a further embodiment, the composition comprises a histidine-HCL buffer.

In one embodiment, the present disclosure provides a method of treating, ameliorating the symptoms of, or inhibiting the progression of renal cell carcinoma by administering a therapeutically effective amount of ADI-PEG 20 in combination with an mTOR inhibitor, such as but not limited to rapamycin, temsirolimus, everolimus, and ridaforolimus. In certain embodiments, the renal cell carcinoma is deficient in ASS, ASL, or both. In a further embodiment, the present disclosure provides a method of treating renal cell carcinoma comprising administering ADI-PEG 20 about once every 3 days, about once a week, about twice a week, or about once every 2 weeks; in combination with a therapeutically effective amount of an mTOR inhibitor, such as rapamycin. The dose of rapamycin, or other mTOR inhibitor, may be determined as needed by a skilled clinician using dosages known in the art. As would be understood by the skilled person, the mTOR inhibitor may be administered before, at the same time as or after a composition comprising ADI-PEG 20. In certain embodiments, the dose of ADI-PEG 20 administered for the treatment of renal cell carcinoma is between about 160 IU/m² and about 360 IU/m², and in other embodiments is about 160 IU/m², about 170 IU/m², 180 IU/m², 190 IU/m², 200 IU/m², 210 IU/m², 220 IU/m², 230 IU/m², 240 IU/m², 250 IU/m², 260 IU/m², 270 IU/m², 280 IU/m², 290 IU/m², 300 IU/m², 310 IU/m², about 320 IU/m², about 330 IU/m², 340 IU/m² about 350 IU/m², about 360 IU/m², about 370 IU/m², 380 IU/m², 390 IU/m², 400 IU/m², 410 IU/m², 420 IU/m², 430 IU/m², 440 IU/m², 450 IU/m², 500 IU/m², 550 IU/m², 600 IU/m², 640 IU/m², or about 700 IU/m². In certain embodiments, wherein the treatment of renal cell carcinoma with ADI-PEG in combination with chloroquine induces an immune response against ADI, the present disclosure provides a method of treating renal cell carcinoma, wherein the dose of ADI is doubled and may be increased to 640 IU/m² per week or more. In one particular embodiment the ADI for the treatment of renal cell carcinoma is modified with 3.5-6.5, or in one embodiment, 4.5-5.5 PEG molecules per ADI. In another embodiment, the present disclosure provides a method of treating renal cell carcinoma by administering rapamycin, or other appropriate mTOR inhibitor, in combination with a composition comprising ADI-PEG 20 wherein the composition comprises an ADI modified with 5±1.5 PEG molecules, and in one embodiment, 5±1.5 straight chain PEG molecules, and, in certain embodiments, the composition comprises less than about 0.5% native ADI (i.e., not modified with PEG) and/or less than about 5% free PEG. In a further embodiment, the composition comprises a histidine-HCL buffer.

In certain embodiments, the present disclosure provides a method of treating, ameliorating the symptoms of, or inhibiting the progression of a cancer in a patient comprising administering to the patient a composition comprising ADI as described herein, wherein the cancer is not melanoma, pancreatic cancer, prostate cancer, small cell lung cancer, mesothelioma, lymphatic leukemia, chronic myelogenous leukemia, lymphoma, hepatoma, or sarcoma.

The present disclosure also provides methods of treating, ameliorating the symptoms of, or inhibiting the progression of an inflammatory disorder in a patient comprising administering to the patient a composition comprising ADI (e.g., ADI-PEG, in particular ADI-PEG 20), as described herein, alone or in combination with one or more other therapeutic agents. In one embodiment, the present disclosure also provides methods of treating, ameliorating the symptoms of, or inhibiting the progression of an inflammatory bowel disease in a patient comprising administering to the patient a composition comprising ADI (e.g., ADI-PEG, in particular ADI-PEG 20), as described herein, alone or in combination with one or more other therapeutic agents. In this regard, the present disclosure provides methods of treating, ameliorating the symptoms of, or inhibiting the progression of Crohn's disease or ulcerative colitis in a patient comprising administering to the patient a composition comprising ADI (e.g., ADI-PEG, in particular ADI-PEG 20), as described herein, alone or in combination with one or more other therapeutic agents.

In another embodiment, the present disclosure provides a method of treating, ameliorating the symptoms of, or inhibiting the progression of a cancer in a patient comprising administering to the patient a composition comprising ADI, and optionally one or more other therapeutic agents, as described herein, wherein the cancer is deficient in ASS, ASL, or both. In this regard, ASS or ASL deficiency may be a reduction in expression as measured by mRNA expression or protein expression, or may be a reduction in protein activity, and generally comprises a statistically significant reduction in expression or activity as determined by the skilled person. Reduced ASS or ASL expression or activity may be a reduction in expression or activity of about 5%, 10%, 15%, 20%, 25%, 30%, 35%, 40%, 45%, 50%, 55%, 60%, 65%, 70%, or more, as compared to expression or activity in an appropriate control sample known to be cancer free. In certain embodiments, ASS or ASL expression or activity is reduced by at least twofold as compared to expression or activity in a non-cancer control sample.

In certain embodiments, the reduced expression or activity of ASS or ASL results from methylation of the ASS or ASL promoter. In another embodiment the reduction in expression or activity of ASS or ASL results from a DNA mutation (e.g., one or more point mutations, small deletions, insertions, and the like) or a chromosomal abnormality resulting in deletion of the gene. In one embodiment, the cancer is ASS or ASL negative, meaning no expression or activity is observed.

Reduction in ASS or ASL expression or activity may be measured using any methods known in the art, such as but not limited to, quantitative PCR, immunohistochemistry, enzyme activity assays (e.g., assay to measure conversion of citrulline into argininosuccinate or conversion of argininosuccinate into arginine and fumarate; e.g., see FIG. 1), and the like.

Thus, the present invention provides methods for treating, ameliorating the symptoms of, or inhibiting the progression of a cancer in a patient comprising administering to the patient a composition comprising ADI as described herein, wherein the cancer exhibits reduced expression or activity of ASS or ASL, or both, wherein the cancer includes, but is not limited to leukemia (e.g. acute myeloid leukemia and relapsed acute myeloid leukemia), melanoma, sarcomas (including, but not limited to, metastatic sarcomas, uterine leiomyosarcoma), pancreatic cancer, prostate cancer (such as, but not limited to, hormone refractory prostate cancer), mesothelioma, lymphatic leukemia, chronic myelogenous leukemia, lymphoma, small cell lung cancer, breast cancer, ovarian cancer, colorectal cancer, gastric cancer (including, but not limited to, gastric adenocarcinoma), glioma, glioblastoma multi-form, retinoblastoma, neuroblastoma, non-small cell lung cancer (NSCLC), kidney cancer (including but not limited to renal cell carcinoma), bladder cancer, uterine cancer, esophageal cancer, brain cancer, head and neck cancers (including, but not limited to, squamous cell carcinoma of the head and neck; cancer of the tongue), cervical cancer, testicular cancer, gallbladder, cholangiocarcinoma, and stomach cancer.

Various studies in the literature have shown that ASS is deficient in the following tumors:

TABLE 1

| ASS-Deficient Tumors | |
|---|---|
| Tumor Type | ASS Deficiency (%) |
| Prostate | 88/88 (100%) |
| Renal | 98/98 (100%) |
|  | 41/45 (91%) |
|  | 31/31 (100%) |
| Lymphoma | 511/532 (96%) |
| Sarcoma | 619/701 (88%) |
| Pancreatic | 41/47 (87%) |
| Acute Myelogenous Leukemia | 46/53 (87%) |
| Small Cell Lung | 7/16 (44%) |
| HCC | 33/44 (75%) |
|  | 20/20 (100%) |
| Melanoma | 119/119 (100%) |
|  | 24/29 (83%) |
|  | 17/27 (63%) |
|  | 20/20 (100%) |
| Bladder | 31/48 (65%) |
|  | 133/242 (55%) |
| Mesothelioma | 52/82 (63%) |
| Gastric | 68/121 (56%) |
| Breast | 46/111 (41%) |
| Non-Small Cell Lung | 28/90 (31%) |
| Glioblastoma | 39/55 (71%) |
| Colorectal | 31 (3%) |
| Ovarian | 23/54 (43%) at diagnosis |
|  | 25/34 (74%) at relapse |

Accordingly, treatment of these ASS-deficient cancers is specifically contemplated herein, with ADI-PEG 20 alone or in combination with other treatments.

The present invention further provides methods for treating, ameliorating the symptoms of, or inhibiting the progression of cancer in a patient comprising administering to the patient a composition comprising ADI as described herein (e.g. ADI-PEG and in particular ADI-PEG 20), in combination with an autophagy inhibitor. In one embodiment, the present invention provides methods for treating cancer in a patient comprising administering to the patient a therapeutically effective amount of a composition comprising ADI as described herein in combination with autophagy inhibitor wherein the cancer is pancreatic cancer or small cell lung cancer.

In certain embodiments, the present invention provides methods of treatment where administration of the compositions comprising ADI described herein depletes arginine in the plasma for at least one month, 2 months, 3 months, 4 months, 5 months, 6 months or longer.

EXAMPLES

Example 1

Arginine Deiminase Reduces the Viability of Argininosuccinate Synthase-Deficient Acute Myeloid Leukemia Cells Acute myeloid leukemia (AML) is the most common leukemia in adults and the second most common leukemia in children, accounting for a significant share of health care costs with ten thousand cases diagnosed per annum in the US alone. Enzyme-based therapy in the form of asparaginase has revolutionized the treatment of acute lymphoblastic leukemia and there is increasing interest in exploiting analogous tractable metabolic defects in AML. Arginine auxotrophic tumors due to deficiency of the rate-limiting enzyme for arginine production, argininosuccinate synthetase (ASS) are susceptible to arginine-degrading enzymes.

In this example, it was determined whether ASS negativity would predict for the efficacy of pegylated arginine deiminase (ADI-PEG 20) using AML cell lines and primary AML samples. A lack of ASS protein was identified in three of seven leukemic cell lines (K562, Kasumi and KG-1) and in all nine samples from patients with cytogenetically normal and abnormal karotype AML. Methylation of the ASS promoter correlated with reduced levels of ASS mRNA and absence of ASS expression. Bone marrow trephines from patients with AML revealed absence of ASS protein in 87% (46/53) of samples by immunohistochemistry, indicating that ASS expression may be used as a biomarker of response to ADI-PEG 20 in vivo. Increased levels of ASS mRNA and detectable ASS protein expression were noted in acute promyelocytic leukemia with the translocation t(15;17).

Significantly, ADI-PEG 20 reduced the viability of ASS-negative AML lines whereas the ASS-positive control lines, Fujioka and U937, were resistant to drug-induced arginine deprivation. Primary ASS-negative AML samples with good engraftment in NOD/SCID mice have been identified and studies of the efficacy of ADI-PEG 20 using this primary AML xenograft model have begun. Based on the results described herein and the potential efficacy with low toxicity of arginine deprivation in humans, a phase II trial of ADI-PEG 20 has been planned in patients with relapsed AML.

Example 2

Inhibition of Autophagy Increases Arginine Deiminase-Induced Cell Death of Argininosuccinate Synthase-Deficient Pancreatic Adenocarcinoma Cells The role of autophagy and its contribution to cell death is controversial. It was hypothesized that autophagy is protective in the setting of arginine deprivation and that inhibition of autophagy by hydroxychloroquine (ChQ) would increase cell death.

The human pancreatic cancer cell line MIA-PaCa2 was treated in vitro and in vivo with pegylated arginine deiminase (ADI-PEG) alone or in the presence of ChQ. Cell death was measured by propidium iodide (PI)-FACS to determine sub-$G_1$ DNA content, and apoptosis was evaluated by Annexin V-PI flow cytometry. Cleavage of caspase 3 was evaluated by western blots and ELISA. Autophagy was measured by evaluating the expression levels of LC3 and nucleoporin p62 (p62) by western blots and ELISA.

In vivo experiments were conducted by generating subcutaneous xenografts in athymic mice followed by intraperitoneal injections of PBS, ADI-PEG, ChQ or a combination of ADI-PEG and ChQ. At sacrifice, tumors were removed for analysis. Tumor lysates were analyzed by western blot for caspase 3 and p62. Immunohistochemistry staining assays for activated caspase 3 and DNA fragmentation (TUNEL) were also performed.

Figure 2A:
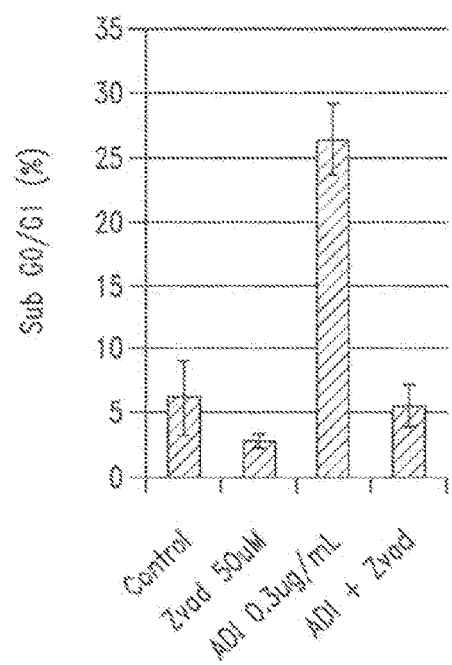
FIGS. 2A-2B show the induction of caspase dependent apoptosis and autophagy of pancreatic cancer cells by ADI in vitro.
Figure 2B:
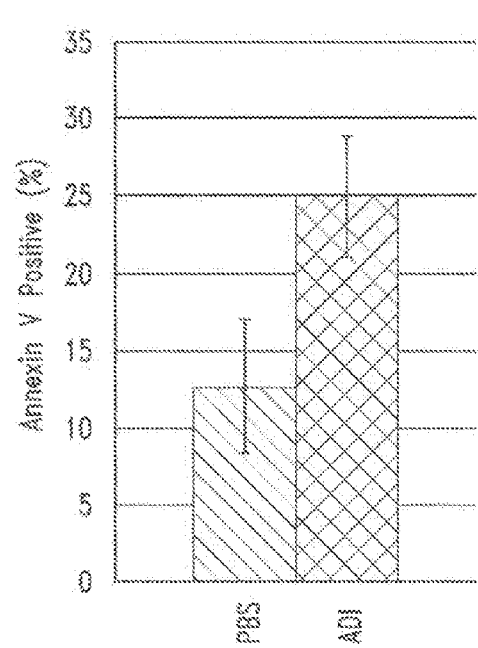

In order to determine if ADI induces apoptosis and autophagy in a caspase dependent manner, cells were incubated with either ADI-PEG or a combination of ADI-PEG and ZVAD-fmk, a pan-caspase inhibitor. As shown in FIG. 2A, incubation with ADI-PEG increased the number of cells in sub-$G_0/G_1$, and this effect was reversible with co-incubation of the pan-caspase inhibitor ZVAD-fmk. Incubation of pancreatic cancer cells in vitro with ADI-PEG (0.3 µg/mL) for 72 hours induced Annexin V depolarization, another apoptosis indicator (FIG. 2B). It was further demonstrated that ADI induces caspase cleavage and LC3B conjugation with PE at 72 hours in a dose dependent manner. These results indicated that ADI induces caspase dependent apoptosis and autophagy in vitro.

Figure 3:
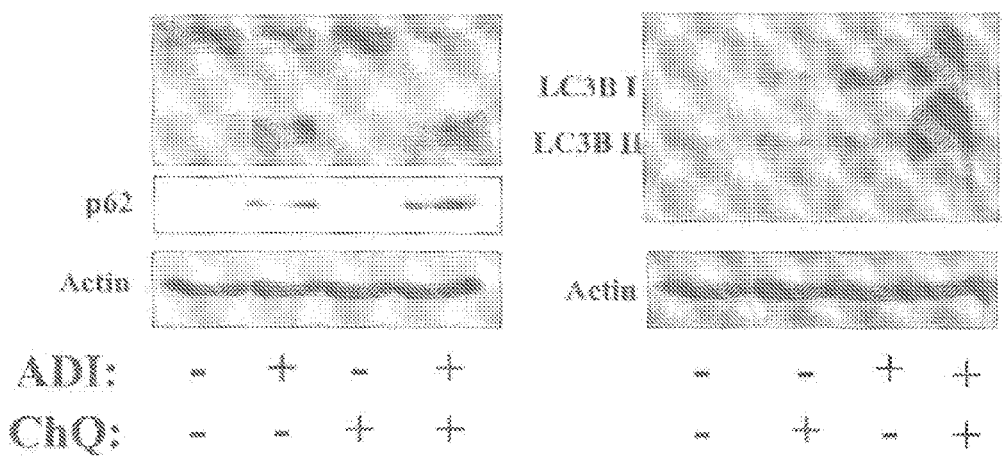
FIG. 3 shows the expression levels of cleaved caspase 3, p62 and LC3B following the incubation of human pancreatic cancer cells with hydroxychloroquine ("ChQ") and/or ADI-PEG.

In order to determine if inhibition of autophagy enhances ADI-induced apoptosis, cells were cultured with ADI-PEG (0.3 µg/mL) with or without ChQ (5 µM) for 72 hours. Western blot analysis revealed an induction of apoptosis by ADI as measured by caspase 3 cleavage (FIG. 3). The levels of p62, LC3B-I, and LC3B-II were measured by western blot analysis in order to examine autophagic flux. The addition of ChQ diminished autophagic flux as shown by an increase in the level of p62 and an increase in the build up of both LC3B-I and LC3B-II (FIG. 3). These results demonstrate that ChQ enhanced ADI induced apoptosis and inhibited autophagic flux in vitro.

Figure 4A:
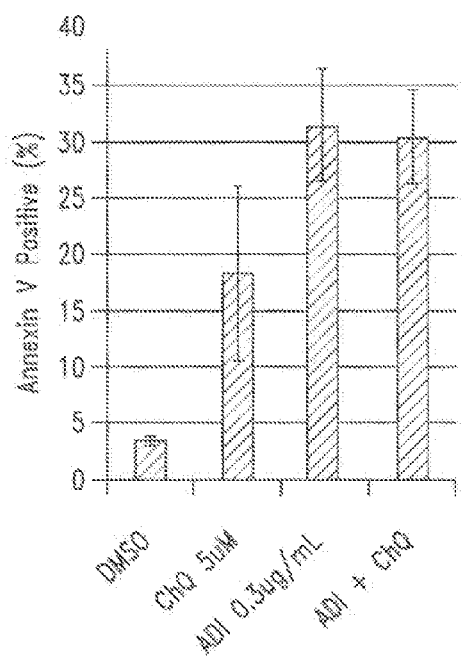
FIGS. 4A and 4B shows the percentage of Annexin V positive cells and sub-G0/G1 cells following the incubation of human pancreatic cancer cells with ChQ and/or ADI-PEG.
Figure 4B:
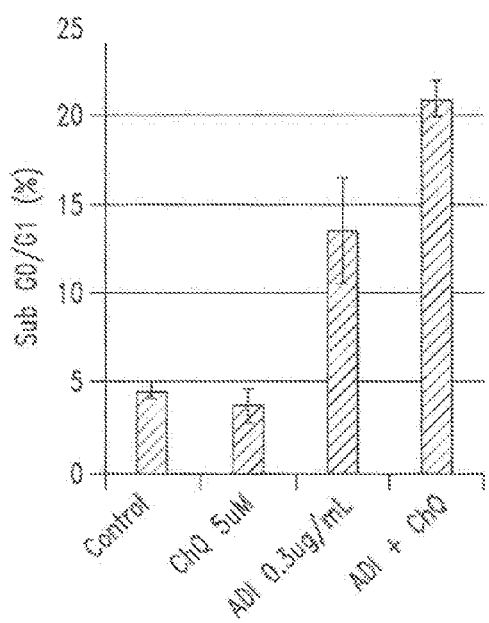

In order to examine whether ChQ alters the amount of apoptotic or non-apoptotic cell death when used in combination with ADI, cells were incubated with ADI-PEG alone or a combination of ADI-PEG and ChQ. Addition of ChQ to the cell culture led to an increase in the percentage of cells in sub-$G_0/G_1$ (FIG. 4B). In contrast, cultures incubated with ADI-PEG and ADI-PEG with ChQ showed a similar percentage of Annexin V positive cells (FIG. 4A). Accordingly, these results indicate that ChQ enhances non-apoptotic cell death in vitro.

Figure 5:
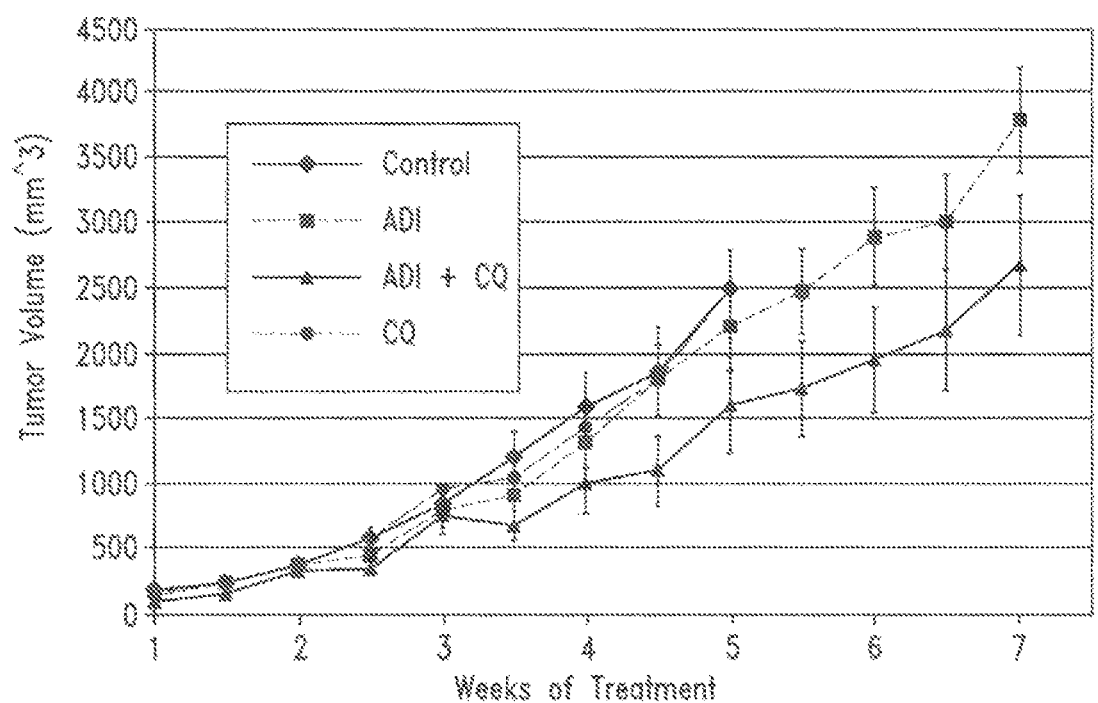
FIG. 5 shows tumor volume in mice following treatment with chloroquine (CQ) and/or ADI-PEG. Subcutaneous xenografts of the human pancreatic cancer cell line MIA PaCa-2 were established in athymic mice.
Figure 6:
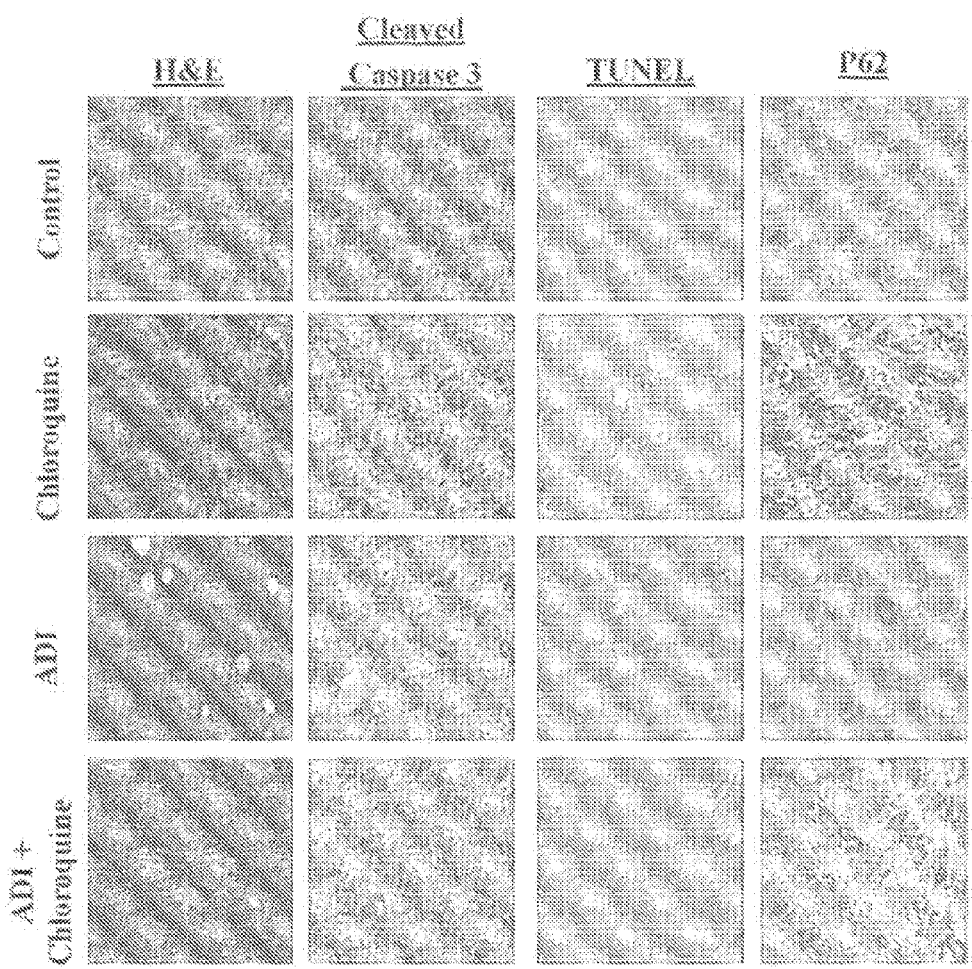
FIG. 6 shows the histopathology of MIA PaCa-2 tumors following treatment with chloroquine and/or ADI-PEG. The first column shows H&E staining, the second column shows staining for active caspase 3, the third column shows staining for DNA fragmentation via the TUNEL assay, and the fourth column shows staining for p62.

In order to assess the effect of ChQ on ADI-dependent tumor growth suppression, subcutaneous xenografts of MIA PaCa-2 were established in athymic mice. Mice were then treated with PBS, ADI-PEG, ChQ, or ADI-PEG+ChQ for up to seven weeks. Tumor volumes were measured twice weekly. As shown in FIG. 5, mice treated with ADI-PEG+ChQ had a significantly smaller tumor volume in comparison to mice treated with ADI-PEG alone. Upon euthanization, tumors were preserved in 10% formalin and stained for markers of apoptosis including active caspase 3, increased p62, and DNA cleavage (FIG. 6). These results demonstrate that a combination of ADI-PEG and ChQ exhibited a synergistic suppression on tumor growth.

In summary, arginine deprivation induced autophagy and cell death in cell lines deficient in ASS. It was shown that autophagy played a protective role in arginine deprivation for pancreatic adenocarcinoma cells, and inactivation of autophagy by hydroxychloroquine resulted in enhanced tumor suppression in vivo.

Example 3

Arginine Deiminase Inhibits Argininosuccinate Synthase-Deficient Small Cell Lung Cancer Tumor Growth Small cell lung cancer (SCLC) is characterized by a strong initial response to chemotherapy, although the majority of patients go on to relapse (Dowell, *Am J med Sci* 339(1):68-76, 2010; Rodriguez and Lilenbaum, *Curr Oncol Rep* 12(5):327-334, 2010). In those patients for whom first-line chemotherapy fails, the chance of response to secondary treatments remains around 10%, and overall survival in these patients is only 3-4 months. Further, current treatment lacks tumor specificity and results in numerous toxicities, and may consequently limit the administration of therapeutics to below the maximally effective dose (Demedts et al, *Eur Respir J* 35(1):202-215, 2010; Dowell, *Am J med Sci* 339(1):68-76, 2010; Rodriguez and Lilenbaum, *Curr Oncol Rep* 12(5):327-334, 2010). This situation highlights the need for the continued development of effective anti-cancer agents with high therapeutic indices.

This example describes the extent of arginine auxotrophy in SCLC and the effectiveness of ADI-PEG 20 arginine therapy in this disease.

Cell Lines, Antibodies and Chemicals

A panel of 10 SCLC was obtained from the cell bank of the Ludwig Institute for Cancer Research, New York Branch at Memorial Sloan-Kettering Cancer Center (MSKCC). Cells were either established at MSKCC or purchased from the American Type Culture Collection (ATCC; Manassas, Va., USA). Cells were grown in RPMI-1640 media supplemented with 10% v/v fetal calf serum, 5% w/v penicillin/streptomycin (penicillin G 5000 units ml$^{-1}$ per streptomycin sulphate 5000 mg ml$^{-1}$) and 1% L-glutamine. Cellular expression of argininosuccinate synthetase (ASS) by western blot was assessed using an anti-ASS antibody (Clone 25, BD Biosciences, San Jose, Calif., USA). LC3B (Cell Signaling, Danvers, Mass., USA), active caspase-3 (Cell Signaling), total caspase-3 (Invitrogen Life Technologies, Carlsbad, Calif., USA) and actin (GeneTex, Irvine, Calif., USA) were used according to the manufacturer's instructions. Topotecan hydrochloride was obtained from Axxora (San Diego, Calif., USA) and chloroquine was obtained from Sigma-Aldrich (St Louis, Mo., USA).

Immunohistochemistry

Tumors and normal tissues were stained using anti-ASS antibody 195-21-1 (LICR, New York, N.Y., USA), as detailed in Jungbluth et al (*Mod Pathol* 23 (Suppl 1):387A, 2010).

Western Blot Analysis

Whole-cell lysates of SCLC cell lines were prepared in RIPA lysis buffer (Tris-HCl 50 mM, 0.05% SDS, 0.5% Na-deoxycholate, NaCl 150 mM, EDTA 5 mM plus protease inhibitor cocktail buffer (Roche Applied Science, Indianapolis, Ind., USA). Protein amounts were determined using the Pierce BCA protein assay (Thermo Fisher Scientific, Rockford, Ill., USA) and equal amounts of proteins were resolved by SDS-PAGE using 4-12% gels (NuPAGE, Invitrogen Life Technologies). Proteins were transferred to PVDF membranes (Millipore, Billerica, Mass., USA), blocked with 5% BSA and probed with appropriate antibodies overnight at 4° C. Following washing, the membranes were then probed with the appropriate secondary antibody before proteins were finally visualized using ECL reagent (Perkin-Elmer, Fremont Calif., USA).

Quantitative-real Time PCR

For RNA extraction, cell pellets were dissolved in 600 µl TRI Reagent solution (Ambion, Austin, Tex., USA), and 60 µl bromochloropane was then added. Approximately two drops of optimum cutting temperature compound (Miles Inc., Elkhart, Ind., USA) was then added to the tube and the mixture was vortexed and left to stand at RT for 2 min. After centrifugation at 14,000 r.p.m. for 10 min, the supernatant was removed to a new tube where an equal volume of 100% isopropanol was added to precipitate the RNA. Following centrifugation at 14,000 r.p.m., the RNA pellet was washed in 75% ethanol and again centrifuged before re-suspension in 50 µl warm water. The RNA concentration was determined using a nanophotometer (Implen Inc., Westlake Village, Calif., USA).

For amplification of cDNA, 1.5 µg RNA was added to a cDNA reaction mixture comprising 10× reaction buffer (Qiagen, Valencia, Calif., USA), 5 mM dNTPase (Qiagen), Oligo DT (Qiagen), reverse transcriptase (Invitrogen Life Technologies) and RNAse Out (Invitrogen) in a total volume of 20 µl. For quantitative-real time (qRT)-PCR reactions, 1.5 µl cDNA was mixed with a reaction mix containing 5 µl SYBRGreen (Invitrogen), 0.02 µl Rox, 0.2 µl primers, and water for a total reaction volume of 10 µl. For ASS, primers were F: 5'-TTTAAGCAGACTAAGGGG-3' (SEQ ID NO:3) and R: 5'-CCAT CCCAGGTTATAAGCACA-3' (SEQ ID NO:4). The qRT-PCR analysis was performed using a 7500 Fast Real-Time PCR system (Applied Biosystems, Carlsbad, Calif., USA), with GAPDH used for normalization of expression. Relative quantification of gene expression (relative amount of target RNA) was determined using the equation $2^{(-\Delta\Delta CT)}$.

Proliferation Assays

To assess the anti-proliferative effect of ADI-PEG 20 on adherent cells, cells were plated a density of $2\times10^3$ cells per well in a tissue culture 96-microwell plate and allowed to adhere overnight. The following day, cells were treated with ADI-PEG 20 (DesigneRx Pharmaceuticals, Vacaville, Calif., USA, a subsidiary of Polaris Group, San Diego, Calif., USA) ranging from 0 to 10 mIU ml$^{-1}$. After incubation for 120 h, cell viability was determined using (3-(4,5-dimethylthiazol-2-yl)-5-(3-carboxymethoxyphenyl)-2-(4-sulfophenyl)-2H-tetrazolium) (MTS, CellTiter 96 AQ$_{ueous}$ One Solution, Promega, Madison, Wis., USA), according to the manufacturers protocol. Twenty microliters of MTS reagent was added to the appropriate control and assay wells before the plate was incubated for 2 h at 37° C. and absorbance read at 490 nm. Absolute absorbance for each treatment was determined by subtracting the background MTS absorbance, and the mean and standard deviation was calculated. The effect of the autophagy inhibitor chloroquine (Sigma) on cell proliferation was assessed using the MTS assay.

To assess the activity of ADI-PEG 20 in non-adherent cells, cells were plated at a density of $1\times10^5$ cells per well in a tissue culture 24-well plate. Additional media was then added containing ADI-PEG 20 for final concentrations ranging from 0-10 mIU ml$^{-1}$. To measure changes in proliferation following incubation with ADI-PEG 20 for 120 h, cells were collected, washed and lysed in RIPA buffer. Total protein for each treatment was then determined using the BSA protein assay as a measure of total cell number. All treatments were performed at least in triplicate.

Propidium Iodide Staining for Sub-G1 Staining

Apoptosis was measured by FACS of propidium-iodide-stained cells as detailed by Riccardi et al (Riccardi and Nicoletti, Nat Protoc 1(3):1458-1461, 2006). Cells were plated in 24-well plates and treated with ADI-PEG 20 for 120 h. Cells were then harvested, washed and fixed in 70% ethanol. DNA was then stained using 20 µg ml$^{-1}$ propidium iodide containing 10 µgml$^{-1}$ DNAse-free RNAse A (Sigma-Aldrich). Cells were then read on a BD FACSCalibur (BD Biosciences) and analyzed using Flow Jo Software (Tree Star, Ashland, Oreg., USA).

Small Interfering RNA Downregulation of ASS

To further assess the importance of cellular ASS expression in response to treatment with ADI-PEG 20, expression of ASS was silenced through the use of ASS-specific siRNA. Small interfering RNA constructs were obtained from Integrated DNA technologies (IDT, Coralville, Iowa, USA) against the ASS-coding region. Only siRNA constructs without any other transcript matches were selected for further experiments.

Argininosuccinate synthetase-positive SW1222 were plated out at a density of $6\times10^5$ cells per dish in 8 ml media in 100 mm tissue culture dishes and allowed to adhere overnight. For transfection, 10 µl of 10 µM ASS siRNA was added to 990 µl Opti-MEM media and 20 µl Lipofectamine 2000 reagent was diluted in 980 µl Opti-MEM media (Invitrogen Life Technologies). These mixtures were incubated for 5 min at RT before being mixed and incubated for a further 20 min at RT. The transfection mixture was then added to the cells and incubated for 24 h at 37° C. At this time, preparations of the transfected cells were lifted from the culture dish, and plated out in 96-well plates in order to assess the effect of ADI-PEG 20 on the growth of the transfected cells. Additional cells incubated for a further 72 h before processing for PCR and western blot analysis.

Arginine Deiminase-PEG20 in vivo Efficacy Study

The ASS-negative SCLC SK-LC-13 was found to be tumorigenic and was subsequently used to determine the efficacy of ADI-PEG 20 in vivo. The activity of ADI-PEG 20 was also assessed in mice bearing ASS-positive NCI-H69 SCLC xenografts. Small cell lung cancer xenografts were established in female BALB/c-nude mice, 3-4 weeks of age weighing ~20 g (Charles River Labs, Wilmington, Mass., USA). To establish the tumors, $10\times10^6$ cells in media were mixed 1:1 with Matrigel High Concentration (BD Biosciences) and injected subcutaneously in the abdominal area of the mice. Tumor growth was regularly measured and tumor volume calculated using the formula (TV=(length×width$^2$)/2). All animal studies were approved by the MSKCC Institutional Animal Care and Use Committee. Mice were euthanized when tumors reached an approximate volume of 1,000 mm$^3$.

The anti-tumor efficacy of ADI-PEG 20 was simultaneously assessed in mice bearing either moderate or large SK-LC-13 SCLC xenografts. In the first study, treatment was initiated once tumors had reached an average size of 125 mm$^3$. In the large xenograft study, treatment was initiated once tumors had reached an average size of 500 mm$^3$. Arginine deiminase-PEG20 was administered at doses of 1, 2 and 5 IU per animal once every 5 days for 20 days (five doses). To assess the effect of sustained dosing, further groups (n=5) at all dose levels received continued administration of ADI-PEG 20 every 5 days until tumors progressed to the 1,000 mm$^3$ size limit. Additionally, the efficacy of ADI-PEG 20 was assessed in mice bearing ASS-positive NCI-H69 xenografts. Here, mice received five doses of 2 IU ADI-PEG 20 for 20 days once tumor had reached an average size of 150 mm$^3$. Arginine deiminase-PEG20 was administered by intraperitoneal injection in all studies. The specific activity of ADI-PEG 20 used in these studies is 9 IU mg$^{-1}$ of protein. Thus, 1 IU of ADI-PEG 20 per 20 g mouse is equivalent to 160 IU m$^{-2}$.

Measurement of Serum Arginine and Citrulline

In order to determine the effect of ADI-PEG 20 treatment on systemic arginine levels, mice sera were analyzed using high-performance liquid chromatography (HPLC). L-arginine and L-citrulline were resolved with a Pickering Laboratories PCX 5200 post-column derivatization instrument (Pickering Laboratories, Mountain View, Calif., USA) at 39° C. reaction temperature and a fluorescence detector. All reagents, including the buffer and column, were used as suggested by Pickering Laboratories. Total ADI-PEG 20 levels were measured by ELISA, as described previously (Holtsberg et al, *J Control Release* 80(1-3):259-271, 2002).

Statistical Analysis

Efficacy of ADI-PEG 20 treatment in vivo was assessed by comparing means of control and treatment groups using unpaired two-tailed t-tests at the termination of control groups using GraphPad Prism (Version 5.0, GraphPad Software Inc., La Jolla, Calif., USA). A 95% confidence level was used, with mean tumor volume declared significantly different if P<0.05.

Results

SCLC Frequently Lack Expression of ASS

As the lack of ASS expression is generally associated with sensitivity to ADI, its expression was assessed in human SCLC tumors. As shown in FIG. 7C, an initial immunohistochemistry (IHC) analysis of human SCLC tumors revealed that some SCLC had a near total lack of ASS expression. Approximately 45% (7 out of 16) of tumors in this initial analysis demonstrated little or no ASS expression. On the contrary, robust expression of ASS was apparent in normal tissues such as skin (FIG. 7A) and other cancers such as colon carcinoma (FIG. 7B; Jungbluth et al, *Mod Pathol* 23 (Suppl 1):387A, 2010).

Figure 7D:
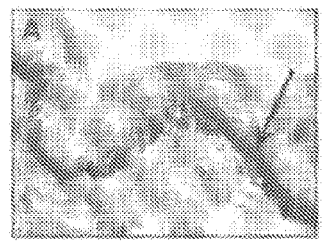
Figure 7D:
Figure 7D:
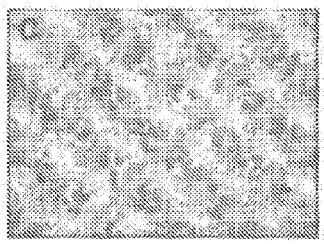
Figure 7D:
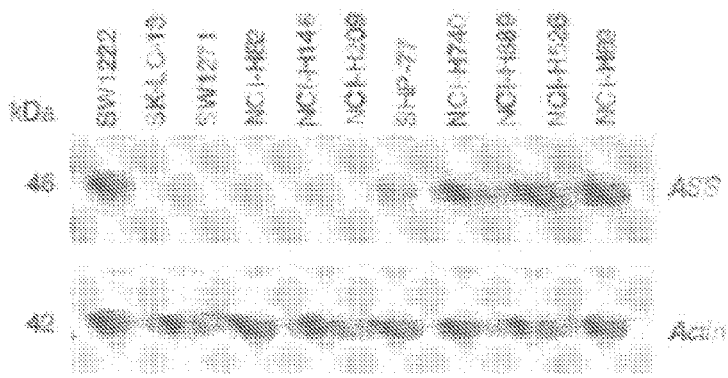
Figure 7E:
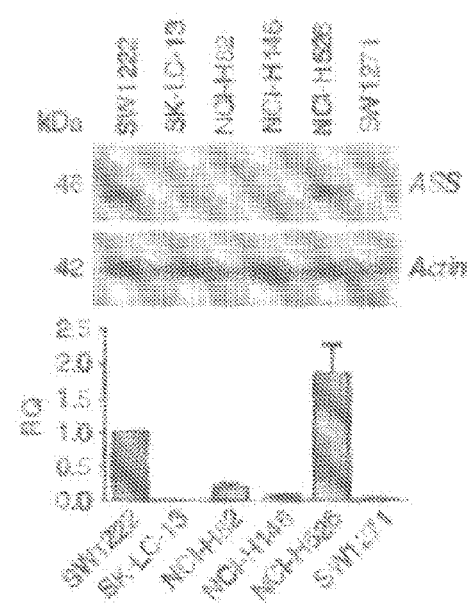

As the initial immunohistochemical analysis has shown a frequent loss of ASS expression in SCLC human tumors, the expression status of ASS in a panel of SCLC cell lines was assessed. Western blot analysis revealed that 5 out of 10 (50%) of the tested SCLC cell lines lacked significant expression of ASS at the protein level (FIG. 7D). The cellular expression of ASS as detected by western immunoblotting was similar using both the Clone 25 and 195-21-1 anti-ASS antibodies (data not shown). Analysis of mRNA levels using qRT-PCR demonstrated a general correlation between ASS mRNA and protein expression levels (FIG. 7E).

Figure 8A:
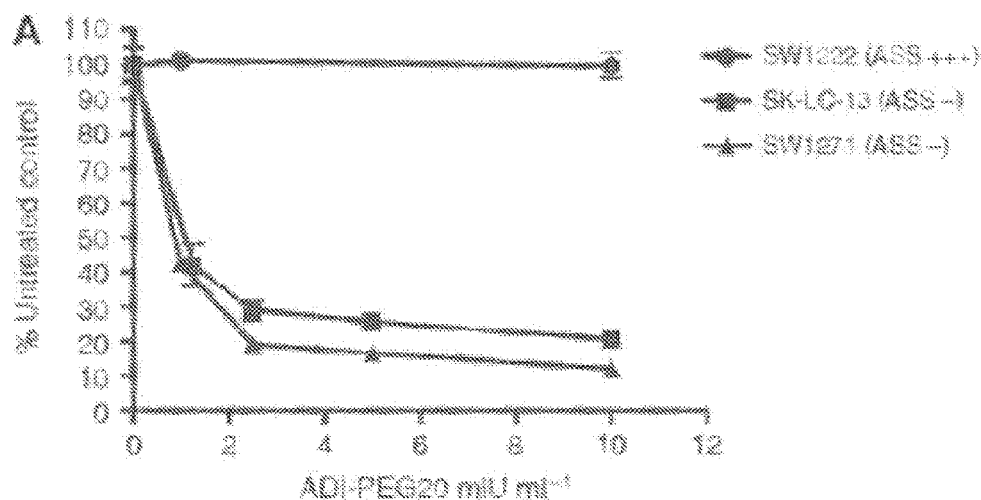
FIGS. 8A-8B show the inhibition of the in vitro proliferation of ASS-negative small cell lung cancer cells by ADI-PEG 20. Adherent (FIG. 8A) and non-adherent (FIG. 8B) cells were treated with ADI-PEG 20 for 120 hours before proliferation was assayed using the MTS assay for adherent cells or the BCA total protein assay for non-adherent cells.
Figure 8B:
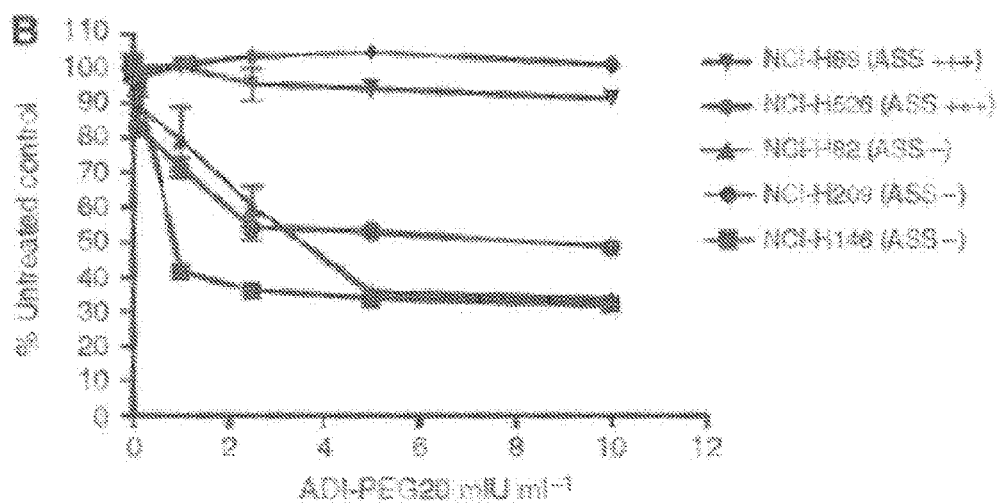

Arginine Deiminase-PEG20 Inhibits the Proliferation of ASS-negative SCLC Cell Lines in vitro The effect of ADI-PEG 20 on cell proliferation in vitro was assessed in both ASS-positive SCLC cells and those lacking expression of the enzyme. Cells with both adherent and non-adherent growing tissue culture characteristics were included in these experiments. A clear dose-dependent decrease in proliferation was found in the adherent ASS-negative SCLC cell lines SK-LC-13 and SW1271. No effect was apparent on the growth of the adherent ASS-positive colon carcinoma cell line SW1222 (FIG. 8A). As for non-adherent cells, ASS-positive cells demonstrated almost total resistance to the anti-proliferative effects of ADI-PEG 20, whereas a relative decrease in proliferation was again observed in ASS-deficient cells following ADI-PEG 20 treatment (FIG. 8B). As the ADI-PEG 20-sensitive cell line SK-LC-13 was determined to be tumorigenic, it was chosen to be a model cell line for later experiments in vitro and in vivo.

Arginine Deiminase-PEG20 Induces Autophagy and Caspase-independent Apoptosis

Figure 9F:
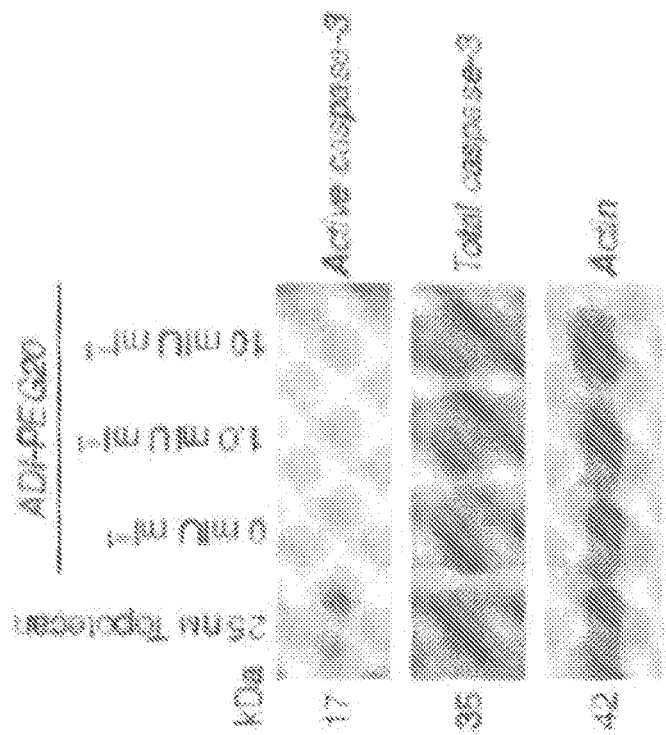
Figure 9E:
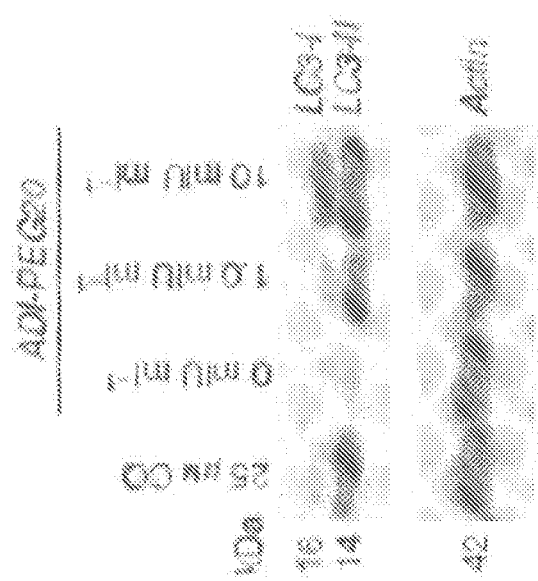
Figure 14:
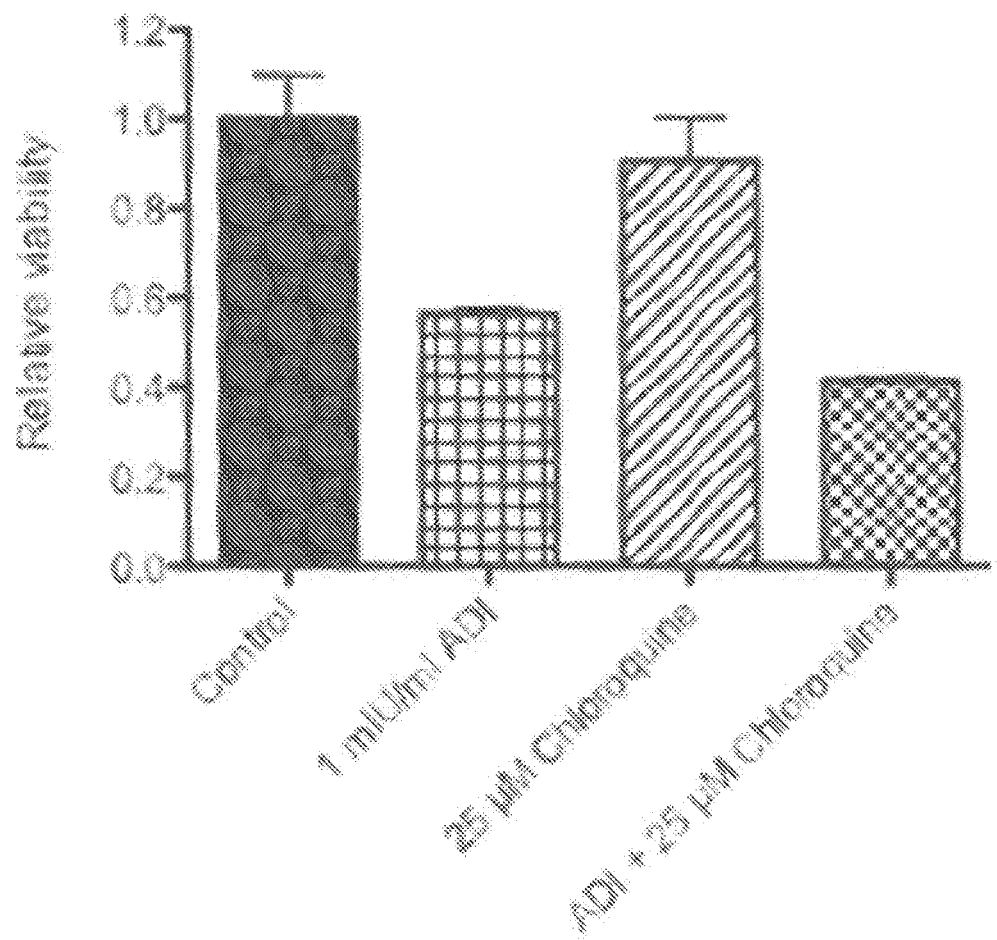
FIG. 14 shows the relative cell liability relative to respective in vitro treatments with ADI-PEG 20 and autophagy inhibitor chloroquine.

As with more general nutrient starvation, the depletion of intracellular arginine by ADI has been observed to induce metabolic stress and subsequent cellular autophagy (Kim et al, *Cancer Res* 69(2):700-708, 2009; Savaraj et al, *Curr Mol Med* 10(4):405-412, 2010). An assay for the formation of the autophagy-related protein LC3-II assessed if treatment with ADI-PEG 20 was able to induce cellular autophagy in SCLC. Although some basal expression of LC3-II expression was observed in SK-LC-13, treatment with ADI-PEG 20 resulted in a clear increase in the detectable cellular level of the protein (FIG. 9E). Chloroquine is a known inhibitor of autophagy that disrupts normal lysosomal functions, and thus results in an increase in the cellular level of LC3-II. Subsequently, cells treated with chloroquine as a positive control demonstrated very robust expression of LC3-II. Combined treatment of cells with ADI-PEG 20 and chloroquine resulted in a small but significant (P=0.008) decrease in viability relative to individual treatments, suggesting that inhibition of autophagy may enhance the efficacy of ADI-PEG 20 (FIG. 14).

In order to determine the possible mechanism of the anti-proliferative effects of ADI-PEG 20 a FACS analysis of apoptosis by sub-$G_1$ DNA content was performed. Cells were treated for 72 h before the analysis was performed. Little apoptosis was detectable in untreated cells, while 25 nM topotecan, used as a positive control, was observed to cause apoptosis in around 45% of the SK-LC-13 cells (FIGS. 9A and B). Although not as effective as topotecan, incubation with 1.0 and 10 mIU ml$^{-1}$ ADI-PEG 20 resulted in the induction of apoptosis in ~6% and 16% of cells, respectively (FIGS. 9C and D). Although apoptosis was apparent by sub-$G_1$ DNA content, no activation of caspases were observed following treatment of cells with ADI-PEG 20 in contrast to topotecan-treated cells (FIG. 9F).

Silencing of ASS Expression Induces Sensitivity to ADI-PEG 20

Figure 10A:
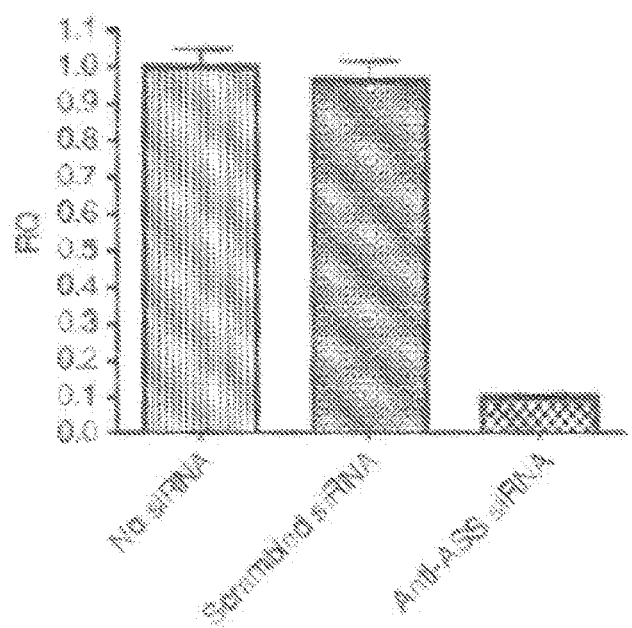
FIGS. 10A-10C show the silencing of ASS expression with siRNA.
Figure 10B:
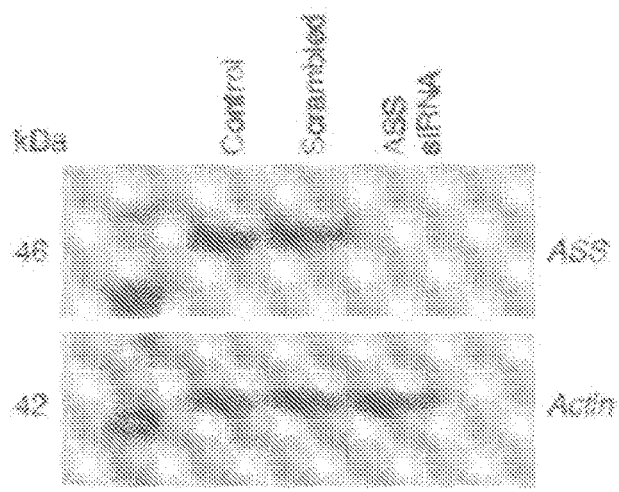
Figure 10C:
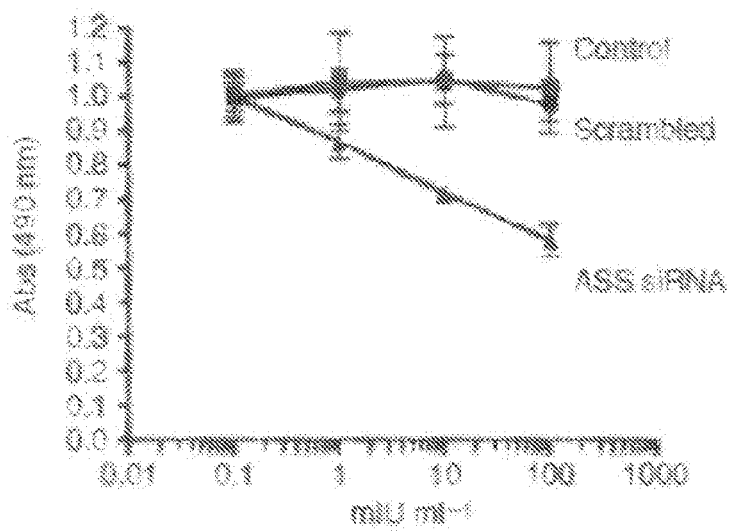

Following transfection with ASS-specific siRNA, the relative expression of ASS in ASS-positive cell lines was assessed with Real Time PCR. As shown in FIG. 10A, transfection with ASS siRNA reduced ASS mRNA levels by ~90% after 72 h incubation. Simultaneous western blot analysis demonstrated a robust reduction in the expression of ASS protein levels in cells treated with ASS-specific siRNA (FIG. 10B). However, some expression of ASS remained under these conditions. Examination of cell viability using the MTS assay demonstrated that ASS-positive cells treated with ASS siRNA became sensitive to ADI-PEG 20-induced arginine deprivation, resulting in reduced cell viability, whereas no decrease in viability was observed in control or scrambled siRNA-treated cells (FIG. 10C).

Arginine Deiminase-PEG20 Inhibits the Growth of SCLC Xenografts

Figures 11A, 11B:
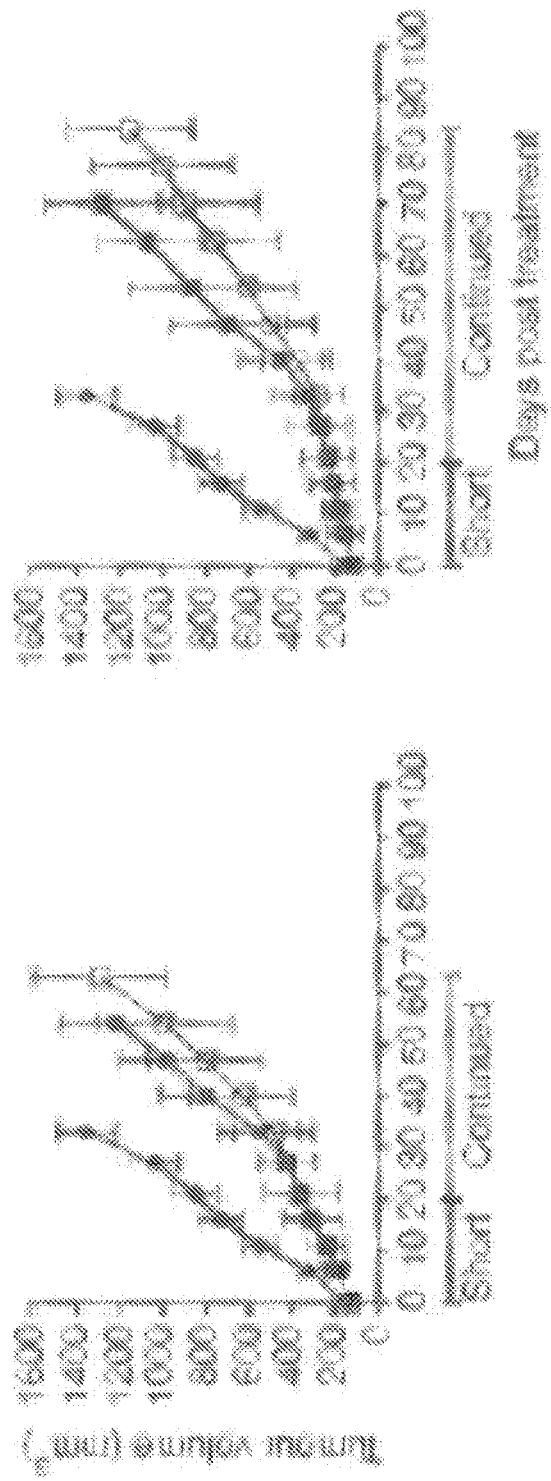
Figure 11D:
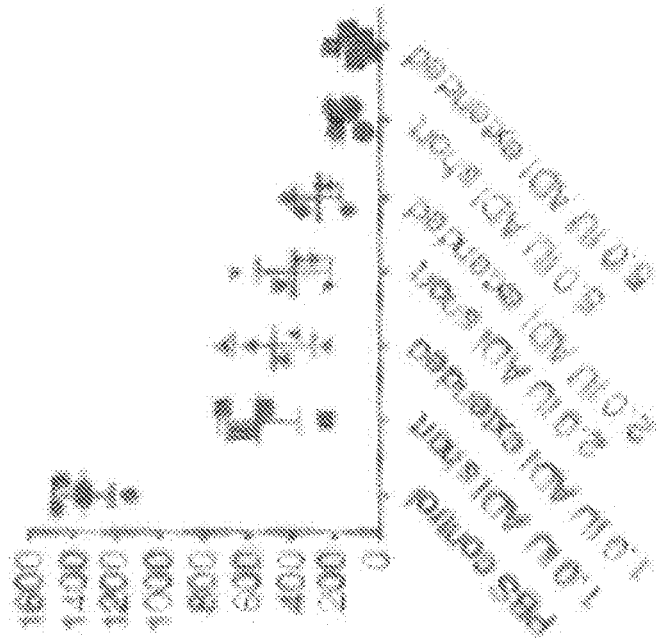
Figure 11C:
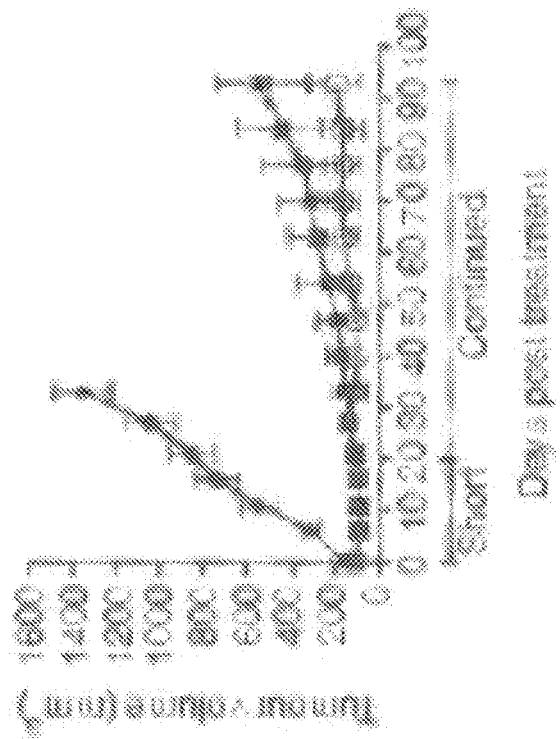
Figure 12:
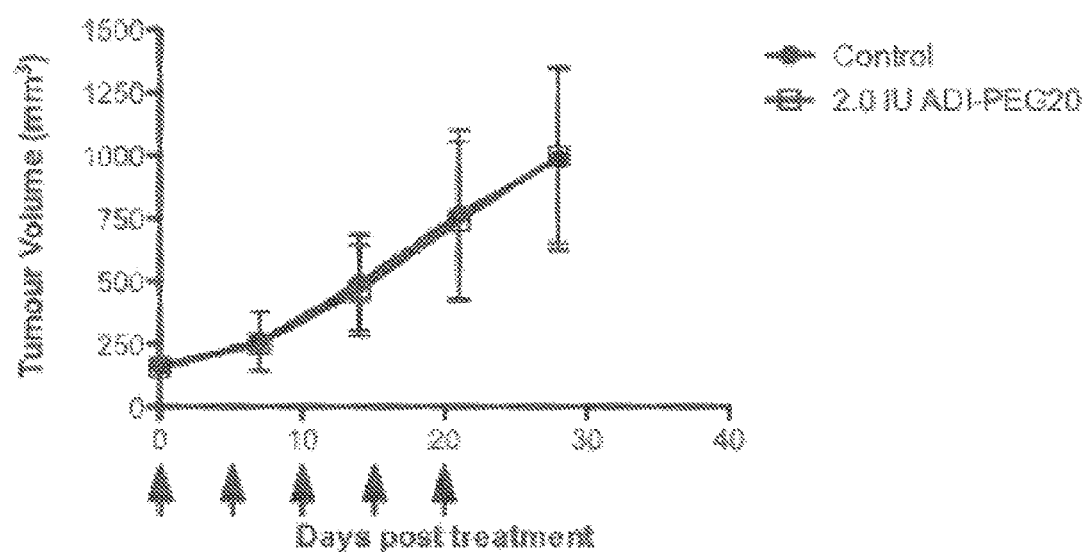
FIG. 12 shows the growth curve of tumor volumes of ASS positive NCI-H69 small cell lung cancer xenografts in BALB/c nude mice. Mice received PBS vehicle or 2 IU ADI-PEG 20 per mouse (black arrows).

The anti-tumor efficacy of systemic treatment with ADI-PEG 20 in vivo was assessed in BALB/c-nude mice bearing human SCLC xenografts. Separate studies were performed in mice with established tumors around 125 mm$^3$, and in mice bearing larger (~500 mm$^3$) tumors at the start of treatment. In mice bearing moderately sized SK-LC-13 xenografts (124.6±37.1 mm$^3$), ADI-PEG 20 caused a significant and dose-dependent reduction in tumor growth relative to control mice (FIGS. 11A-C). Control mice were euthanized at day 33 due to excessive tumor volume, at that time the mean tumor volume of control mice was significantly larger than those in the ADI-PEG 20-treated mice groups, regardless of the dose or treatment schedule (P>0.0001 for all treatment groups; FIG. 11D). At completion of the study, tumors treated with continued dosing of 5 IU ADI-PEG 20 every 5 days were significantly smaller than those dosed every 5 days for only 20 days (P=0.0063). However, this effect was not observed at the 1 and 2 IU dose levels, as tumor growth proceeded at a comparable rate in groups receiving short and continued dosing. Subsequently, the mean tumor volumes of mice receiving short or continued ADI-PEG 20 dosing were not significantly different at the termination of respective short dosing groups due to excessive tumor volume (1 IU: P=0.251; 2 IU: P=0.084). Treatment of ASS-positive NCI-H69 SCLC xenografts with ADI-PEG 20 did not produce any effect on tumor growth (FIG. 12).

Analysis of serum from these mice before (day 0), during (day 12) and after (day 40) initial dosing of ADI-PEG 20 reveals that ADI-PEG 20 serum levels were dose dependent (FIG. 11E). In mice where ADI-PEG 20 was only administered up to day 20, serum levels of the enzyme were observed to return to baseline levels by day 40, consistent with the ~7 day half-life of ADI-PEG 20 in the mice (Ensor et al, *Cancer Res* 62(19):5443-5450, 2002; Holtsberg et al, *J Control Release* 80(1-3):259-271, 2002). Further, this short course of treatment only temporarily depleted serum arginine, as expected, which subsequently returned to normal levels 20 days after the last dose (day 40) without further dosing of ADI-PEG 20 (FIG. 11F). Citrulline levels rose in a dose-dependent relationship to arginine, with a shorter course of ADI-PEG 20 correlating with a return of citrulline levels to baseline (FIG. 11G). Citrulline levels increased with extended dosing at the 1 IU level, consistent with systemic arginine remaining and being metabolized to citrulline, despite arginine serum levels being below the limits of detection. Little increase in citrulline levels was observed with continued dosing at the 2 and 5 IU dose levels.

Figures 13A, 13B:
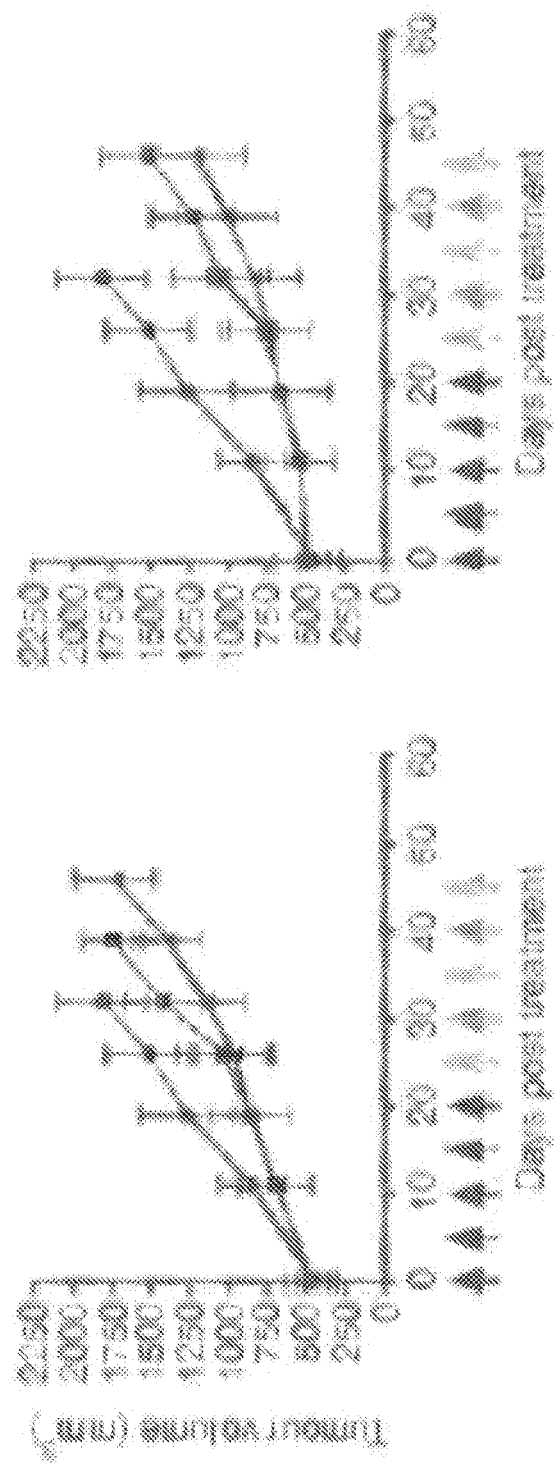
FIGS. 13A-13D show the inhibition of large SK-LC-13 small cell lung cancer xenografts in BALB/c-nude mice. Growth curves of tumor volumes from mice receiving PBS vehicle (circle), a short 20 day course of ADI-PEG 20 (black arrows) (square), or continued dosing of ADI-PEG 20 (grey arrows) (triangle) at doses of 1 IU per mouse (FIG. 13A), 2 IU per mouse (FIG. 13B), and 5 IU per mouse (FIG. 13C) are shown. Tumor volumes at termination of the control group on day 32 are shown in FIG. 13D.
Figure 13D:
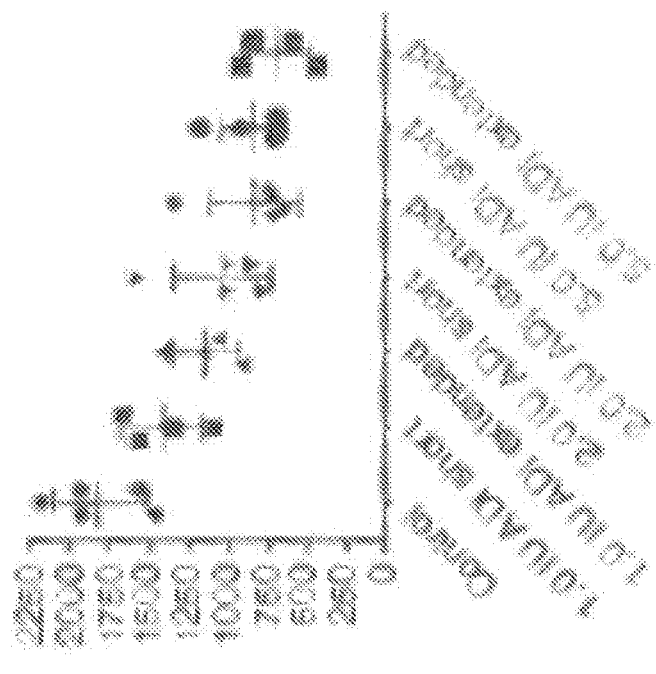
Figure 13C:
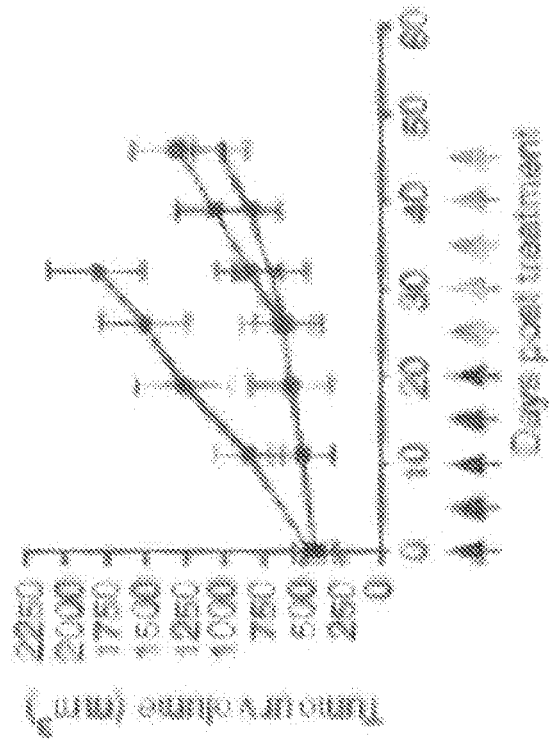

In the second study of ADI-PEG 20 in vivo, treatment was begun when tumors had grown to a relatively large size of 473.4±161.0 mm$^3$. A dose-dependent inhibition of tumor growth was again observed (FIGS. 13A-C), although this was not as significant as that observed in animals bearing smaller xenografts. Tumor volumes where compared at termination of the control cohort on day 32 of this study (FIG. 13D). Continued treatment with 1 IU ADI-PEG 20 was able to significantly reduce the tumor volume relative to control mice (P=0.007), while a short-course treatment did not result in a statistical significant reduction on tumor size (P=0.07). Further, continued dosing was observed to cause a moderately significant (P=0.26) reduction in tumor volume relative to the short-course treatment, as assessed at termination of the short-treatment group at day 39. At higher doses of ADI-PEG 20, significant reduction of tumor volume relative to untreated controls was observed with both short (P=0.004) and continued (P=0.0007) administration at the 2 IU level, and also in both the short (P=0.0003) and continued (P=0.0001) schedules at the 5 IU dose level. However, continued dosing did not significantly improve responses at these doses relative to short-course treatment.

In summary, this example demonstrates that a large proportion of SCLCs lack the expression of ASS, and that ASS-negative SCLC are sensitive to arginine deprivation therapy. Although the frequency of ASS deficiency does not equal the almost total absence of expression as reported in melanoma, it remains that 50% of the nearly 30,000 new cases of SCLC reported in the United States each year may be susceptible to arginine deprivation therapy.

In vitro studies using both adherent and non-adherent ASS-deficient SCLC cell lines demonstrated that ADI-PEG 20 caused dose-dependent antiproliferative efficacy. The results described herein indicate that loss of ASS protein is associated with the anti-proliferative effects of ADI-PEG 20 in otherwise identical cells and further validates the relative sensitivities observed in SCLC cancers of differing ASS expression. As inhibition of cyto-protective autophagy may potentiate the antiproliferative effects of ADI-PEG 20, the combination of ADI-PEG 20 with 25 mM of the autophagy inhibitor chloroquine was assessed in vitro (Kim et al, *Cancer Res* 69(2):700-708, 2009). However, the combination only induced a moderate, albeit significant (P=0.008), increase in the antiproliferative effect of ADI-PEG 20 in SCLC cells (FIG. 14). Treatment of SCLC with ADI-PEG 20 caused a moderate increase in the population of cells in sub-$G_1$ peak following staining with propidium iodide, suggesting that these cells had undergone apoptosis. Western blot analysis revealed that ADI-PEG 20 did not cause caspase activation in SK-LC-13 SCLC cells. Without wishing to be bound by theory, the overall cellular response to arginine deprivation induced by ADI-PEG 20 in SCLC cells appears to operate through a complex mechanism involving an initial metabolic response seen in the induction of autophagy, followed by caspase-independent cell death.

In vivo studies in mice revealed that growth of SK-LC-13 xenografts was abrogated by ADI-PEG 20 in a dose-dependent manner. Significant anti-tumor activity was observed at the 1, 2 and 5 IU dose per animal doses. Importantly, although more robust inhibition of tumor growth was observed in mice bearing smaller (~120 mm$^3$) established tumors, ADI-PEG 20 also demonstrated significant anti-tumor efficacy in mice bearing large (~500 mm$^3$) xenografts. Although direct comparison with other tumor types is difficult, the anti-tumor efficacy observed with ADI-PEG 20 in SCLC xenografts is similar and possibly superior to that observed using equivalent doses of ADI-PEG 20 in different tumor types including renal and prostate cancer xenografts.

Example 4

Arginine Deiminase Inhibits Growth of Ass-Deficient Metastatic Sarcomas

While sarcomas are a rare group of tumors, the poor response to current clinical regimens represents an important unmet need in oncology. A better therapeutic understanding of the biology and metabolism of sarcoma growth is necessary to develop novel therapies to treat patients with this group of tumors. Argininosuccinate synthase (ASS) is the rate-limiting enzyme in the conversion of citrulline to arginine. When ASS is not expressed, arginine becomes an essential amino acid to a cancer cell that must be delivered from the diet.

Immunohistochemical analysis of 701 patient specimens representing 45 subtypes of sarcoma demonstrated that ASS is not expressed in over 85% of sarcomas (619 of 701 patient samples). This suggested that sarcomas are sensitive to the arginine deprivation therapy using pegylated arginine deiminase (ADI-PEG 20).

Treatment of a panel of leiomyosarcoma, osteosarcoma, alveolar soft part sarcoma, malignant peripheral nerve sheath tumor and Ewing's sarcoma cell lines with ADI-PEG 20 resulted in cell cycle arrest but not apoptosis when ASS expression was low, whereas the ASS high osteosarcoma cell line MG63 continued to divide. Response in sarcoma cell lines was dependent on ASS expression, as bone sarcomas, soft tissue sarcomas, complex cytogenetic sarcomas and translocation dependent sarcomas all demonstrated cell cycle inhibition upon treatment with ADI-PEG 20. The IC50 for cell lines treated with ADI-PEG 20 ranged from 0.02-0.1 µg/mL in sensitive cell lines with low expression of ASS.

Treatment of sarcomas that lack ASS with ADI-PEG 20 induced autophagy. Depletion of arginine by ADI-PEG 20 in ASS deficient sarcomas when combined with chloroquine, an inhibitor of autophagy, induced cell death as measured by Annexin V.

Xenograft of the ASS low expressing osteosarcoma cell line MNNG into nude mice followed by treatment with ADI-PEG 20 demonstrated a significantly slower tumor growth rate as compared to PBS treated controls.

With regard to the above examples, it should be noted that in a renal cell carcinoma xenograft model, it was observed that ADI-PEG 20 plus the autophagy inhibitor, hydroxychloroquine, did not result in an additive effect. Therefore the effect of ADI-PEG 20 plus autophagy inhibitors in any particular cancer is not predictable, further highlighting the surprising effects of the present disclosure.

Example 6

Figure 15:
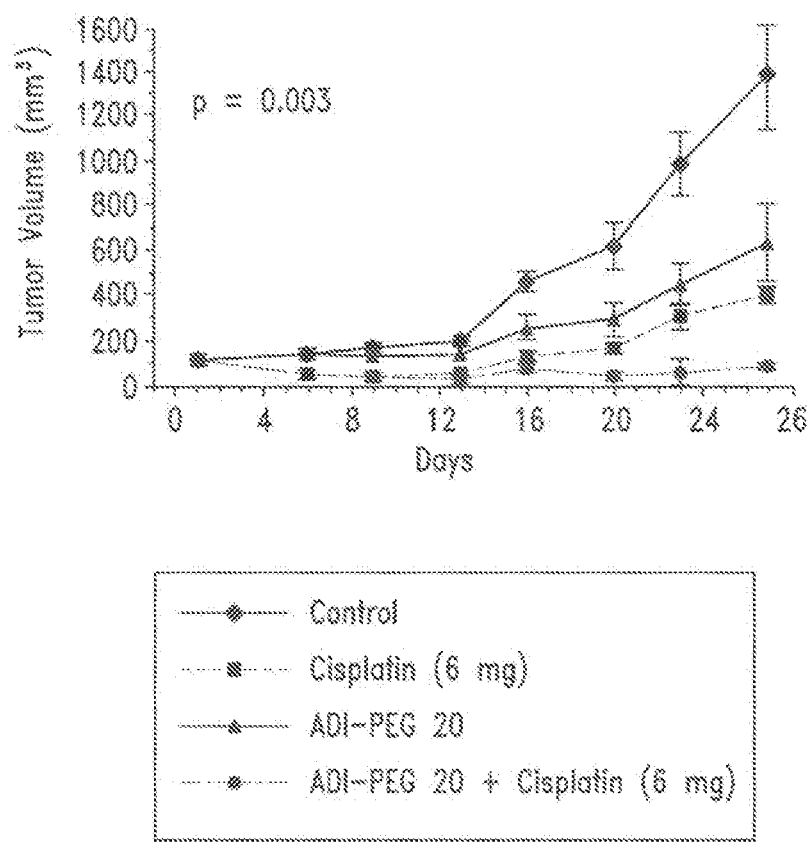
FIG. 15 shows a graph of xenograft data demonstrating that the combination of ADI-PEG 20 and cisplatin results in enhanced anti-tumor activity in ASS deficient melanoma cells.

ADI-Peg 20 Combined with Cisplatin Significantly Enhances Antitumor Activity In Vivo Xenograft testing was also performed to evaluate in vivo efficacy of ADI-PEG 20 in combination with cisplatin. ADI-PEG 20 was evaluated in vivo for therapeutic efficacy, either as a single agent or in combination with cisplatin in the treatment of two different human melanoma xenograft models in nude mice. The cisplatin dose was 6 mg/kg or 18 mg/m$^2$ (Km=3) intraperitoneal (IP) given every 6 days×3 doses. This same dose, extrapolated to humans, would be 40 mg/m$^2$ (Km=40), or a total dose of 120 mg/m$^2$ over 3 weeks. ADI-PEG 20 was given at 53.3 IU/kg every 6 days IM×4 doses. This same ADI-PEG 20 dose, extrapolated to humans, would be 160 IU/m2 or 18 mg/m2. As shown in FIG. 15, treatment with ADI-PEG 20 and cisplatin combination showed significantly enhanced activity compared to either agent alone. Thus, xenograft data showed that the combination of ADI-PEG 20 and cisplatin results in enhanced tumor activity in ASS deficient melanoma cells, even when the cisplatin was administered over a limited period of time.

Example 7

Phase I Human Study of ADI-Peg 20 Combined with Docetaxel

A single-center, open-label, phase I dose escalation study was initiated to determine the maximum tolerable dose and dose limiting toxicity (MTD and DLT) of ADI-PEG 20 in combination with docetaxel administered intravenously (IV) every three weeks to patients with advanced solid tumors. Patients received ADI-PEG 20 intramuscularly (IM) weekly at escalating doses followed 1 hour later (on day 1) by docetaxel 75 mg/m2 IV. Cycle length is 21 days. ADI-PEG 20 was continued as a weekly IM injection throughout. Dose escalation occurred using a standard 3+3 design. Each new dose level cohort was entered 21 days after the last subject was entered in the prior cohort. 18 mg/m2 is approximately equivalent to 160 IU/m2.

The dosing regimen is summarized in Table 2 below.

TABLE 2

Docetaxel + ADI-PEG 20 Dosing Regimen

| Dose level | Docetaxel (mg/m$^2$) | ADI-PEG 20 (mg/m$^2$) |
|---|---|---|
| −1* | 75 | 2.2 |
| 1 | 75 | 4.5 |
| 2 | 75 | 9 |
| 3 | 75 | 18 |
| 4 | 75 | 36 |

*Trial will start at level 1 and will de-escalate to level −1 if DLT observed.

The treatment schema is summarized in Table 3 below.

TABLE 3

Treatment Schema

| | Day 1 Cycle 1[1] | Day 8 Cycle 1[1] | Day 15 Cycle 1 | Day 22 Cycle 2+ |
|---|---|---|---|---|
| Docetaxel[2] | X | | | X |
| ADI-PEG 20[3] | X | X | X | X |

[1] 1 cycle equals 21 days
[2] docetaxel IV administration on day one of each cycle (infused over 30 min.)
[3] ADI-PEG 20 is given intramuscularly once a week Initial results from this study are summarized in Table 4 below. In particular, of 8 subjects treated to date with information available, the objective clinical benefit results are as follows:

TABLE 4

Summary of Study Results

| Tumor | Best Response | Duration on Treatment |
|---|---|---|
| Lung-nonsmall cell | Stable Disease | 33 weeks |
| Lung-nonsmall cell | Stable Disease | 12 weeks |
| Tongue (head & neck) | Stable Disease | 12 weeks |
| Tongue (head & neck) | Partial Response (to be confirmed) | 12 weeks |
| Prostate | Stable Disease | 8 weeks |

Thus 6 of 8 (75%) of the patients enrolled to date have clinical benefit (stable disease+partial response+complete response).

The doses being used in this study are low doses, as 18 mg/m$^2$ has been used in Phase 3 hepatocellular carcinoma studies, and 36 mg/m$^2$ has shown effectiveness in melanoma. Accordingly, this early data is quite encouraging given the positive response even at this low dose and suggests that the combination of ADI-PEG 20 with Docetaxel is an effective cancer treatment. In particular, docetaxel is approved in the US for treatment of tumors in breast cancer, non-small cell lung cancer, hormone refractory prostate cancer, gastric adenocarcinoma, and squamous cell carcinoma of the head and neck cancer. Furthermore, it has been used in treatment of sarcomas, especially uterine leiomyosarcoma, and over variant cancer. As such, treatment of these cancers with docetaxel in combination with ADI-PEG 20 is specifically contemplated herein.

Example 8

ADI-Peg 20 Plus Rapamycin Demonstrates Synergistic Effect in In Vivo Xenograft Model of Renal Cell Carcinoma A mouse xenograft model was used to study the effects of ADI-PEG 20 alone and in combination with rapamycin for the treatment of renal cell carcinoma.

The activity of ADI-PEG 20 was assessed in mice bearing Caki-1 (ATCC No. HTB-46™) xenografts. Renal cell carcinoma Caki-1 xenografts were established in female BALB/c-nude mice, 3-4 weeks of age with a body weight of 20 g (SLAC, Shanghai, China). To establish the tumors, 5×10⁶ cells in media were mixed 1:1 with Matrigel High Concentration (BD Biosciences) and injected subcutaneously in the abdominal area of the mice. Tumor growth was regularly measured and tumor volume calculated using the formula (TV=(length×width$^2$)/2). When tumors reached an approximate volume of 125 mm$^3$, ADI-PEG20 was administered at doses level of 160, 320 and 640 IU/m$^2$ once every week for four weeks by intramuscular injection. Each study group had 9 mice. Mice were euthanized when tumors reached an approximate volume of 1100 mm$^3$. The results indicated that ADI-PEG 20 inhibited tumor growth in a dose dependent manner. More than 80% tumor inhibition was achieved when 640 IU/m$^2$ was used.

In an additional experiment, the activity of ADI-PEG 20 as either a single agent or in combination with rapamycin was assessed in mice bearing Caki-1 xenograft. Renal cell carcinoma xenografts were established in female BALB/c-nude mice, 3-4 weeks of age weighing about 20 g (SLAC, Shanghai, China). To establish the tumors, 5×10⁶ cells in media were mixed 1:1 with Matrigel High Concentration (BD Biosciences) and injected subcutaneously in the abdominal area of the mice. Tumor growth was regularly measured and tumor volume calculated using the formula (TV=(length×width$^2$)/2). When Caki-1 xenografts reached an approximate volume of 125 mm$^3$, mice were randomly divided into 6 groups with 8 animals per group and the treatments were initiated according to the following protocol: Group 1 received 40 μL PBS once every week for four weeks by intramuscular injections, group 2 received ADI-PEG 20 (320 IU/m$^2$) once every week for four doses by intramuscular injections, group 3 received rapamycin (0.5 mg/kg) once every day for 21 days by i.p. injection, group 4 received rapamycin (0.2 mg/kg) once every day for 21 days by i.p. injection, group 5 received a combination of ADI-PEG20 (320 IU/m$^2$) once every week for four weeks and rapamycin (0.5 mg/kg) once every day for 21 days, group 6 received ADI-PEG20 (320 IU/m$^2$) once every week for four weeks and rapamycin (0.2 mg/kg) once every day for 21 days. Mice were euthanized when tumors reached an approximate volume of 2500 mm$^3$.

Figure 16:
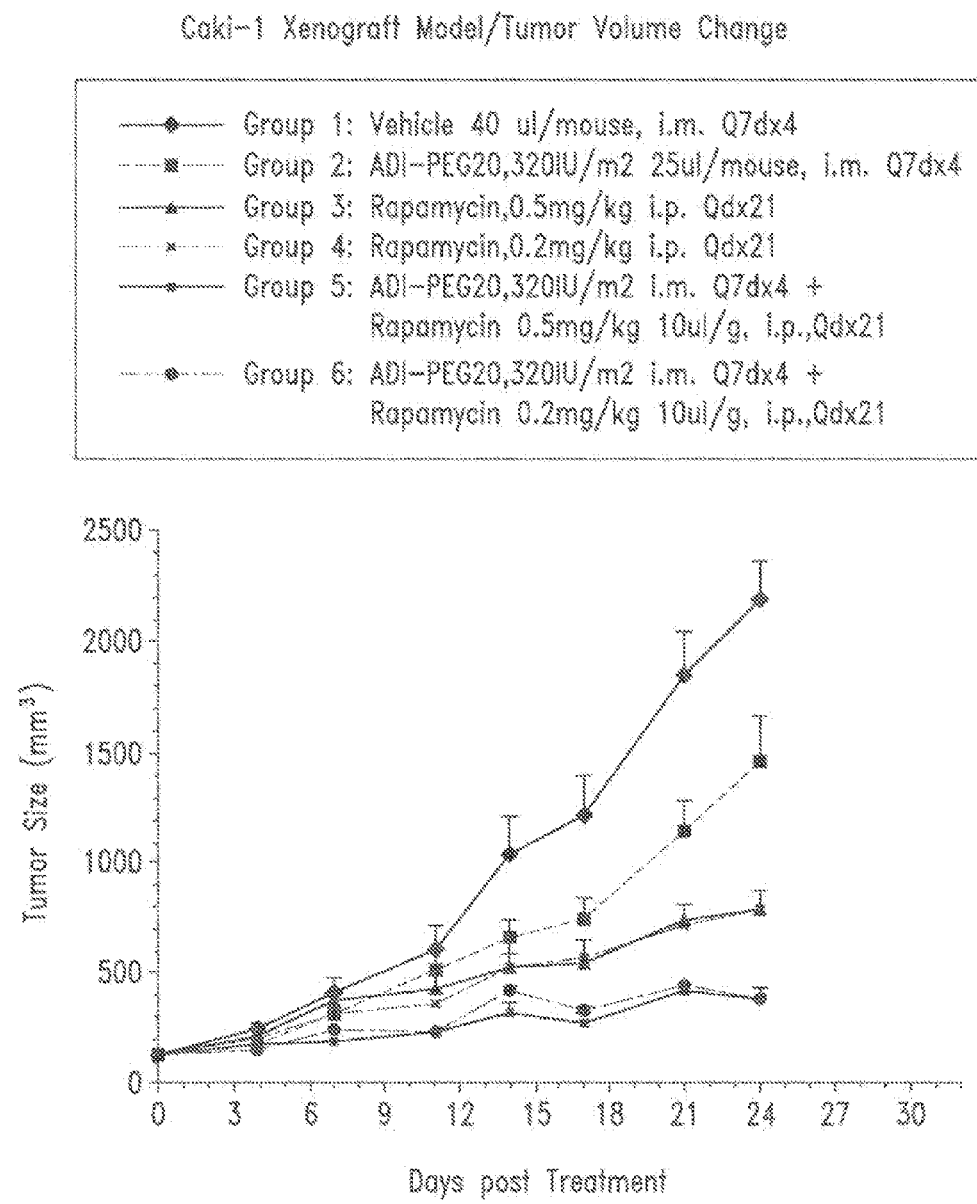
FIG. 16 shows a graph of xenograft data demonstrating that the combination of ADI-PEG 20 and rapamycin results in enhanced anti-tumor activity against the xenografted Caki-1 renal cell carcinoma cell line.

As shown in FIG. 16, the results indicated that ADI-PEG 20 and rapamycin combination synergistically enhanced tumor inhibition when compared with either ADI-PEG 20 or rapamycin alone.

The data in the literature are not consistent for different cancer types with regard to the effect of the combination of ADI-PEG 20 with autophagy inhibitors or with mTOR inhibitors such as rapamycin. Therefore, it could not have been predicted that ADI-PEG 20 in combination with rapamycin would act synergistically in inhibiting renal cell carcinoma tumors. These results indicate that the skilled person cannot predict whether any particular combination with ADI-PEG 20 will be effective for the treatment of cancer, in particular for renal cell carcinoma.

The various embodiments described above can be combined to provide further embodiments. All of the U.S. patents, U.S. patent application publications, U.S. patent application, foreign patents, foreign patent application and non-patent publications referred to in this specification and/or listed in the Application Data Sheet are incorporated herein by reference, in their entirety. Aspects of the embodiments can be modified, if necessary to employ concepts of the various patents, application and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. A sterile, liquid composition, comprising
arginine deiminase-ployethylene glycol 20K (ADI-PEG 20) and a histidine-HCl buffer which is from 0.0035M Histidine-HCl to 0.35M Histidine-HCl,
where the composition is at a pH of about 6.6 to about 7.0.

2. The sterile, liquid composition of claim 1, where the composition is at a pH of about 6.8.

3. The sterile, liquid composition of claim 1, comprising 0.035 M Histidine-HCl at pH 6.8 with 0.13 M sodium chloride.

4. A method for treating an argininosuccinate synthetase (ASS)-deficient cancer in a subject, comprising administering to the subject a composition of claim 1.

5. The method of claim 4, where the ASS-deficient cancer is selected from hepatocellular carcinoma (HCC), acute myeloid leukemia (AML), pancreatic cancer, small cell lung cancer (SCLC), metastatic sarcoma, melanoma, and renal cell carcinoma.

6. The method of claim 5, where the ASS-deficient cancer is HCC.

7. The method of claim 5, where the ASS-deficient cancer is AML.

8. The method of claim 5, where the ASS-deficient cancer is SLCL.

9. The method of claim 5, where the ASS-deficient cancer is melanoma.

10. The method of claim 4, comprising administering the composition in combination with an autophagy inhibitor, where the ASS-deficient cancer is pancreatic cancer, sarcoma, or small cell lung cancer (SCLC).

11. The method of claim 4, comprising administering the composition in combination with cisplatin, where the ASS-deficient cancer is melanoma.

12. The method of claim 4, comprising administering the composition in combination with docetaxel, where the ASS-deficient cancer is non-small cell lung cancer (NSCLC), head and neck cancer, or prostate cancer.

13. The method of claim 12, where the ASS-deficient cancer is NSCLC.

14. The method of claim 12, where the ASS-deficient cancer is prostate cancer.

15. The method of claim 4, comprising administering the composition in combination with rapamycin where the ASS-deficient cancer is renal cell carcinoma.

* * * * *

SEQUENCE LISTING

<160> NUMBER OF SEQ ID NOS: 4

<210> SEQ ID NO 1
<211> LENGTH: 409
<212> TYPE: PRT
<213> ORGANISM: Mycoplasma hominis

<400> SEQUENCE: 1

```
Met Ser Val Phe Asp Ser Lys Phe Asn Gly Ile His Val Tyr Ser Glu
1               5                   10                  15

Ile Gly Glu Leu Glu Thr Val Leu Val His Glu Pro Gly Arg Glu Ile
            20                  25                  30

Asp Tyr Ile Thr Pro Ala Arg Leu Asp Glu Leu Leu Phe Ser Ala Ile
        35                  40                  45

Leu Glu Ser His Asp Ala Arg Lys Glu His Gln Ser Phe Val Lys Ile
    50                  55                  60

Met Lys Asp Arg Gly Ile Asn Val Val Glu Leu Thr Asp Leu Val Ala
65                  70                  75                  80

Glu Thr Tyr Asp Leu Ala Ser Lys Ala Ala Lys Glu Glu Phe Ile Glu
                85                  90                  95

Thr Phe Leu Glu Glu Thr Val Pro Val Leu Thr Glu Ala Asn Lys Lys
            100                 105                 110
```

```
Ala Val Arg Ala Phe Leu Leu Ser Lys Pro Thr His Glu Met Val Glu
            115                 120                 125

Phe Met Met Ser Gly Ile Thr Lys Tyr Glu Leu Gly Val Glu Ser Glu
        130                 135                 140

Asn Glu Leu Ile Val Asp Pro Met Pro Asn Leu Tyr Phe Thr Arg Asp
145                 150                 155                 160

Pro Phe Ala Ser Val Gly Asn Gly Val Thr Ile His Phe Met Arg Tyr
                165                 170                 175

Ile Val Arg Arg Arg Glu Thr Leu Phe Ala Arg Phe Val Phe Arg Asn
                180                 185                 190

His Pro Lys Leu Val Lys Thr Pro Trp Tyr Tyr Asp Pro Ala Met Lys
            195                 200                 205

Met Pro Ile Glu Gly Gly Asp Val Phe Ile Tyr Asn Asn Glu Thr Leu
        210                 215                 220

Val Val Gly Val Ser Glu Arg Thr Asp Leu Asp Thr Ile Thr Leu Leu
225                 230                 235                 240

Ala Lys Asn Ile Lys Ala Asn Lys Glu Val Glu Phe Lys Arg Ile Val
                245                 250                 255

Ala Ile Asn Val Pro Lys Trp Thr Asn Leu Met His Leu Asp Thr Trp
            260                 265                 270

Leu Thr Met Leu Asp Lys Asn Lys Phe Leu Tyr Ser Pro Ile Ala Asn
        275                 280                 285

Asp Val Phe Lys Phe Trp Asp Tyr Asp Leu Val Asn Gly Gly Ala Glu
        290                 295                 300

Pro Gln Pro Gln Leu Asn Gly Leu Pro Leu Asp Lys Leu Leu Ala Ser
305                 310                 315                 320

Ile Ile Asn Lys Glu Pro Val Leu Ile Pro Ile Gly Gly Ala Gly Ala
                325                 330                 335

Thr Glu Met Glu Ile Ala Arg Glu Thr Asn Phe Asp Gly Thr Asn Tyr
            340                 345                 350

Leu Ala Ile Lys Pro Gly Leu Val Ile Gly Tyr Asp Arg Asn Glu Lys
        355                 360                 365

Thr Asn Ala Ala Leu Lys Ala Ala Gly Ile Thr Val Leu Pro Phe His
370                 375                 380

Gly Asn Gln Leu Ser Leu Gly Met Gly Asn Ala Arg Cys Met Ser Met
385                 390                 395                 400

Pro Leu Ser Arg Lys Asp Val Lys Trp
                405

<210> SEQ ID NO 2
<211> LENGTH: 409
<212> TYPE: PRT
<213> ORGANISM: Mycoplasma hominis

<400> SEQUENCE: 2

Met Ser Val Phe Asp Ser Lys Phe Asn Gly Ile His Val Tyr Ser Glu
1               5                   10                  15

Ile Gly Glu Leu Glu Thr Val Leu Val His Glu Pro Gly Arg Glu Ile
            20                  25                  30

Asp Tyr Ile Thr Pro Ala Arg Leu Asp Glu Leu Leu Phe Ser Ala Ile
        35                  40                  45

Leu Glu Ser His Asp Ala Arg Lys Glu His Gln Ser Phe Val Lys Ile
    50                  55                  60

Met Lys Asp Arg Gly Ile Asn Val Val Glu Leu Thr Asp Leu Val Ala
65                  70                  75                  80
```

Glu Thr Tyr Asp Leu Ala Ser Lys Ala Ala Lys Glu Glu Phe Ile Glu
            85                  90                  95

Thr Phe Leu Glu Glu Thr Val Pro Val Leu Thr Glu Ala Asn Lys Glu
        100                 105                 110

Ala Val Arg Ala Phe Leu Leu Ser Lys Pro Thr His Glu Met Val Glu
        115                 120                 125

Phe Met Met Ser Gly Ile Thr Lys Tyr Glu Leu Gly Val Glu Ser Glu
130                 135                 140

Asn Glu Leu Ile Val Asp Pro Met Pro Asn Leu Tyr Phe Thr Arg Asp
145                 150                 155                 160

Pro Phe Ala Ser Val Gly Asn Gly Val Thr Ile His Phe Met Arg Tyr
                165                 170                 175

Ile Val Arg Arg Arg Glu Thr Leu Phe Ala Arg Phe Val Phe Arg Asn
                180                 185                 190

His Pro Lys Leu Val Lys Thr Pro Trp Tyr Tyr Asp Pro Ala Met Lys
            195                 200                 205

Met Ser Ile Glu Gly Gly Asp Val Phe Ile Tyr Asn Asn Glu Thr Leu
210                 215                 220

Val Val Gly Val Ser Glu Arg Thr Asp Leu Asp Thr Ile Thr Leu Leu
225                 230                 235                 240

Ala Lys Asn Ile Lys Ala Asn Lys Glu Val Glu Phe Lys Arg Ile Val
                245                 250                 255

Ala Ile Asn Val Pro Lys Trp Thr Asn Leu Met His Leu Asp Thr Trp
            260                 265                 270

Leu Thr Met Leu Asp Lys Asn Lys Phe Leu Tyr Ser Pro Ile Ala Asn
        275                 280                 285

Asp Val Phe Lys Phe Trp Asp Tyr Asp Leu Val Asn Gly Gly Ala Glu
        290                 295                 300

Pro Gln Pro Gln Leu Asn Gly Leu Pro Leu Asp Lys Leu Leu Ala Ser
305                 310                 315                 320

Ile Ile Asn Lys Glu Pro Val Leu Ile Pro Ile Gly Gly Ala Gly Ala
                325                 330                 335

Thr Glu Met Glu Ile Ala Arg Glu Thr Asn Phe Asp Gly Thr Asn Tyr
            340                 345                 350

Leu Ala Ile Lys Pro Gly Leu Val Ile Gly Tyr Asp Arg Asn Glu Lys
        355                 360                 365

Thr Asn Ala Ala Leu Lys Ala Ala Gly Ile Thr Val Leu Pro Phe His
370                 375                 380

Gly Asn Gln Leu Ser Leu Gly Met Gly Asn Ala Arg Cys Met Ser Met
385                 390                 395                 400

Pro Leu Ser Arg Lys Asp Val Lys Trp
                405

<210> SEQ ID NO 3
<211> LENGTH: 18
<212> TYPE: DNA
<213> ORGANISM: Homo sapiens
<220> FEATURE:
<221> NAME/KEY: misc_feature
<222> LOCATION: (1)..(18)
<223> OTHER INFORMATION: Forward PCR primer used to amplify
      argininosuccinate synthetase cDNA

<400> SEQUENCE: 3
tttaagcaga ctaagggg                                                18

```
<210> SEQ ID NO 4
<211> LENGTH: 21
<212> TYPE: DNA
<213> ORGANISM: Homo sapiens
<220> FEATURE:
<221> NAME/KEY: misc_feature
<222> LOCATION: (1)..(21)
<223> OTHER INFORMATION: Reverse PCR primer used to amplify
      argininosuccinate synthetase cDNA

<400> SEQUENCE: 4
ccatcccagg ttataagcac a                                          21
```